United States Patent [19]

Demarest et al.

[11] Patent Number: 5,438,746
[45] Date of Patent: Aug. 8, 1995

[54] NEEDLE THREADING AND SWAGING SYSTEM

[75] Inventors: David Demarest, Parsippany; Robert B. Duncan, Bridgewater; John F. Blanch, Tinton Falls, all of N.J.

[73] Assignee: Ethicon, Inc., Somerville, N.J.

[21] Appl. No.: 181,598

[22] Filed: Jan. 13, 1994

[51] Int. Cl.[6] .......................... B23P 23/00; B21G 1/02
[52] U.S. Cl. ..................................... 29/564.6; 29/517; 72/423; 163/1; 163/5
[58] Field of Search ............... 163/1, 5; 29/33 R, 563, 29/33 J, 33 P, 564.4, 564.6, 564.7, 515, 517, 243.517, 505; 606/226; 72/413, 416, 402, 423

[56] References Cited

U.S. PATENT DOCUMENTS

| | | | |
|---|---|---|---|
| 2,620,028 | 12/1952 | Kohut | 163/5 |
| 3,611,551 | 10/1971 | Shave et al. | 29/515 |
| 3,980,177 | 9/1976 | McGregor | 206/63.3 |
| 4,072,041 | 2/1978 | Hoffman et al. | 72/416 |
| 4,722,384 | 2/1988 | Matsutani | 163/1 |
| 4,806,737 | 2/1989 | Coates | 219/390 |
| 4,832,025 | 5/1989 | Coates | 128/335.5 |
| 4,922,904 | 5/1990 | Uetake et al. | 29/517 X |
| 5,226,336 | 7/1993 | Coates | 83/170 |

FOREIGN PATENT DOCUMENTS

| | | | |
|---|---|---|---|
| 212027 | 9/1988 | Japan | 163/1 |
| 299834 | 12/1988 | Japan | 163/5 |
| 3106530 | 5/1991 | Japan | 163/1 |

Primary Examiner—William Briggs
Attorney, Agent, or Firm—Audley A. Ciamporcero, Jr.; E. Richard Skula

[57] ABSTRACT

An automated machine for attaching a suture to a surgical needle comprises a first apparatus located at a first predetermined location for sorting a plurality of randomly oriented needles and orienting each needle for automatic handling at a first predetermined location, each of the needles having a suture receiving opening formed therein. A second apparatus located at a second predetermined location is provided for automatically cutting an indefinite length of suture material to a definite length suture strand and for automatically inserting an end of the definite length suture strand into the suture receiving opening formed in the needle. Also provided is a third apparatus for swaging the needle to close the suture receiving opening about the suture to secure said suture thereto and form therefrom a needle and suture assembly. An indexing device automatically receives each individual needle in a predetermined orientation at the first predetermined location and conveys the needle for sequential processing from the first to the second locations to form the needle-suture assembly.

97 Claims, 33 Drawing Sheets

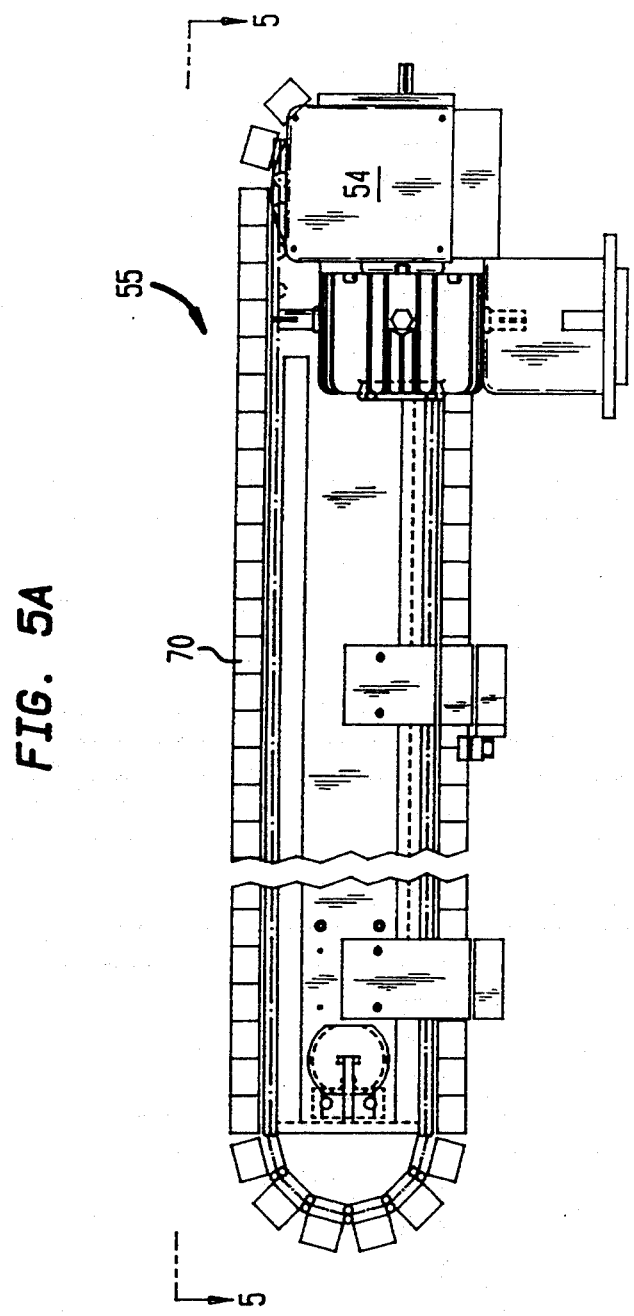

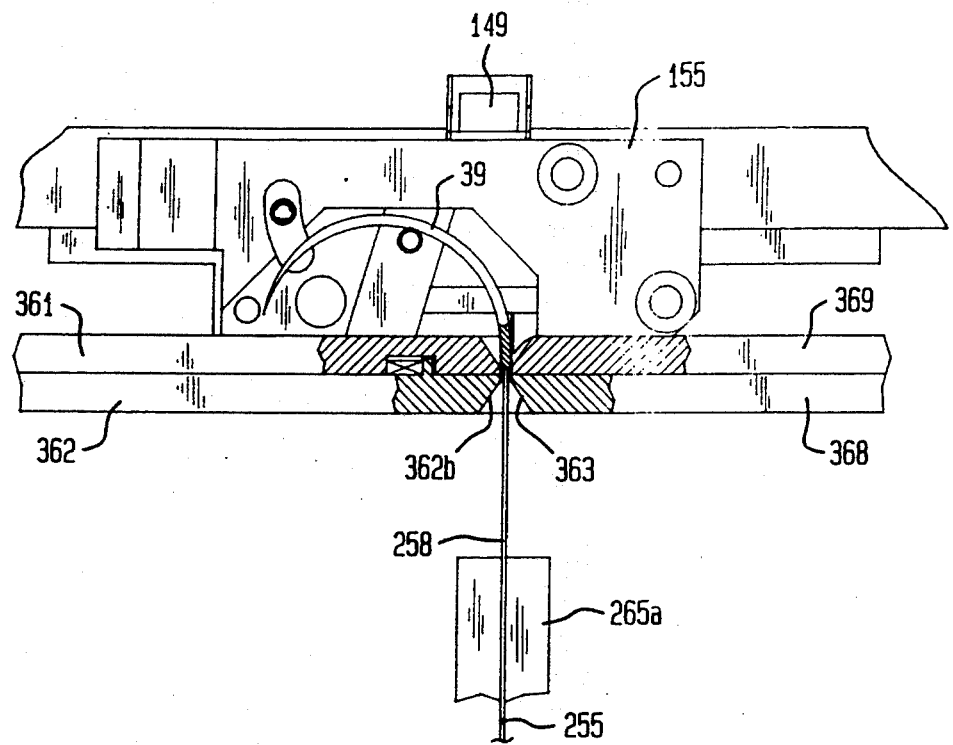
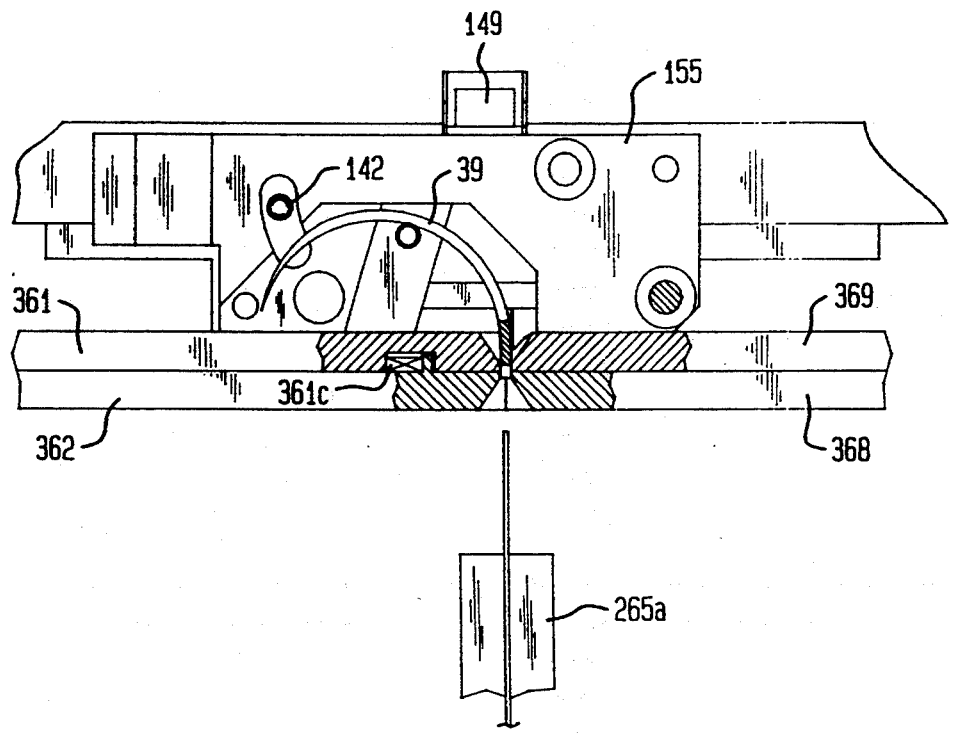

NEEDLE THREADING AND SWAGING SYSTEM

FIELD OF THE INVENTION

The present invention relates generally to machines for automatically packaging needles, such as surgical needles and the like, and more specifically, to an apparatus that automatically manufactures, tests, and conveys armed surgical needles, i.e., needles having a suture strand of predetermined length attached at one end thereof, for automatic packaging in a reduced size organizer of unique construction.

DESCRIPTION OF THE PRIOR ART

Most armed surgical needles, i.e., needles having sutures attached to one end thereof, that are in present use by surgeons and medical personnel, are manufactured utilizing manual and semi-automated procedures such as those described in U.S. Pat. Nos. 3,611,551, 3,980,177, and 4,922,904. For instance, as described in U.S. Pat. No. 3,611,551, manual intervention is required by an operator to accurately position a suture within the needle for swaging and to adjust swaging dies to increase or decrease swage pressure when suture strands of different gauges are to be swaged. This process is costly in terms of man-hour labor and efficiency because manual positioning is required for swaging to take place.

Presently, suture material may be supplied wound on a bobbin, or, a king or driven spool before being cut and positioned within the swaging end of a surgical needle. In U.S. Pat. No. 3,980,177 the suture material is fed from a spool and taken up on a rotating tension rack where uniform length strands are subsequently cut. Thus, the length of the suture is determined by the size of the rack and manual intervention is required to prepare the rack for the cutting of the suture material wound thereabout. Moreover, manual intervention is required to change the rack each time a suture strand of different length is desired.

In U.S. Pat. No. 4,922,904, the suture material is supplied wound on a bobbin and is fed through various guide means and a heater for straightening the material, prior to insertion within the crimping cavity of the surgical needle. In one embodiment shown therein, an elaborate television monitoring means is required for aligning the drawn suture within the crimping cavity of the surgical needle prior to swaging thereof. In the same embodiment, a rotary encoder device is used to determine the length of suture material unwound from the bobbin prior to cutting. In an alternative embodiment, after swaging of the indefinite length of suture material to the needle, the needle-suture assembly is fed a predetermined distance prior to cutting to obtain a suture strand of predetermined length. Thus, to obtain uniform lengths of suture material every time requires careful manipulations and precise controls, and the processes used to accomplish these tasks are also costly in terms of man-hour labor and efficiency.

The requirement of the surgeon or medical personnel using the armed needle to be able to detach the needle from the suture after suturing to avoid the necessity of cutting the suture with scissors had been addressed in the above-mentioned U.S. Pat. No. 3,980,177. The patent itself is drawn to a needle-suture combination that is characterized as having a straight pull-out (destructive pull-out) value between 3 ounces and 26 ounces depending upon the size of the suture. This patent, however, does not disclose any means for automatically testing the armed-needle to determine its pull-out value, i.e., the means for providing the force necessary to detach the needle from the suture.

In the above-mentioned U.S. Pat. No. 4,922,904, a means for confirming whether or not a length of suture has been firmly connected to the surgical needle is provided by applying tension to the suture after swaging thereof and prior to cutting the suture. However, no means or method is provided for determining the amount of force that is required to separate the needle from the suture.

Thus, it would be desirable to provide a needle threading and swaging system that is fully automated and which can automatically prepare surgical needles having uniform lengths of suture material attached thereto.

It would also be highly desirable to provide a needle threading and swaging system that is fully automated and which can automatically manufacture armed and pull-tested surgical needles at a rate of approximately sixty per minute.

Moreover, it would be highly desirable to provide a needle threading and swaging system that incorporates a swaging station which accomplishes drawing an indefinite length strand of suture material, cutting the strand at a predetermined length, and swaging the suture to a precisely positioned surgical needle.

Additionally, it would be highly desirable to provide a needle threading and swaging system that incorporates a needle sorting device for sorting and feeding individual surgical needles in an oriented position to a swaging station for automatic swaging of a suture strand thereto.

Furthermore, it would be highly desirable to provide a needle threading and swaging system that is operable under the control of a control system computer and that can provide automatic adjustments to the positions of the swage tooling dies.

SUMMARY OF THE INVENTION

Accordingly, it is an object of the instant invention to provide a cost-effective automatic needle threading and swaging system that virtually eliminates operator exposure to repetitive manual operations.

It is another object of the instant invention to provide an automatic needle threading and swaging system that incorporates a rotatable swage dial having a plurality of multi-axis grippers for automatically engage and index surgical needles to a plurality of processing stations that include: a loading station for transferring individual precisely oriented surgical needles from a conveyor to the multi-axis grippers; a swaging station that automatically draws an indefinite length strand of suture material, cuts the strand, inserts the free end of the definite length strand within the suture receiving opening of the needle, and swages the suture strand to the surgical needle; a pull-test station that automatically performs minimum and destructive pull-testing of the needle-suture combination; and finally, a discharge station for transferring armed, pull-tested needles to a packaging station for automatic packaging thereof.

It is still another object of the instant invention to provide an automatic needle threading and swaging system that incorporates a cost-effective needle sorting device at the loading station.

Furthermore, it is another object of the instant invention to provide an automatic needle threading and swaging system which can automatically cut uniform lengths of suture material at high-speeds.

Yet another object of the present invention is to provide a needle threading and swaging system that incorporates an automatic swaging station that performs suture insertion and automatic swaging in approximately one second.

Yet another object of the present invention is to provide a needle threading and swaging system that incorporates an optional heat tipping assembly for heating the suture strand to stiffen a portion thereof.

Yet still another object of the present invention is to provide a needle threading and swaging system that incorporates an automatic pull-test station that can perform a minimum pull-test or a destructive pull-test of the armed needle in less than one second.

Moreover, it is still another object of the present invention to provide a needle threading and swaging system that is operable under the control of a control system computer.

Yet still another object of the present invention is to provide a needle threading and swaging system that incorporates a discharge station for discharging precisely oriented armed surgical needles for automatic packaging thereof.

Further yet, another object of the present invention is to provide a needle threading and swaging system that can provide automatic swage die and tool adjustments without unnecessary interruptions and without manual intervention.

These and other objects of the present invention are attained with an automated machine for attaching a suture to a surgical needle comprising a first means located at a first location for sorting a plurality of randomly oriented needles and orienting each needle for automatic handling at a first predetermined location, each of the needles having a suture receiving opening formed therein. A second means located at a second location is provided for automatically cutting an indefinite length of suture material to a definite length suture strand and for automatically inserting an end of the definite length suture strand into the suture receiving opening formed in the needle at a second predetermined location. Also provided is a third device for swaging the needle to close the suture receiving opening about the suture to secure said suture thereto and form therefrom a needle and suture assembly. An indexing device automatically receives each individual needle in a predetermined orientation at the first predetermined location and conveys the needle for sequential processing from the first to the second locations.

Further benefits and advantages of the invention will become apparent from a consideration of the following detailed description given with reference to the accompanying drawings, which specify and show preferred embodiments of the invention.

BRIEF DESCRIPTION OF THE DRAWINGS

FIG. 5(a) is a side view of the precision conveyor 55 for transporting needles in a specific orientation to an automatic swaging station.

FIG. 18(a) is detailed top view of the cam dial assembly 120 having cam dial plate 125 with cam follower 165a in a retracted position within cam track 160a.

FIG. 18(b) is cut away top view of the cam dial plate 125 showing cam follower 165a in an extended position within cam track 160a.

FIGS. 27(b)-27(f) illustrate the multi-axis needle gripper 155 and swaging and suture alignment dies shown in various stages of the suture insertion and needle swaging sequence.

DETAILED DESCRIPTION OF THE PREFERRED EMBODIMENT

Figure 1:
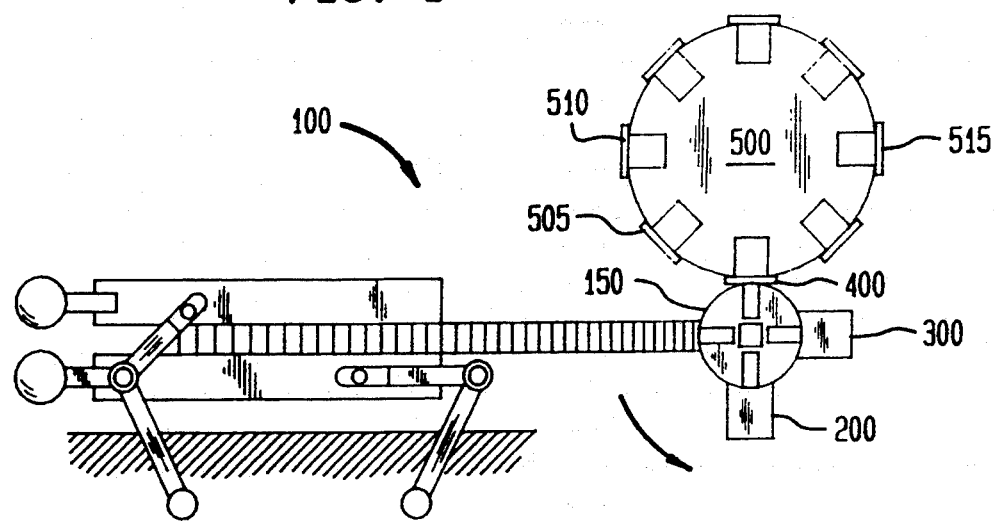
FIG. 1 is a conceptual top view of the needle threading and swaging system incorporating a needle sorting device 100 for feeding individual needles onto a multi-axis gripper mounted on a rotary swage dial 150, the automatic swaging station 200, the automatic pull-test station 300, and the armed needle discharge station 400 of the present invention.

Generally, in the automatic needle threading and swaging system of the present invention, parallel operations take place simultaneously at four (4) different stations to ensure that approximately sixty (60) armed surgical needles are assembled and discharged per minute. For instance, as shown in FIG. 1, the needle sorting apparatus 100 sorts, singulates, and conveys precisely oriented surgical needles to a plurality of grippers mounted on the rotary swage dial 150. The rotary swage dial then rotates counterclockwise as shown by the arrow in FIG. 1, to index each needle to the automatic swaging station 200 where the suture material is cut, inserted into the needle, and automatically swaged thereto. Next, the rotary swage dial 150 rotates further to index the armed needle to the automatic pull-test station 300 where each armed needle is pull-tested to ensure that the minimum and/or destructive pull-test requirements of the medical profession, are met. Finally, the rotary swage dial indexes the pull-tested armed needle to the discharge station 400 where the armed surgical needles are handed off to a suture winding and packaging dial 500 where the needles are automatically packaged in a reduced size organizer package of unique arrangement and construction.

Figure 2A:
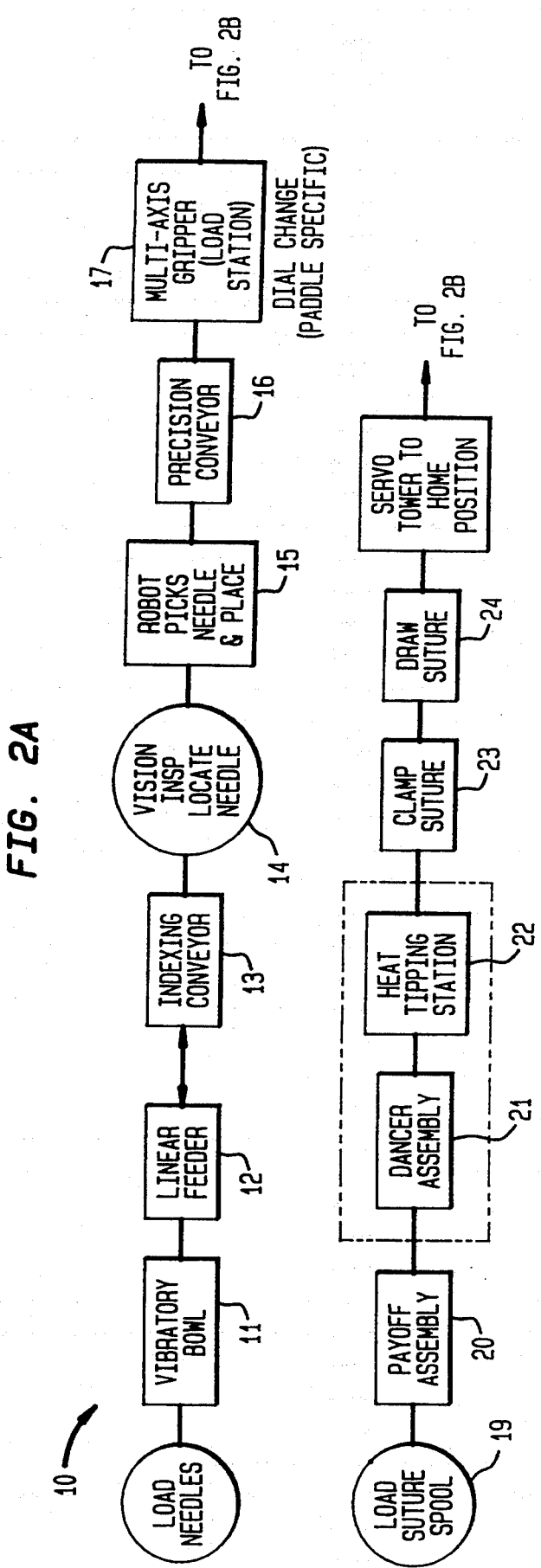
FIGS. 2(a)-2(b) is a flow diagram illustrating the process for the needle threading and swaging system of the present invention.
Figure 2B:
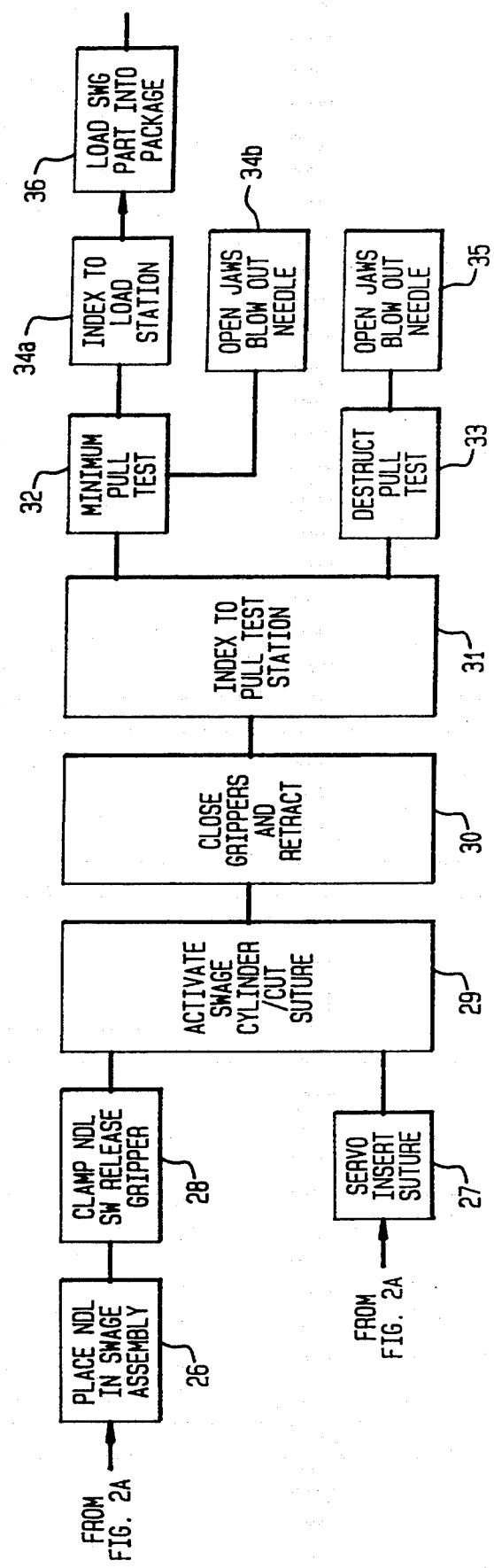

FIGS. 2(a) and 2(b) are block diagrams which illustrate the automatic needle threading and swaging process 10 of the instant invention. For instance, at the needle sorting apparatus 100, needles are first loaded into a vibratory bowl at step 11, automatically sorted and linearly fed at step 12 to a translucent indexing conveyor at step 13, evaluated with respect to orientation and position by a vision tracking system at step 14, picked up by a robot apparatus at step 15, transferred to a precision conveyor by the robot apparatus at step 16, and finally conveyed to a load station where the needles are transferred to a multi-axis gripper located on a rotary swage dial 150 for subsequent transfer to the swaging station 200 indicated at step 17. A detailed explanation of the apparatus used to carry out each step will be explained in further detail hereinbelow.

Simultaneous with the needle sorting process described above with respect to steps 11 through 17, an automatic suture cutting and swaging process takes place at the swaging station 200 shown in FIGS. 2(a) and 2(b) with respect to steps 19 through 30. Indefinite length suture material is supplied in various spools and configurations that may carry up to 5000 yards of material. This is indicated at step 19 in FIG. 2(a). Next, at step 20, the suture material is loaded into a payoff assembly which is part of a drawing tower apparatus to be described in detail below. This payoff assembly includes grippers that alternately draw the suture material from the spool to enable cutting thereof. When larger spools of material are used, the material may be optionally loaded in a driven spool feed assembly with a dancer as indicated at optional step 21 to ensure that the material does not break or snap when in tension.

While the material is being drawn, it may require extra treatment or processing. For instance, as described in detail below, it may be desirable to heat the suture material under tension at the suture tip in order to stiffen the material to facilitate the positioning thereof within the suture receiving opening of a surgical needle. Thus, at optional step 22, heat may be applied to a portion of suture material. At step 23 of the block diagram of FIG. 2(a), the suture material is gripped by the servo grippers. At step 24, the suture strand is drawn up the tower and positioned for insertion within the suture receiving opening of the needle for swaging.

After a surgical needle is indexed to the swaging station 200 as described above, the multi-axis gripper positions the needle in a precisely oriented position at the swage die opening formed at the ends of two swaging dies of a swage assembly as indicated as step 26 in FIG. 2(b). Simultaneously, the suture strand is drawn from a king spool along a single axis of a drawing tower to register a tip thereof for insertion within the suture receiving end of the needle. Next, at step 27, the gripper assembly at the drawing tower inserts the tip of the suture strand within a lower funnel guide for accurate positioning within the suture receiving opening of the needle that is aligned with the suture drawing axis. Then, at step 28, the multi-axis gripper releases its grip on the needle placed within the swage die opening. At step 29, the swage cylinder is activated to automatically swage the suture to the needle and to cut the indefinite length of suture strand at a predetermined length. While retaining the armed needle, the multi-axis gripper is then retracted at its station on the rotary swage dial as shown as step 30 and indexed to a pull-test station 300 at step 31 so that minimum pull-testing at step 32 or destructive pull-testing at step 33 may be performed.

Depending upon the results of the minimum pull-test, the armed needle will either be indexed by the rotary swage dial to the discharge station 400 where the armed needle will be discharged to the suture winding and packaging dial 500 if the pull-test requirements are met (as shown as step 34a in FIG. 2(b)), or, will be discharged at the pull-test station if the needle fails the minimum pull-test (as shown as step 34b in FIG. 2(b)). The destructive pull-test always renders the armed needle incapable of further processing so the needle is automatically discharged at the pull-test station 400 as indicated at step 35 in FIG. 2(b). Finally, as shown as step 36 in FIG. 2(b), armed needles passing the minimum pull test are conveyed to a discharge station 400 where the individual armed needles are loaded for packaging in a reduced size organizer package of unique construction.

A detailed explanation of the apparatus used to carry out each step in the suture cutting process will be explained in further detail hereinbelow.

Needle Sorting Station

Figure 3:
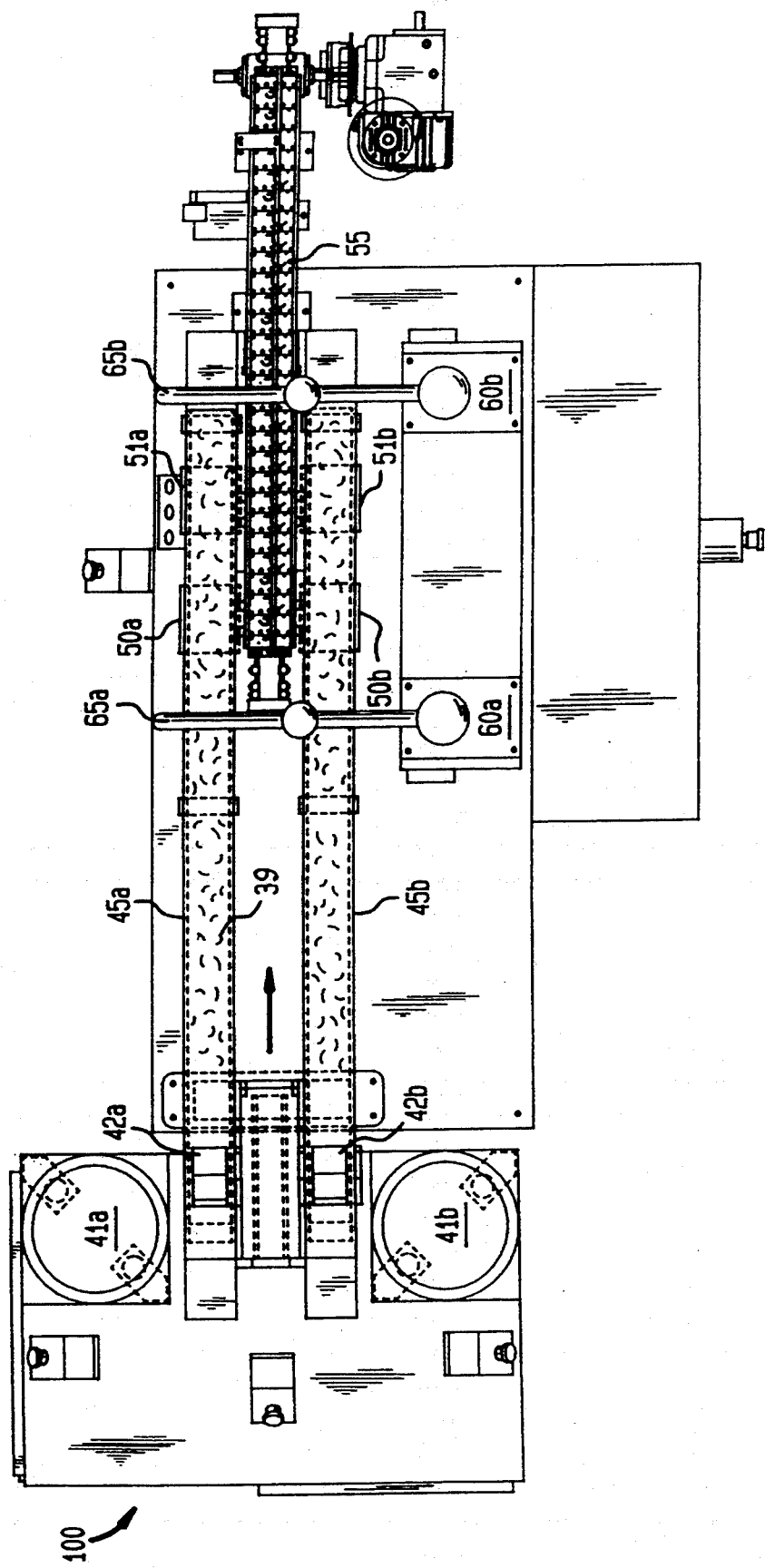
FIG. 3 is a top view of the needle sorting station 100 of the instant invention.

The preferred embodiment of the needle sorting apparatus 100 for carrying out the needle sorting process is illustrated in FIG. 3. As shown therein, needles 39 are delivered in bulk to each of two vibratory bowls or hoppers 41a, b where they are singulated by respective singulating assemblies 42a, b and randomly deposited upon each of two translucent conveyors 45a, b. The two conveyors 45a, b carry the randomly deposited needles 39 in the direction indicated by the arrow in FIG. 3 where their position and orientation are evaluated by a remotely located vision tracking system. This tracking system, evaluates the position and orientation of the needles upon each translucent conveyor 45a, b as they pass along respective first illuminated platforms 50a, and 50b. The orientation and positional information obtained from the vision tracking system is processed by a control system computer and converted to information usable by a first robot assembly 60a for picking up and transferring the tracked needle at a rate of approximately thirty (30) transfers per minute from the translucent conveyor to a precision conveyor 55 which is also moving in the same direction as the translucent conveyors. The control system executes an algorithm for instructing an arm or grappler 65a of the robot assembly 60a to grab the tracked needle from either of the two conveyors 45a, b. If there is a temporary shortage of needles, i.e., if the randomly deposited needles 39 are oriented such that the first robot arm 65a is unable to pick them up because of its limited range of motion, a second robot assembly 60b is provided to ensure that the same tracked needle or another selected needle will be picked up by its grappler or arm 65b and transferred to the precision conveyor 55. This is accomplished by the aforementioned tracking system which also evaluates the position and orientation of the needles upon each translucent conveyor 45a, b as they pass along respective second illuminated platforms 51a, and 51b. The redundancy designed into this needle sorting system is necessary to ensure that there are no shortages of needles 39 being fed by the precision conveyor 55 to the multi-axis gripper mounted on the rotary swage dial 150, and consequently, that there are no shortages of needles being indexed to the automatic high-speed swaging station 200 where a rate of approximately sixty (60) swages per minute can be achieved. For ease of description, the redundant portion of the needle sorting apparatus will be omitted from the description below.

Figure 4:
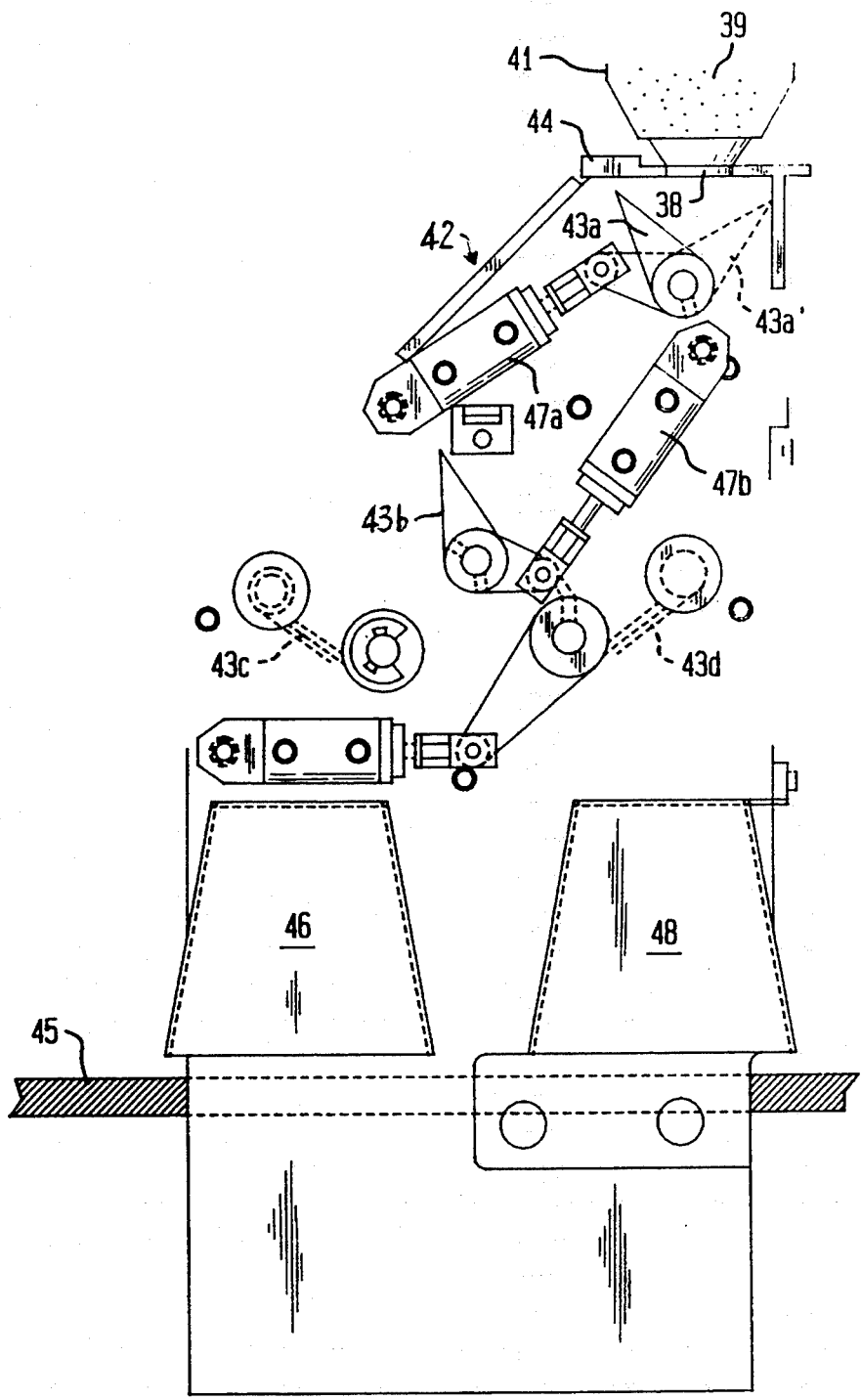
FIG. 4 is a detailed side view of the needle infeed means for singulating and depositing needles onto a translucent conveyor.

The first step of the needle sorting process 100 involves introducing a predetermined amount of needles 39 from an infeed device, such as a bowl or hopper, into a needle singulating assembly. In the preferred embodiment shown in the side view of FIG. 4, a vibratory hopper or bowl 41 is provided with a suitable optical or mechanical counting device such as sensor plate 44 so that up to six (6) needles may be periodically fed into the sorting assembly 42 at any one time. The needles 39 are discharged from the vibratory hopper 41 through a gate 38, and fall by gravity through a needle singulating assembly 42 which comprises a series of diverter doors 43a, b and trap doors 43c, d that alternate between two positions to allow one half of the needles discharged to drop onto each of two spaced-apart chutes 46, 48 and finally onto a moving translucent conveyor 45. With the diverter door 43a in the position shown in FIG. 4(a), any needle 39 introduced into the needle singulating assembly 42 will be deflected and fall into an external receptacle (not shown) where the needles may be subsequently returned to the hopper 41. When divertner door 42a is in a second position indicated by the dotted line diverter 43a' in FIG. 4(a), six (6) needles 9 will be counted by 44 sensor as they fall through the sorting assembly so that they may be further singulated by appropriate switching of diverter door 43b and trap doors 43c, d. The purpose of the diverter doors 43a, b and trap doors 43c, d in the sorting assembly 42 is to ensure that an inordinate number of needles 39 do not fall onto the conveyor 45 at one time, and to ensure that the needles are adequately spaced apart when deposited. Preferably, the diverter doors 43a, b operate under the control of an automatic control system and are timed to alternate between two positions preferably at a rate which will to allow approximately three (3) needles per cycle to drop onto translucent conveyor 45 via each of the respective discharge chutes 46, 48. Both diverter doors 43a, b are respectively driven by cylindrical pistons 47a, b and suitable solenoid or pneumatic motors (not shown). It should be understood that any needle 39 deposited on translucent conveyor 45 will be randomly positioned and unoriented.

In the preferred embodiment, the translucent conveyor 45 is an endless belt conveyor that runs parallel to a precision conveyor 55 as shown in FIG. 3. As will be explained in further detail below, a robot assembly 60 that is located downstream from the needle singulating assembly 42 and proximate both the precision and translucent conveyors, transfers the individual randomly positioned needles 39 from the translucent conveyor 45 to engagement devices located on the precision conveyor 55. The precision conveyor 55 enables transfer of the precisely oriented needles to a multi-axis gripper located on a rotary swage dial 150 for subsequent conveyance to the automatic swaging station 200.

As described above, and in view of FIGS. 3 and 8, the robot assembly comprises two robots 60a, b located downstream from each needle singulating assembly 42a, b and proximate both the precision and translucent indexing conveyors. In the preferred embodiment described herein, each robot assembly 60a, b is an Adept® 604-S robot capable of accomplishing needle transfers at a rate of approximately 40 transfers per minute as controlled by each robot's corresponding Adept® CC controller. Each robot is a four-axis SCARA (Selective Compliance Assembly Robot Arm) robot comprising four joints capable of a variety of motion. Robot grippers 65a, b are attached to the quill of each respective robot assembly 60a, b and are enabled to provide gripping action by pressure supplied from an air cylinder (not shown).

Figure 5B:
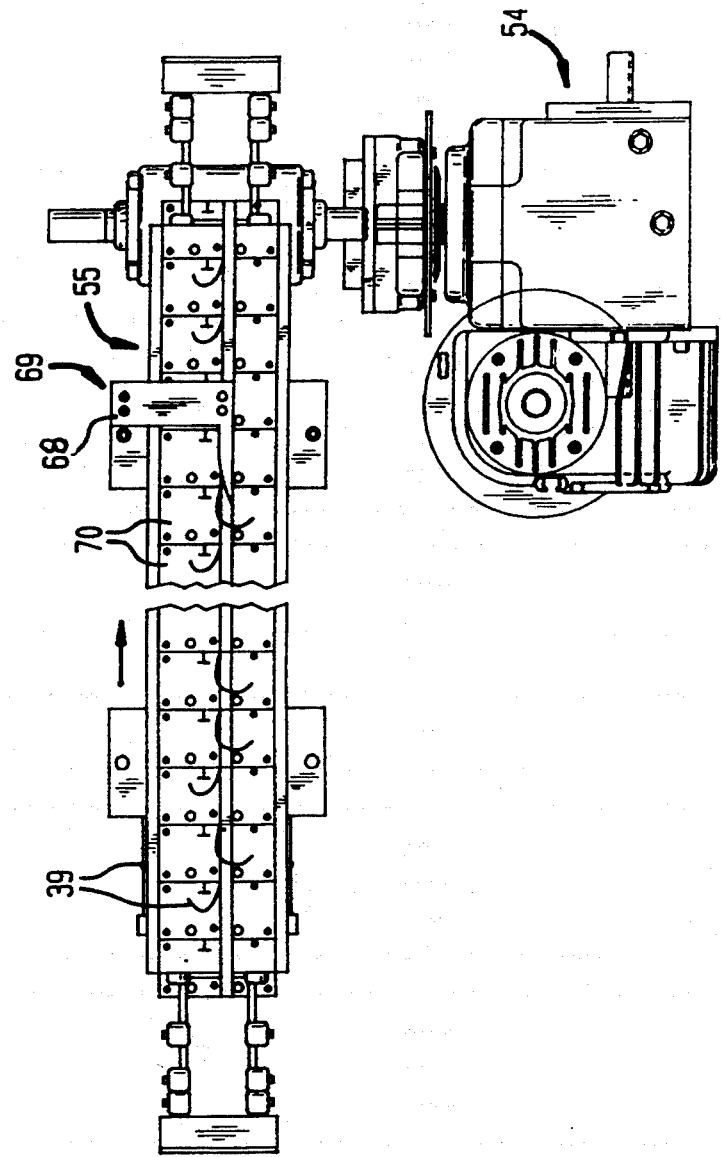
FIG. 5(b) is a detailed top view of the precision conveyor taken from line 5—5 of FIG. 5(a) and is shown carrying needles that have been positioned thereon.
Figure 8:
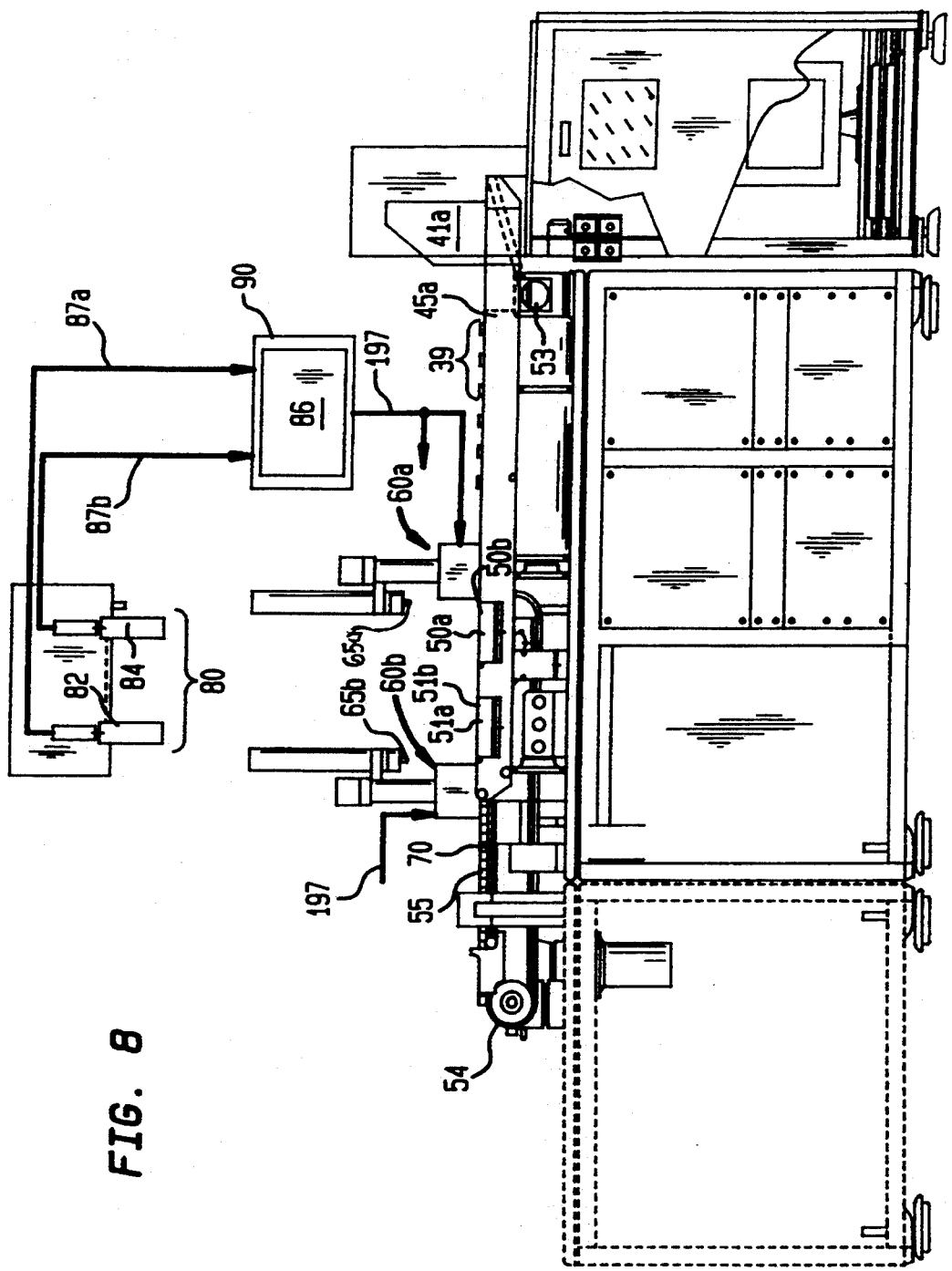
FIG. 8 illustrates a side elevational view of the robot assembly 60 positioned above the translucent and precision conveyors and the camera assembly 80 comprising two video cameras interfaced with the computer control system 90 for tracking the position of individual needles 39.

Referring now to FIG. 8, there is illustrated the precision conveyor 55 which is driven by drive motor assembly 54 at a rate sufficient to index and transfer one oriented surgical needle per second (1 needle/sec) to the automatic swaging machine. A similar drive motor assembly 53 is provided for driving the indexing conveyors 45a, b. As will be explained in detail below, each drive motor assembly 53, 54 is interfaced with and operate under the control of the control system 90 to pause the indexing motion to enable the pick-up and transfer of a needle from the indexing conveyor to the precision conveyor. FIGS. 5(a) and 5(b) illustrate in detail the precision conveyor 35 and the plurality of engagement boats 70 located thereon for engaging respective individual surgical needles 39. Motion of the precision conveyor 55 is also paused periodically at the desired cycle rate to allow for the transfer of the needles 39 thereto from the robots 60a, b. In the preferred embodiment, the control system 90 includes a programmable logic controller (PLC) that is in digital communication with the Adept® robot controllers and the vision tracking system components to control the infeed system.

As shown in FIG. 8, the vision tracking system comprises a camera assembly 80 having two video cameras 82 and 84, one located overhead each respective illuminated platform portion, 50a and 51a, for its indexing conveyor 45a. As will be explained in detail below, the video images of the needles obtained from each camera 82, 84 are bit-mapped or suitably digitized and transmitted via suitable transmission media, such as communication lines 87a, b shown in FIG. 8, to the remotely located control system computer 90 where a Vision Control task processes the video images and inputs the data to each robot 60a, b, via communication line 197. Preferably, the conveyors 45a and 45b are translucent and are backlit at the respective portions 50a, b and 51a, b so that a sharp video image may be obtained by the overhead camera assembly for processing. It is understood that for descriptive purposes, only two video cameras 82, 84 corresponding to the two illuminated platforms 50a, 50b are shown in FIG. 8. However, the invention includes a second set of video cameras (not shown) corresponding to illuminated platforms 50b and 51b for conveyor 45b (FIG. 3) so that, as mentioned above, binary images of needles on conveyor 45b may be obtained while the robots are picking and placing needles from conveyor 45a. The redundancy designed into this system ensures that there will be no momentary shortage of needles fed to the swaging station and that maximum throughput of oriented needles for input to the swaging station is achieved. In the event the state of robotics technology improves, and as the robot assemblies achieve greater degrees of movement at faster speeds, the second set of cameras and a second robot assembly may no longer be required. Furthermore, a robotic assembly of sufficient speed and precision may be able to pick up randomly deposited needles from a moving conveyor and place them directly in an oriented position at the swaging station.

In the preferred embodiment, each camera 82, 84 is mounted approximately one (1) meter above each backlit indexing conveyor 45a, b and utilizes an electrically controlled telephoto lens with a focal distance ranging from 10 mm to 140 mm that may be changed with suitable adaptors. Suitable lens controllers are used to establish lighting/iris, focus, and field of view for each camera lens, and, are interfaced with the Adept® controller via an RS-232 link.

A further component of the control system for the needle sorting and infeed apparatus includes an SCADA Node which is used to oversee and direct the infeed system. This node interfaces with each of the Adept® controllers via discrete RS-232 links which are used to download data information, such as needle parameters, error messages, and status messages, to the Adept® controllers. The SCADA node may comprise a personal computer or such suitable device, running commercially available FIXDMACS® software. Serial communication is used to exchange the needle parameters entered at the FIX/DMACS "Adept ®️ Setup" screen during a needle changeover procedure which is used to inform the infeed system of the size and type of needles to be processed. After an operator enters the needle parameters and initiates a changeover, the FIX/DMACS Node will transmit these parameters to the robot controller(s).

Figure 13:
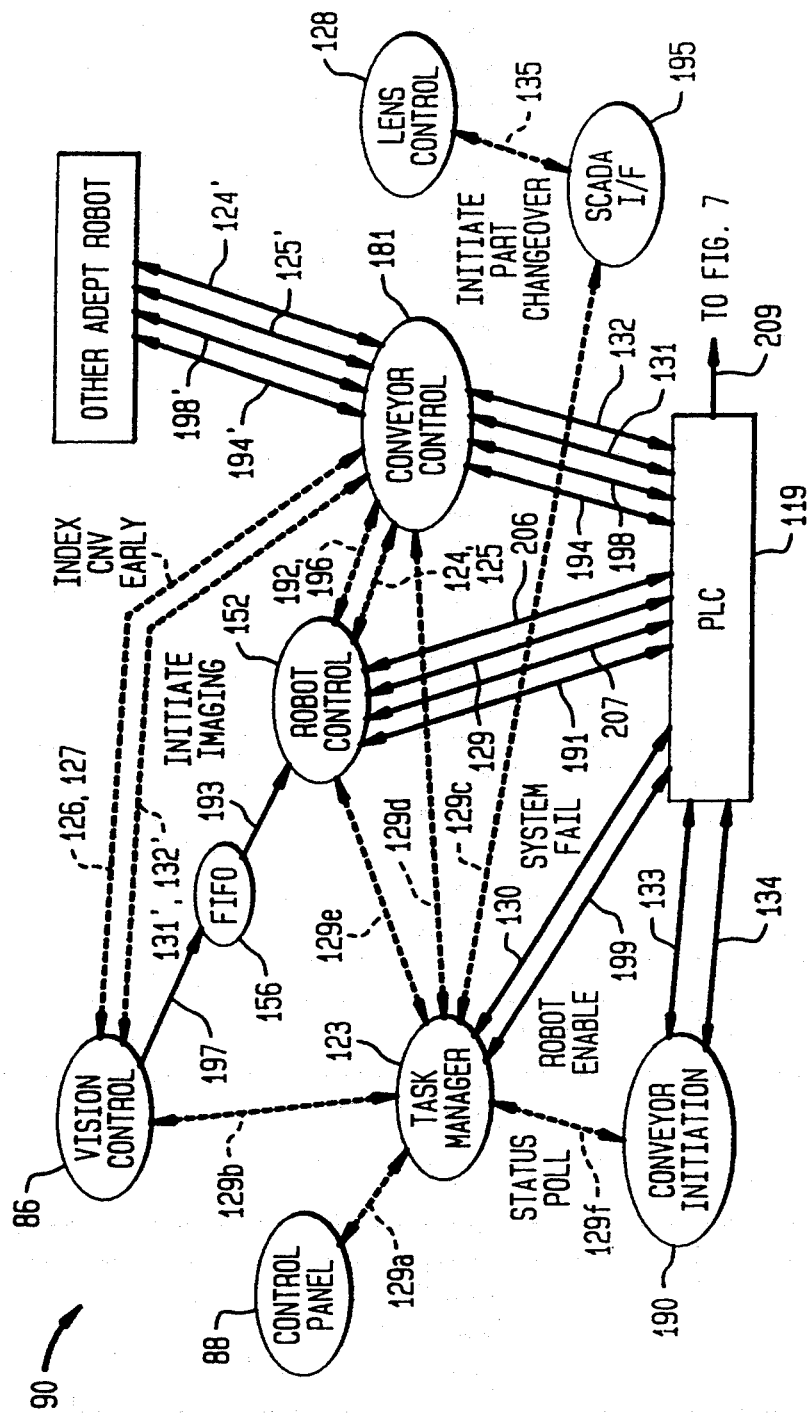
FIG. 13 is a schematic representation of the control and data flow for each of the control tasks of the needle sorting apparatus.

The robotic/vision control system 90 of the invention comprises individual computer software programs, each associated with a particular task to be performed by the needle sorting and infeed system 42 and executed under the control of the PLC 119. As shown in FIG. 13, the software architecture for controlling the needle sorting apparatus of the instant invention performs eight (8) main tasks: a Robot Control task 152; a Vision Control task 86; a Conveyor Indexing Control task 181; a SCADA Node Interface task 195; A Control Panel task 88; a Task Manager 123; a Conveyor Initiation task 190; and, a Lens Control task 128. Of these eight tasks mentioned above, the first six are active during the needle infeed steady state operation as will be explained below. FIG. 13 additionally shows the data flow among the tasks and the signals which initiate the tasks. It is understood that the software language used in the preferred embodiment, is Adept's V/V+ language, which supports both vision and robotic control in a multitasking environment. Each of the tasks will be generally described below with respect to FIG. 13. A more detailed description of the following tasks can be found in the above-mentioned copending patent application Ser. No. 08/181,624 filed Jan. 13, 1994.

It should be understood to those skilled in the art that each robot assembly, controllers, and camera vision tracking system requires careful calibration and configuration procedures for the infeed system to properly function. For instance, each robot assembly requires that joint positions be set and joint limits be configured to ensure that the robots avoid structural damage when enabled. Furthermore, a camera-to-robot calibration is required so that the vision system may accurately compute the positional coordinates of the needle so that the robot may move to the pick position. This procedure provides a translation matrix between the camera's field-of-view and each robot base position.

The PLC 119 is responsible for initially powering the robot controllers and robots. A robot calibration procedure may be initiated after power-up to move the robot joints to known "home" positions to synchronize the digital encoders (not shown).

The process of starting the PLC 119, robot controllers, and conveyors 45a, b and 55 is time-critical. From the robot controller perspective, when a ROBOT ENABLE signal 199 is raised by PLC 119, it begins its normal cycle by executing the Robot Control Task 152, the Vision Control Task 86, the Conveyor Indexing Control Task 181, and the Conveyor Initiation Task 190; which initiates the movement of conveyor 45a, waits approximately up to two (2) seconds, and then initiates the movement of second conveyor 45b as will be described in detail below. The PLC simultaneously raises the ROBOT ENABLE signal on the other Adept robot. Under this scenario, the PLC integrates the startup of the Bulk Feeding Device System, the Indexing Conveyors, and swaging machine with the raising of the ROBOT ENABLE signal 199. As will be explained in further detail below, when the ROBOT ENABLE signal goes low, the Adept robot halts its standard processing and responds to requests from the SCADA node.

Robot Control Task

There is a single Robot Control task associated with each Adept ®️ controller for each robot assembly 60a, b although only one is indicated as element 152 in FIG. 13. The control system software for the Robot Control task 152 manages the respective robot assembly 60a or 60b as a resource, reads a FIFO buffer 156 of identified needle locations which are produced by and input from the Vision Control Task 86, interfaces with the programmable logic controller (PLC) 119 of control system 90 for needle placement handshaking, and, initiates the indexing of the conveyor belts 45a, b.

The steady state operation of the Robot Control task 152 for each robot assembly 60a, (60b) is as follows:

First, the respective robot controller continuously polls its input FIFO 156 via data line 193 to obtain positional coordinate data for the identified needle locations on a respective translucent conveyor 45a or 45b. The data for the needle locations are provided to the FIFO buffer from the Vision Control task 86 via respective data lines 197 as will be explained in further detail below. When an acceptable (recognizable) needle position is entered into the FIFO buffer 156, the robot controller will remove the needle position from the buffer and direct the robot gripper arm 65a, (65b) to move to that location on the conveyor belt. Next, for each recognized needle, the Robot Control task 152 will signal the robot gripper 65a, (65b) to close on the barrel portion of needle 39 and to depart from the conveyor to an approach location proximate the precision conveyor 55. The robot control task then generates a NEEDLE IN GRIPPER signal 207 to the PLC as indicated and waits for a response from the PLC 119. As shown in FIG. 13, when the PLC receives a Robot task generated NEEDLE IN GRIPPER signal 207, the PLC 119 will generate a SAFE TO PLACE signal 191 for receipt by either of the robots 60a, b. The purpose of the SAFE TO PLACE signal 191 is to inform the current robot assembly 60a, b that a needle may be placed onto a precision conveyor boat 70 of conveyor 55. As a response to the receipt of the SAFE TO PLACE signal 191, the Robot Control task 152 will generate a DON'T INDEX PRECISION CONVEYOR signal 129 for receipt by the PLC 119 immediately before it places the needle on the precision conveyor 55. While this signal remains high, for e.g., at a logic "1" state, the Adept ®️ robot 60a or 60b will attempt to place a needle onto a boat 70 of precision conveyor 55. This involves initiating the engagement jaws 77, 79 of the precision conveyor engagement boat 70 to retract to allow the placement of the needle therebetween, as will be explained below. Once the movement of the robot has settled and a needle is placed, the Robot task 152 will generate a NEEDLE PLACE COMPLETE signal 206 for receipt by the PLC 119 and, the PLC will generate a suitable control signal 209 to enable the engagement jaws of the precision conveyor engagement boat 70 to engage the needle. In the preferred embodiment, the dwell time of the NEEDLE PLACE COMPLETE signal 206 is approximately 48-64 milliseconds. After activating this signal, the robot assembly 60a, b will hold the needle in place for the same time period. (48-64 msec.) Immediately thereafter, the robot will open its grippers and move back to its approach location away from the engagement boat 70. Finally, the DON'T INDEX PRECI- SION CONVEYOR signal 129 is removed indicating that it is now clear for the precision conveyor 55 to index which is performed at the command of the PLC 119.

As a safety interlock for conveyor index initiation, the Robot Control Task 152 will signal the Conveyor Indexing Control Task 181 with an internal control respective LAST PICK signals 192, 196 indicating that the robot assembly, 60a or 60b, has picked up the last needle from the current conveyor as indicated in FIG. 13. If the maximum number of needles expected per current camera field-of-view (hereinafter "FOV") is not picked from the respective current infeed conveyor belt 45a, (b), the Robot Control Task 152 will request the Conveyor Control task 181 to index that conveyor belt "early" via the INDEX CONVEYOR 1 EARLY or the INDEX CONVEYOR 2 EARLY signals 124,125 as shown in FIG. 13. Since all signals affecting the motion of the conveyors are routed through the Conveyor Control task 181, this task will generate a corresponding INDEX CONVEYOR 1 EARLY, signal 124' or INDEX CONVEYOR 2 EARLY, signal 125', for receipt by the other adept robot. If during normal operation a Robot Control Task receives either Index Conveyor 1 Early or the Index Conveyor 2 Early signal, it will flush the contents of its FIFO buffer 156 and continue as if the last needle has been picked from the conveyor.

The control software must take into account the floating 16–32 ms duration of a digital output based on the time slicing of V/V+. This will affect the calculation for minimum time required for placement in conjunction with setting and resetting the Don't Index Precision conveyor signal 129.

The Robot Control Task 152 performs error recovery on two type of errors. These errors are grouped as indexing errors and gross errors. As in all other tasks, gross errors cause the Task Manager 123 error recovery to respond and stop the Robot Control Task immediately. An indexing error occurs if a robot is waiting for a needle to be placed in its parts FIFO and both conveyor belts have not indexed within an appropriate amount of time. The Robot Control Task 150 recovers from this type of error by requesting the other robot to index early via signals INDEX CONVEYOR 1 EARLY and INDEX CONVEYOR 2 EARLY signals 124, 125 respectively. This forces both vision/robot control systems to flush the contents of its current parts FIFO and index the conveyor belts.

Conveyor Indexing Control Task

The Conveyor Indexing Control Task 181 initiates the indexing of each respective translucent indexing conveyor 45a, b and the task is initiated by the Conveyor Initiation task 190. All signals affecting the motion of the conveyors 45a, b are routed through the Conveyor Control task 181.

As shown in FIG. 13, the first step of the Conveyor Indexing Control task 181 is to check for the LAST PICK signal 192,196 internally generated from the Robot Control Task 152 and indicating that the last needle pick-up from the respective infeed translucent conveyor 45a, 45b has been completed by one of the Adept® robots 60a, b. Alternatively, the Conveyor Indexing Control task 181 awaits for the INDEX CONVEYOR EARLY (1 and 2) signals 126, 127 internally generated from the Vision Control task 86 when no needles are recognized in the current camera FOV. As a result of receiving the LAST PICK signals 192, 196 from the robot task, the Conveyor Control task will generate a corresponding INDEX CONVEYOR 1 signal 198, or, an INDEX CONVEYOR 2 signal 194, for receipt by the PLC 119. It is understood that each Adept® robot controller must request the PLC 119 to index a translucent indexing conveyor 45a (,b) after picking up the last needle from the respective conveyor. Therefor, the other Adept® robot must generate its corresponding INDEX CONVEYOR 1 (or INDEX CONVEYOR 2) signal for receipt by the PLC before it can command the current translucent conveyor 45a, (45b) to index. As a result of receiving the INDEX CONVEYOR 1 EARLY, signal 124' or INDEX CONVEYOR 2 EARLY, signal 125' from the Conveyor Control task 86 indicating that the maximum number of needles have not been picked up or that there are no or insufficient needles in the respective camera's FOV, the other Adept robot will generate a corresponding CONVEYOR 1 INDEXED EARLY signal 198', or CONVEYOR 2 INDEXED EARLY signal 194' for receipt by the Conveyor Control task 86, as shown in FIG. 13. These signals will cause the corresponding conveyor 45a (,b) to abort processing and initiate indexing of the belt.

After receipt of both INDEX CONVEYOR 1 or INDEX CONVEYOR 2 signals 198, 194 from each of the robot assemblies, the PLC 119 commands the translucent indexing conveyor 45a to index and generates a corresponding CONVEYOR 1 SETTLED signal 131 or, a CONVEYOR 2 SETTLED signal 132 for receipt by the Conveyor Control Task 86. Note that the CONVEYOR 1 SETTLED signal 131 and the CONVEYOR 2 SETTLED signal 132 are raised approximately 2 seconds after the PLC has been requested by the robot control task 152 to index conveyor 45a, (45b). The Conveyor Control Task 86 then informs the Vision Control task 86 to begin needle imaging upon receipt of internal control signals 131', 132' that correspond to the respective CONVEYOR 1 SETTLED and the CONVEYOR 2 SETTLED signals 131, 132. Once the indexing conveyor 45a (45b) has been indexed and the corresponding CONVEYOR SETTLED signal 131 (,132) has been received, the Vision Control Task 86 may begin needle recognition in the corresponding cameras's FOV. Specifically, as will be explained below, the cameras 82, 84 above conveyor 45a, b each take a snapshot of the respective field of views at respective illuminated portions 50a, 51a of the translucent conveyor and the Vision Control task 86 will control the processing of the image to make a determination of whether a recognizable needle is present each camera's field of view.

At this point, a distinction must be made between the mere presence or detection of a needle in the field of view and the presence of a "recognizable" needle. A needle may be present, but, for a variety of reasons, the Vision Task 160 may not be able to determine its positional coordinates until the camera vision parameters are changed by the execution of an auto-imaging algorithm which automatically adjusts the iris and vision system lighting parameters of each camera so that the cameras may subsequently obtain enhanced images that may be processed. During steady state, when the vision task has already "recognized" a needle in its respective field of view, the auto-imaging algorithm is not repeated. Details of the auto-imaging algorithm will be explained in detail below.

Vision Control Task

The Vision Control Task 86 controls and processes the images taken by each of the two camera assemblies 82, 84. Since the timing of the two translucent conveyors are phased, only one camera is operating at one time.

Specifically, as shown in FIG. 8, the Vision Control task 86 interfaces with each respective camera 82, 84 to identify the needle locations of recognizable needles in that camera lens's respective field of view encompassing an area located at respective illuminated platforms 50a, 51a. The Vision Task 160 then processes the positional and orientation information of the identified needle locations and writes those locations to the Robot Task FIFO 155 via data lines 197. As mentioned above, the Vision Control task is additionally responsible for initiating an early conveyor index if no needles were imaged in a camera field of view.

As described briefly above, the Vision Control task runs each time either conveyor 45a, 45b completes indexing. It is initiated to begin needle recognition upon receipt of either a CONVEYOR 1 SETTLED signal 131' or CONVEYOR 2 SETTLED signal 132' which is generated by the PLC 119 and routed through the Conveyor Control task 86 each time respective translucent indexing conveyor 45a, 45b has ceased indexing, as commanded by the Adepts. Each CONVEYOR SETTLED signal 131, 131 goes high (logic "1") approximately two (2) seconds after the PLC has been requested by the Adept® robot to index a translucent indexing conveyor. Each of the CONVEYOR SETTLED signals 1 and 2 (131, 132) remain high until the PLC 119 receives the next respective INDEX CONVEYOR 1 or 2 signal 198, 194 from the Adept robots.

The Vision Task 86 activates that camera which is associated with the conveyor settled signal. When activated, the camera 82, 84 takes a picture of the backlit areas 50a, 51a of the conveyor belt 45a, (45b). Any image obtained is preferably converted to binary image data for subsequent digital processing. The Vision Control task 86 utilizes "vision tools" to detect acceptable needles, and places the coordinates of acceptable needle pick-up points in the FIFO buffer 156 for the Robot task. An "acceptable" needle in the backlit areas is a needle that measures within the tolerances of the needle parameters that have been previously accepted during the needle changeover procedure. The needle changeover procedure is a procedure to inform the infeed system software of the type and size of the needles in the current batch to be processed and must be executed before making needle batch changes as to be discussed below. Specified needle tolerances are for the needle radius, barrel width, angular characteristics of the needle with respect to the robots, and the calculated area as computed from the needle parameters.

Auto-Imaging Algorithm

As mentioned above, if a detected needle is unrecognizable, the auto-imaging algorithm is invoked to change the camera vision parameters. Thus, after the binary image data is processed, a determination is made as to whether the needle image is of the specified radius, whether the needle image is of the specified barrel width, whether the needle image has the specified angular characteristics, and, whether the needle image area is within the specified tolerance. If any of these criteria are out of specification, then an auto-imaging algorithm is executed which functions to take a series of pictures of the same needle image at the respective camera's field of view to thereby enhance the needle image for better needle recognition by improving the vision parameters between pictures. Thus, after each of the series of pictures is taken, the auto-imaging algorithm will automatically adjust the camera's iris and vision system lighting parameters to enable the vision system to image the needles properly within the camera's field of view. For example, when adjusting the lighting of the fields of view, certain camera vision parameters such as the gain, offset, and binary threshold may be modified. The auto-imaging algorithm is executed until a needle is recognized in each camera's field of view and is not repeated until a needle changeover is executed.

Even when the cameras of the Vision Control task 160 are adjusted, needle images may still not be imaged properly. This is because each camera's field of view utilizes a backlighting source and needles that overlap, touch with each other, or, are clipped by field of view edge boundaries will not be considered for recognition. Thus, the Vision Control task will make a determination of whether the needles overlap or touch each other, and, will determine whether the needles are too close to the edge of the field of view.

After all of the possible needles are recognized, the Vision Control task will calculate the needle pick-up coordinates of the acceptable needles and place them in the Robot Control task FIFO buffer 156 to enable the robot to pick and place the acceptable needle onto the precision conveyor. In the preferred embodiment, the maximum number of needles that can be recognized during each dwell cycle of each translucent indexing conveyor is three (3). If less than this maximum or if no needles are recognized, a robot may be signalled to index the corresponding conveyor early, causing the vision system to abort its processing as described above.

Vision Task 86 is responsible for limiting the number of needle locations written to the FIFO to three, since the Robot Control Task will pick and place a needle for every needle location passed to the FIFO 156. In the preferred embodiment, the Vision Task is limited to operate for five seconds per indexing conveyor cycle.

The Vision Control Task 86 performs error recovery on three types of errors. These errors are grouped as imaging errors, processing errors, and gross errors. The gross errors cause the Task Manager error recovery to respond and stops the Vision Control Task 86 immediately. When an imaging error occurs, the Vision Control Task 86 suspends all execution on the current FOV and requests an early index of the conveyor belt by generating either INDEX CONVEYOR 1 EARLY or INDEX CONVEYOR 2 EARLY signals 126, 127 as discussed above. Receipt of these signals causes no needles to be placed in the parts FIFO and forces both vision/robot systems to pass on the current FOV of needles. If a processing error occurs, the Vision Control Task suspends all processing on the current needle and begins processing a new needle in the same FOV if another needle is available. As a result, the Vision Task does not insert the needle into the parts FIFO.

Conveyor Initiation Task

The Conveyor Initiation Task 190 functions to initiate the Conveyor Indexing Control task 181 and is started whenever the ROBOT ENABLE signal 199 is raised from the PLC 119. Once started, this task requests an INDEX INFEED CONVEYOR 1 (45a), signal 133, then waits approximately two (2) seconds, and requests an INDEX INFEED CONVEYOR 2 (45b), signal 134, as shown in FIG. 13. The task 190 is then terminated and is not restarted again until the ROBOT ENABLE signal 199 is lowered and raised again.

Task Manager

The Task Manager 123 initializes the software and hardware I/O signals, the global variables, and the vision/robot system tasks. Once the vision/robot system tasks are running, the task manager monitors the integrity and status of each task currently running and the resources that are controlled by these tasks. The status poll signals 129a–129f are indicated in FIG. 13. The resources are the robot, communication ports, and the I/O signal lines. The Task Manager reports any errors to the PLC, via the SYSTEM FAIL signal 130, and the SCADA node, via the SCADA Node Interface Task 195. The SYSTEM FAIL signal 130 is generated whenever a robot (as detected by the Task Manager) has recognized a gross error which prevents it from continuing operation. This signal is active-low and remains low until the Adept robot is reset. Thus, the PLC must lower the ROBOT ENABLE signal 199 immediately upon receiving this signal.

For gross errors occurring with the vision/robot control software, the Task Manager 123 is utilized to detect and recover from these errors by continuously polling the status and integrity of all steady-state tasks and resources during program execution. If it is determined that a gross error has occurred, the SYSTEM FAIL signal 130 will be raised to the PLC 119 and all tasks except the SCADA Node Interface Task, the Control Panel Task and the Task Manager will be stopped. A code indicating the reason for the last unrecoverable error will be available to the SCADA Node through the SCADA Node Interface Task. In some cases, an error message will be displayed in the Monitor Window of the Adept robot controller. After the SYSTEM FAIL signal is raised, the Task Manager will attempt to correct any problems detected on the robot and notify the operator through the Monitor Window. In most cases, the operator will only need to raise the ROBOT ENABLE signal again to re-set the vision/robot control software.

Control Panel Task

The Control Panel Task 88 presents a mouse controlled panel that allows an operator to access various software "debugging" utilities, to access diagnostics utilities, to control the speed of the robot, and to select new positions that the robot will move to for picking and placing needles. Also, the Control Panel Task allows the operator to stop the vision/robot system tasks from executing.

SCADA Node Interface task

The SCADA Node Interface task 195 polls the SCADA Node RS-232 interface for messages from the SCADA node. The task will act as slave to SCADA Node requests for Adept and camera set-up procedures necessitated by product changeovers. These requests are valid only when the ROBOT ENABLE signal 199 is deactivated.

Lens Control Task

The Lens Control Task 128 is initiated only when the SCADA node requests a new product to be introduced to the vision system and is executed only as an off-line process. The Lens Control Task 128 accepts the new needle parameters and adjusts the field-of-view size for both cameras to accommodate the new product size. The zoom, focus, and iris lenses are affected by this new product introduction, as well as internal vision system parameters, such as gain, binary threshold, and offset, used for imaging. Once the cameras are adjusted, the task is suspended until another new product is introduced to the vision/robot system.

Product Changeover

Prior to enabling the robots to begin the needle infeed process, a Needle Changeover procedure is invoked to inform the Vision and Robot Control tasks of the control system software of the type and size of the needles to be processed. This needle changeover procedure must be completed before making needle batch changes. If a changeover is not completed before the first needle batch run after power-up, an error message will be displayed at the FIX/DMACS (SCADA Node) screen when the robots are enabled and the robots will not run. If a changeover is not completed between different needle batch runs, the vision tasks will not identify any needle being run.

Essentially, an operator of the system enters the needle parameters in appropriate units, e.g., millimeters and degrees at the FIX/DMACS screen (not shown) of the SCADA task 195 through data lines 135. Such needle parameters for use by the Vision tasks include, the needle radius and the radius tolerance, acceptable needle angles and their tolerances, and, the needle width and the width tolerance.

In addition to inputting needle change parameters for the vision tasks, initial camera set-up parameters associated with the particular batch of needles to be processed are also input through the SCADA Node for use by the system. The software utilizes the information provided by the user via the SCADA Node to automatically adjust the lens for the correct field-of-view size, focus, and zoom parameters prior to enabling the robots.

Figure 6A:
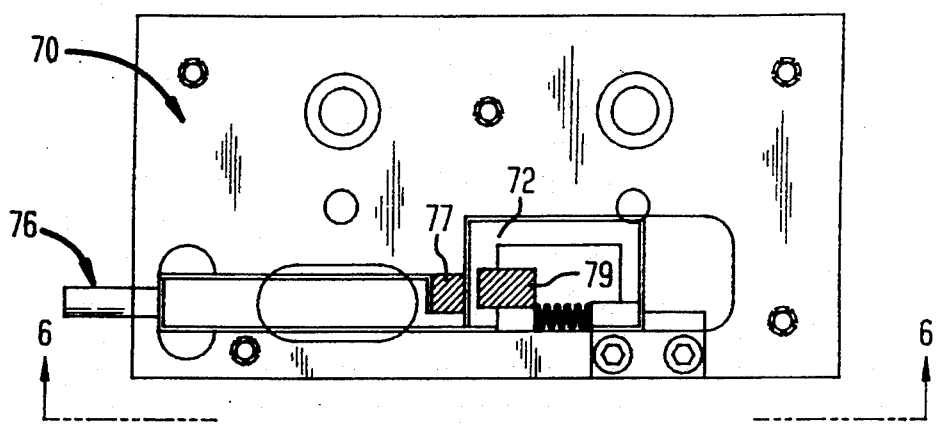
FIG. 6(a) is a detailed view of the precision conveyor boat 70 having jaws 77, 79 for engaging and retaining an oriented needle for subsequent swaging.
Figure 6B:
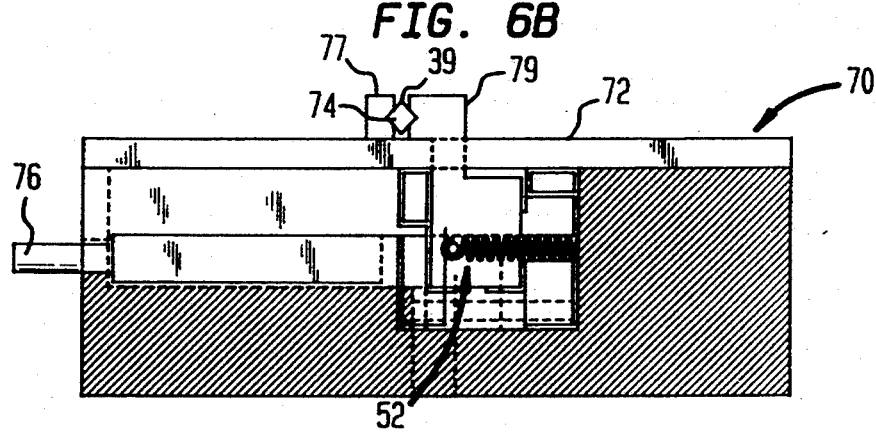
FIG. 6(b) is a detailed elevation view of the precision conveyor boat taken along line 6—6 of the boat illustrated in FIG. 6(a) showing jaws 77, 79 engaging surgical needle 39.
Figure 6C:
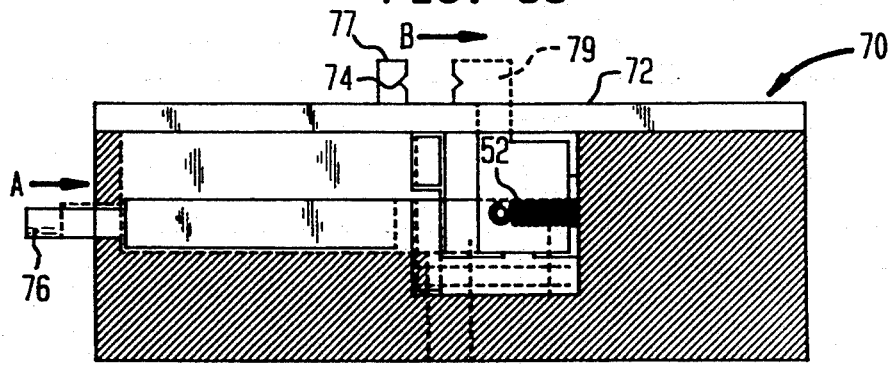
FIG. 6(c) is a detailed view of the precision conveyor boat with push rod 76 depressed to move jaw 79 apart for placement of a needle within the engagement jaws 77, 79, or, for releasing the needle from the boat for transference to the multi-axis gripper.

FIGS. 6(a)–6(c) illustrate the precision conveyor boat 70 to which each needle 39 is transferred. Each boat is preferably provided with a pair of jaws; one jaw 77 being fixedly mounted, and the second jaw 79 being slidable within pocket 72. In operation, a push rod 76 is pressed in the direction of the arrow "A" shown in FIG. 6(c) to compress spring 52 which retracts the position of the movable jaw 79 in the direction indicated by the arrow "B" to allow for placement of needle 39 within the notch 74 of both jaws. Normally, spring 52 is biased as shown in FIG. 6(b) to maintain movable jaw 79 in its engaged position for retaining a needle 39 in the notch 74. It should be understood that any type of releasable engaging mechanism may be provided for releasably retaining a needle 39 on conveyor boat 70, provided that each needle be correctly oriented on its respective boat for subsequent swaging to take place.

Figure 7:
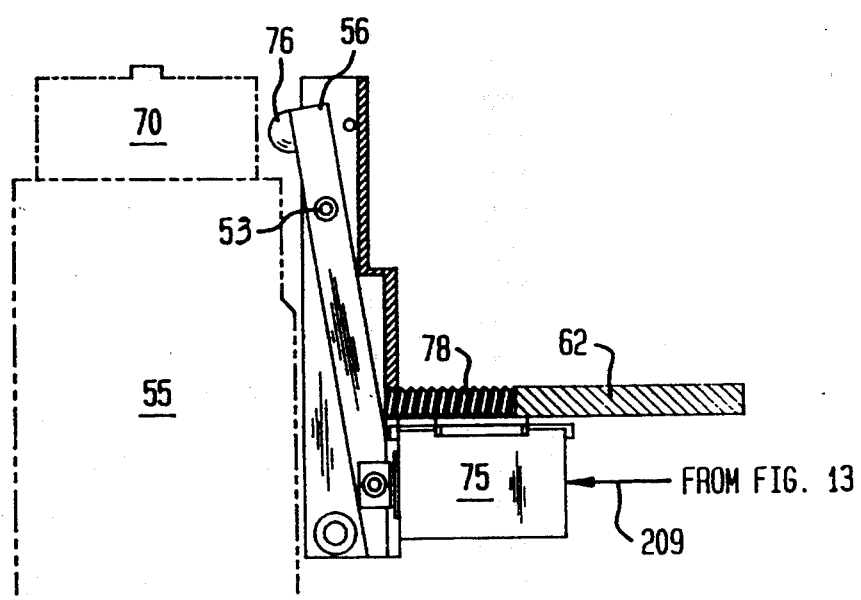
FIG. 7 is a side view of the robot load solenoid 75 that actuates the jaws 77, 79 of each of the precision conveyor boats 70.

FIG. 7 illustrates a robot load solenoid 75 that is activated by signal line 209 from the PLC 119 (FIG. 13) each time a needle 39 is being transferred to a precision conveyor boat 70. The robot load solenoid 75 may be mounted to the precision conveyor 55 by an appropriate mounting plate 62. A sensor mounted on the precision conveyor is provided to sense the proximity of a push rod 76 of a precision conveyor boat 70. At such time a conveyor boat is dwelled for transference of a needle 39 thereto, a release arm 56 of the robot load solenoid is actuated by solenoid 75 to pivot about pin 53 to depress push rod 76 and retract the movable jaw 79 to the position illustrated in FIG. 6(c). The robot arm 65 then positions the needle 39 between the jaws 77, 79 of conveyor boat 70 for engagement thereof. The release arm 56 is then retracted by spring 78 as the conveyor boat 70 moves on.

Figure 9A:
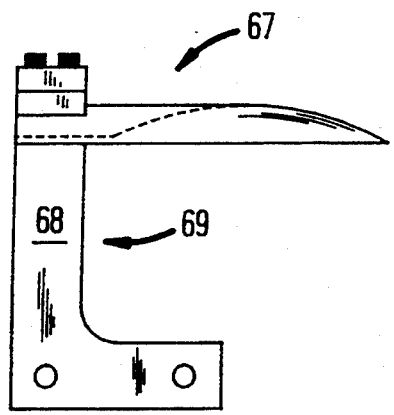
FIG. 9(a) is a side view of the needle rollover assembly 69 which ensures uniform orientation of the needle on the conveyor boat prior to automatic swaging.
Figure 9B:
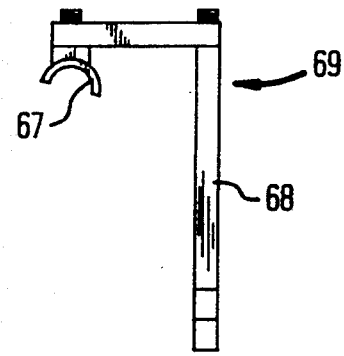
FIG. 9(b) is a front view of the needle rollover assembly 69.
Figure 10C:
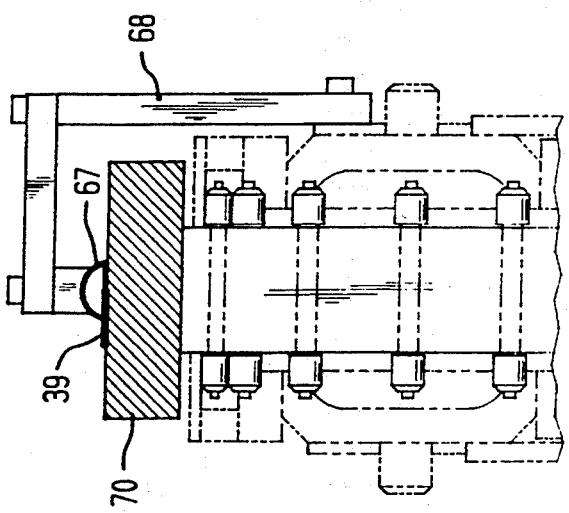
FIGS. 10(a)-10(c) is a front view illustrating the needle rollover plow 67 orienting a needle in one direction upon a boat 70 of the precision conveyor.
Figure 10B:
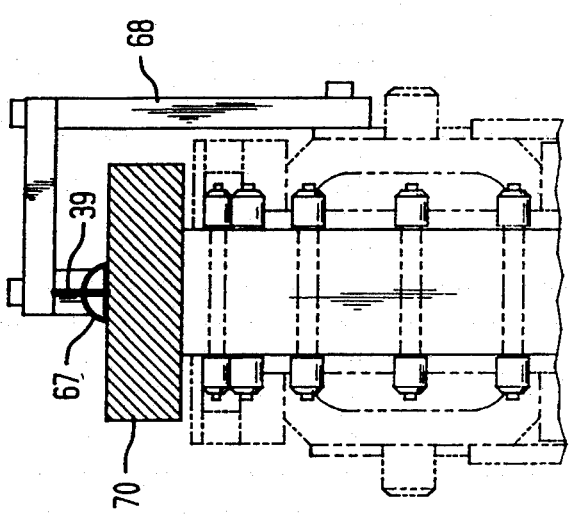
Figure 10A:
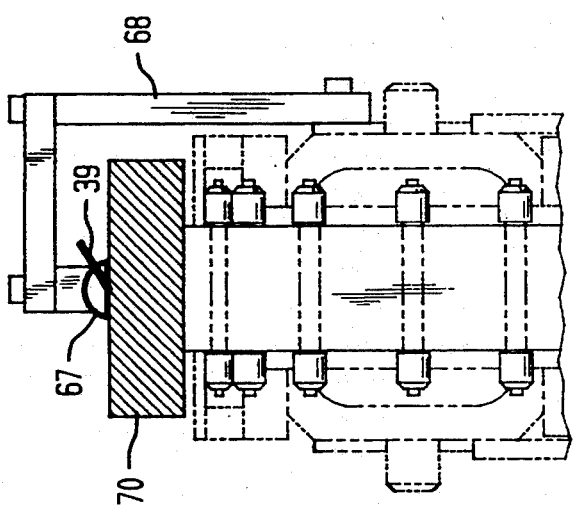

For automatic swaging to take place at the swaging station 200 it is necessary that the needle be precisely oriented within the multi-axis gripper of the rotary swage dial. Thus, the transfer of the needle 39 from the engagement jaws 77, 79 of the boat 70 to the multi-axis gripper (indicated as step 17 in FIG. 1 and explained in detail below) necessarily requires that each needle 39 be in a precisely oriented position. Efficient usage of the robotic arms and the algorithm described with respect to FIG. 13 provides that each of the robotic arms may load a needle by its barrel in a conveyor boat in one of two possible orientations. Then, to ensure that each needle is uniformly oriented for transference to the multi-axis gripper, a needle orientation device ("plow") 69 is provided as shown in FIGS. 5(b), 9(a) and 9(b) to orient each needle while engaged between jaws 77, 79 on conveyor boat 70 to a single needle orientation. The plow comprises an elongated arcuate blade 67 protruding from a mounting bracket 68 as best shown in FIGS. 9(a) and 9(b). In the preferred embodiment shown in FIG. 5(b), the plow is mounted at a fixed location along the precision conveyor 55 to enable arcuate blade 67 to scoop needle 39 positioned on the conveyor boat 70 while in forward motion. After contact is made, the arcuate portion of the needle 39 is lifted and rolls over the arcuate blade 67 of the plow 69 as shown in FIGS. 10(a) through 10(c). Provision of the plow 69 ensures that each needle conveyed to the suture swaging station is oriented in the same direction.

Figure 12A:
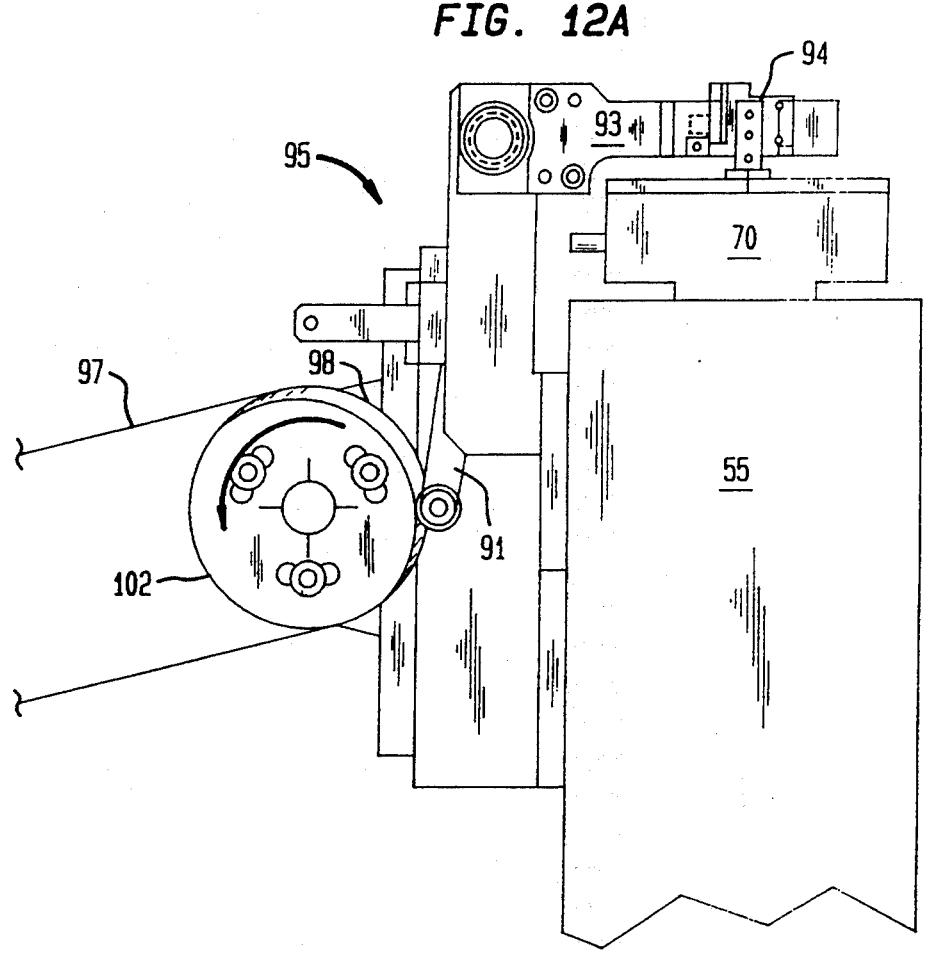
FIG. 12(a) is a side view of the needle hard stop assembly 95 for further orienting the needle 19 within the engagement jaws of conveyor boat 40.
Figure 12B:
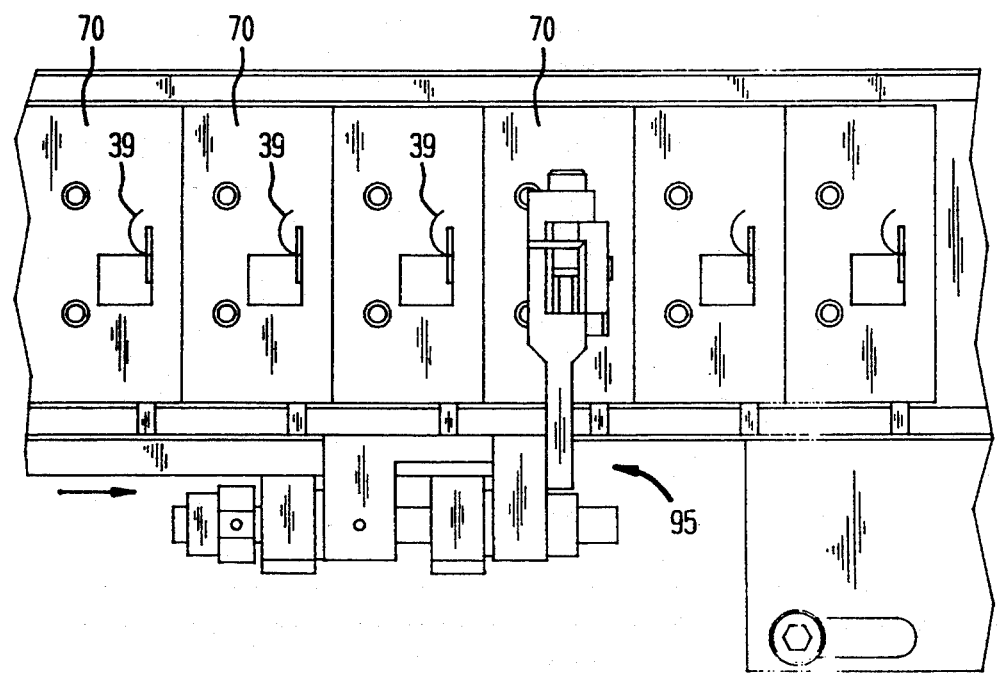
FIG. 12(b) is a top plan view of the needle hard stop assembly 95 for further orienting the needle 19 within the engagement jaws of conveyor boat 40.

Another mechanism is provided for further orienting the needle upon the precision conveyor boat is the needle hard stop assembly 95 illustrated in FIGS. 12(a) and 12(b). The hard stop assembly 95 comprises a pulley 102 operable by a drive motor (not shown) and timing belt 97 for rotating a cam 98 as shown in FIG. 12(a). Cam follower 91 is provided for actuating arm stop 93 to reciprocate from a first position above the engagement jaws 77, 79 of conveyor boat 70, to a position that enables blade 94 of arm stop 93 to bear upon the end 37 of needle 39 while the precision conveyor boat 70 is conveyed in the forward direction as indicated by the arrow in FIG. 12(b). Impeding the forward motion of the needle 39 by blade 94 forces the needle to move within engagement jaws 77, 79 of the conveyor boat 70 so that the engagement jaws 77, 79 engage the needle at a precise location, for e.g., its barrel portion. Note that the cam 98, as driven by timing belt 97, is designed so that the arm stop 93 reciprocates in a timed relation with the forward motion of the conveyor boat 70 so that each needle upon each boat 70 is further oriented. After the needle is oriented, the arm stop 93 is reciprocated to its position above the conveyor boat 70 to await the next needle for further orientation.

Figure 11:
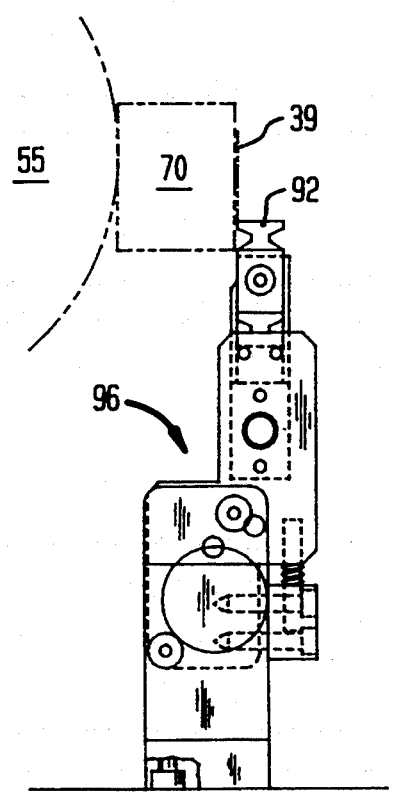
FIG. 11 is a side view of the stop assembly having blade 92 for further orienting the needle 39 on the precision conveyor boat 70 prior to transfer to the multi-axis gripper.

After the precision conveyor boat 70 is equipped with a needle 39 oriented in the proper direction in the manner described above, it is conveyed to the multi-axis gripper for subsequent transfer to the automatic swaging station 200. A needle stop assembly 96, shown in FIG. 11, is the mechanism for executing a hard stop of the needle when the associated conveyor boat has reached the end of its destination and is positioned vertically on the precision conveyor 55. The blade 92 of the hard stop assembly 96 provides a fine tuning of the orientation of the needle prior to transfer. Specifically, the blade 92 is extended upward from the hard stop assembly 96 to hold the bottom of the needle 39 and further orient the needle to within 0.001 inches of the final position required for automatic transfer to the multi-axis gripper to occur.

Rotary Swage Dial/Multi-axis Gripper

Figure 14:
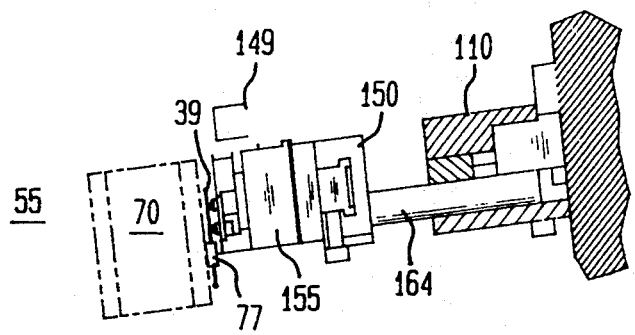
FIG. 14 illustrates the multi-axis gripper 155 receiving an oriented surgical needle 39 from a precision conveyor boat.

As indicated at step 17 in FIG. 2(a), the next step of the needle threading and swaging process 10 involves the loading of the individual precisely oriented surgical needle 39 from the precision conveyor boat 70 onto the multi-axis gripper 155. At this point, the precision conveyor boat 70 is in a vertical position as shown in FIG. 14 and the needle has been oriented by the needle hard stop assembly 96 described above. As shown in FIG. 14, the needle 39 is delivered from the engagement jaws 77, 79 of the conveyor boat 70 to the multi-axis gripper 155 at the needle sorting station to swage dial interface.

Figure 15A:
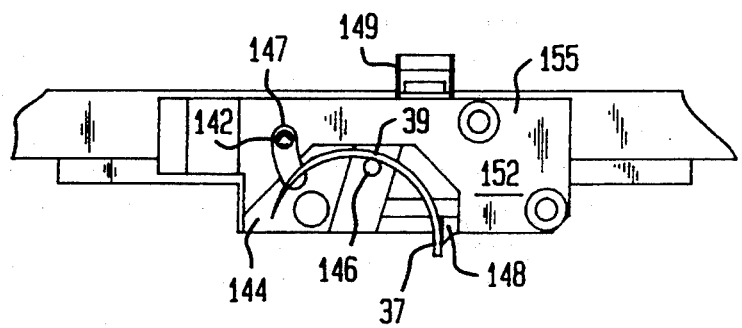
FIG. 15(a) is front face view of the multi-axis gripper 155 showing a surgical needle 39 in a relaxed engagement thereby, and additionally showing pin 142 in a retracted position.
Figure 15B:
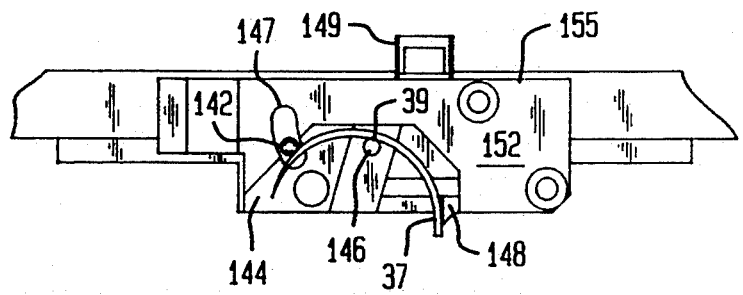
FIG. 15(b) is front face view of the multi-axis gripper 155 showing a surgical needle 39 in an engaged position therein.
Figure 15C:
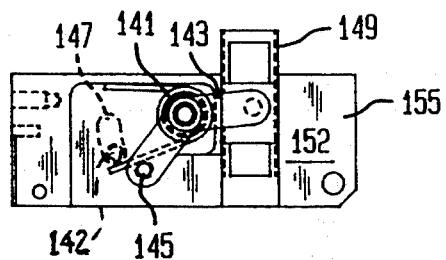
FIG. 15(c) is a partially hidden view of the actuating mechanism used to retract pin 142 within guide 147 of the multi-axis gripper 155.

In the frontal view of the multi-axis gripper as shown in FIG. 15(a), pins 142, 146, and 148 of the multi-axis gripper 155 extend perpendicularly from the gripper pin assembly 152 of the gripper to engage the arcuate portion of needle 39. To accomplish the transfer of the needle to a multi-axis gripper 155, the multi-axis gripper 155 is extended so that the vertical gripper pin assembly 152 thereof is adjacent to the needle precision conveyor boat 70 as shown in FIG. 14. The multi-axis gripper 155 is then extended from its retracted position at the station to enable pins 146 and 148 to penetrate the plane of the needle 39. Then, in the manner described above, a load solenoid or similar device depresses the pusher arm 76 of the precision conveyor boat 70 to release the needle from the engagement jaws 77, 79 of the precision conveyor boat 70 so that it falls to rest between pins 146 and 148 of the multi-axis gripper 155. A front view of the multi-axis gripper retaining the needle 39 after transfer from the precision conveyor boat 70 is illustrated in FIG. 15(a). Simultaneously therewith, as controlled by the control system computer, pin 142 is actuated from the non-engaging position to an engaging position to thereby engage the needle 39 in an oriented position as shown in FIG. 15(b). The multi-axis gripper 155 is then retracted and the swage dial assembly 150 is rotated to the swaging station to accomplish automatic swaging of the suture to the needle 39.

FIG. 13(b) illustrates pins 142 and 144 located along the outer arcuate portion of the needle, while pin 146 supports the pin at the inner arcuate portion of the needle. The barrel portion of the needle fits against a protruding stop 148 located on the gripper pin assembly 152 of the gripper 155 as shown in FIG. 15(b). The location of the stop 148 may be adjusted to accommodate the engagement of different size surgical needles. In the preferred embodiment, the gripper pin assembly 152 is replaceable with other gripper pin assemblies having the stop 148 positioned to accommodate different sized surgical needles.

The three pin needle engagement configuration shown in FIG. 15(b) ensures that the needle 39 will not be displaced when the swage dial 150 is rotating, or, when the multi-axis gripper 155 is being retracted or extended. In the preferred embodiment, pin 142 is spring loaded and is retractable within guide 147 to release its grip of needle 39 when automatic swaging and pull-testing occurs. Pin 142 is activated by depressing plunger 149, which is connected to actuating lever 143, which has pin 145 mounted thereon adjacent one leg of torsion spring 141. To retract pin 142, the plunger 149 is actuated by an appropriate push rod or solenoid arm to depress the plunger 149 and rotate lever 143 causing pin 145 to move torsion spring 141 into engagement with pin 142 to retract the same to the non-engaging and relaxed position shown in FIG. 15(a). When engaging the surgical needle 39 after the transfer, pin 142 is biased back into the needle engaging position as shown in FIG. 15(b). Note that in FIG. 15(a) and 15(b), the suture receiving end portion 37 of needle 39 extends below the gripper pin assembly 152 of the multi-axis gripper 155. This enables pick up of the needle at station 100 and placement of the suture receiving end 37 of the needle within the swage dies of the swaging assembly as will be explained below.

Figure 16:
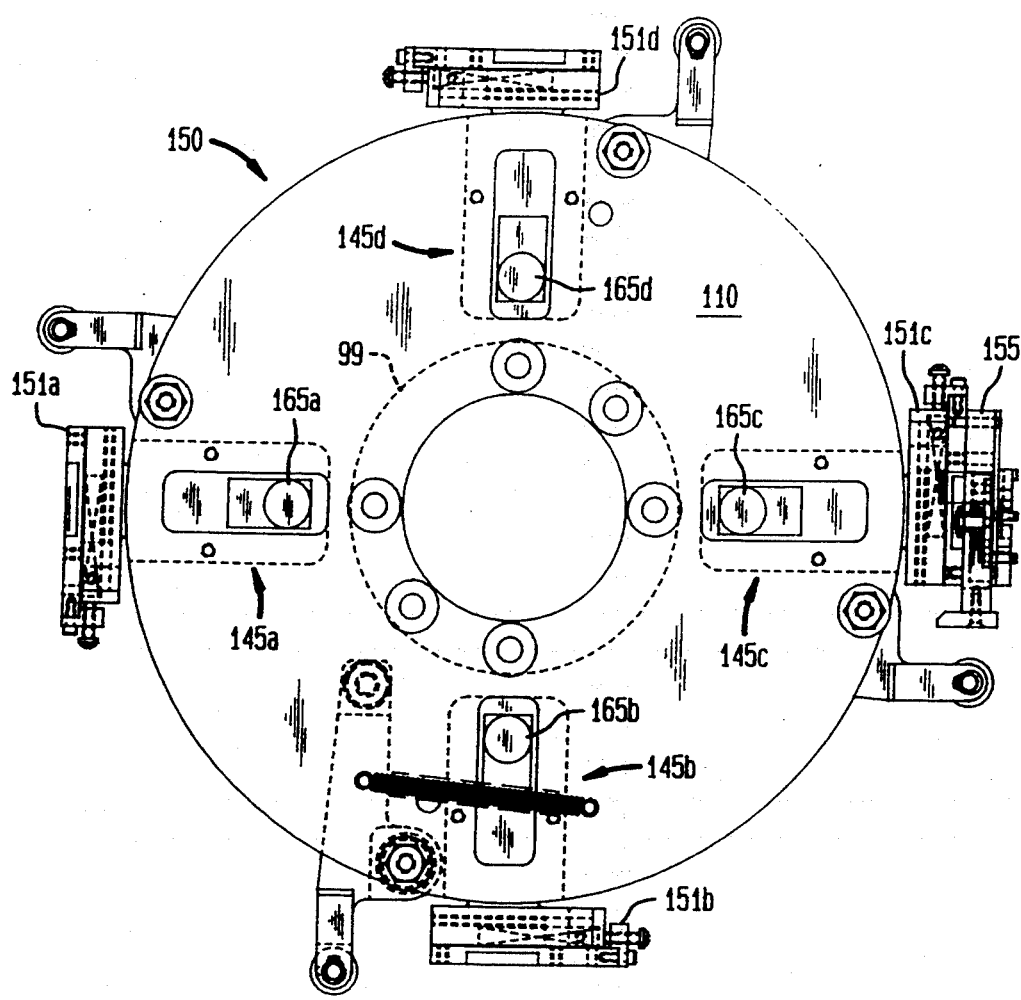
FIG. 16 is a top view of the swage dial assembly 150 comprising a swage dial plate 110 having four multi-axis gripper stations 145a, b, c, d mounted thereon.

As illustrated in FIG. 1, the rotatable swage dial assembly 150 includes four multi-axis gripper stations where simultaneous needle operations are performed. In the detailed illustration of FIG. 16, the swage dial assembly 150 includes a swage plate 110 having four multi-axis gripper stations 145a, 145b, 145c, 145d spaced equally thereon. The swage plate 110 is rotatably mounted at a central hub 99 and operable to rotate under the control of a control system computer 90. In the preferred embodiment, a reciprocating carriage is provided at each multi-axis gripper station of the swage dial assembly 150. For instance, as shown in FIG. 16, multi-axis gripper station 145a includes reciprocating carriage 151a, while station 145b includes reciprocating carriage 151b, station 145c includes reciprocating carriage 151c, and station 145d includes reciprocating carriage 151d. Mounted to each reciprocating carriage 151a, b, c, d for retractable movement therewith, are each multi-axis gripper 155, one of which is shown connected to gripper mount 150c in FIG. 16.

Figure 17A:
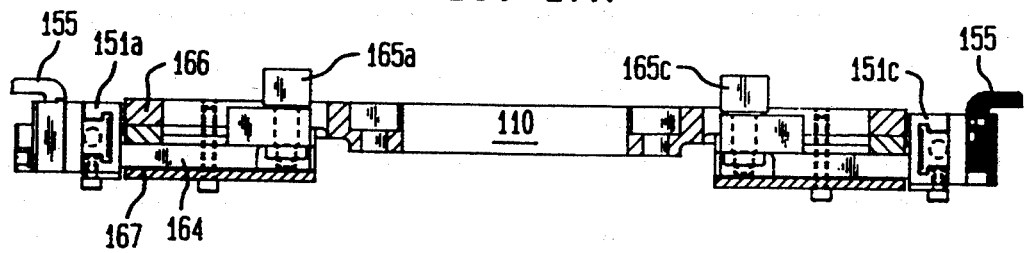
FIG. 17(a) is cross-sectional view of the four station swage dial assembly 150 showing multi-axis gripper 155 in a retracted position.
Figure 17B:
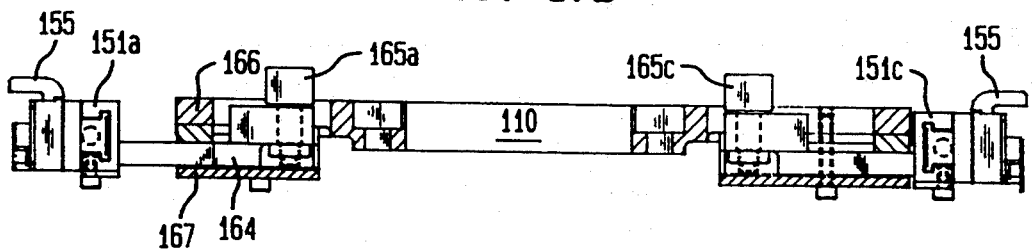
FIG. 17(b) is cross-sectional view of the four station swage dial assembly 150 showing multi-axis gripper 155 in an extended position.

As previously mentioned, each reciprocating carriage 151a, b, c, d and multi-axis gripper 155 connected thereto is movable from a retracted position to an extended position. When the gripper 155 is in the retracted position shown in FIG. 17(a), the needle 39 may be conveyed to a different station as the swage dial rotates; when the gripper 155 is in the extended position as shown in FIG. 17(b), the needle is in one of the active stations, such as the automatic swaging station. The swaging station and the automatic pull-test station are both described in further detail in respective copending patent applications Ser. No. 08/181,599; filed Jan. 13, 1994 (attorney docket No. 8937) and Ser. No. 08/181,601; filed Jan. 13, 1994 (attorney docket No. 8923) assigned to the same assignee of the present invention.

Figure 18A:
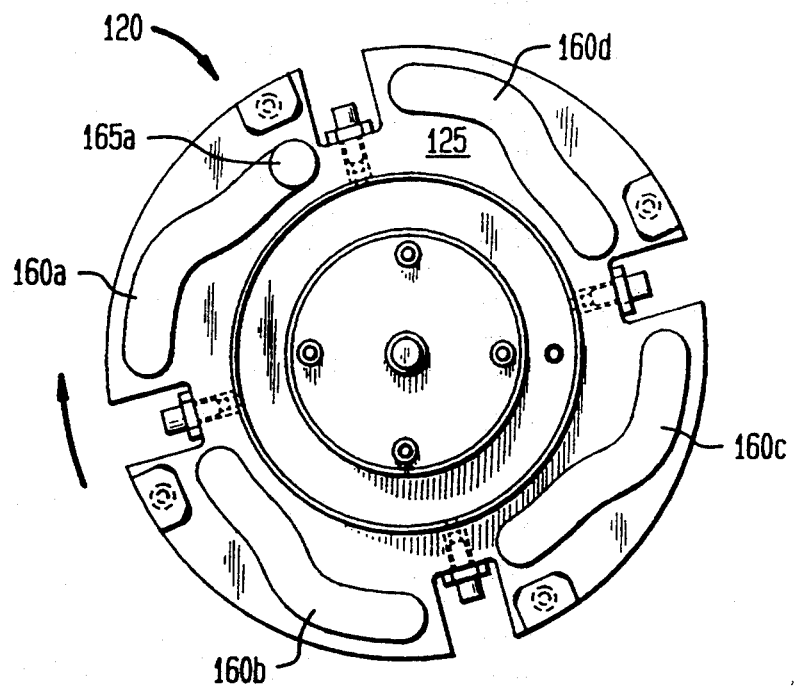
Figure 18B:
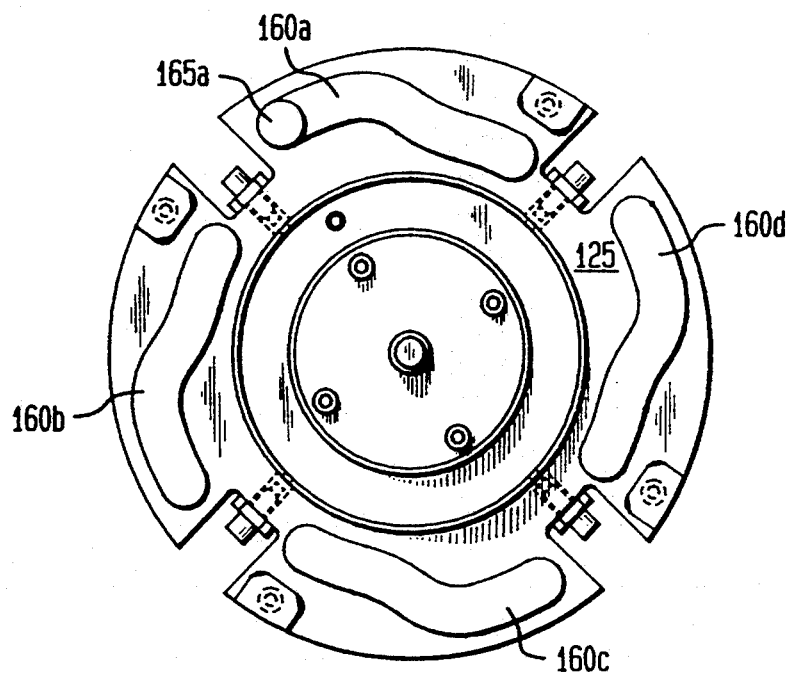
Figure 19:
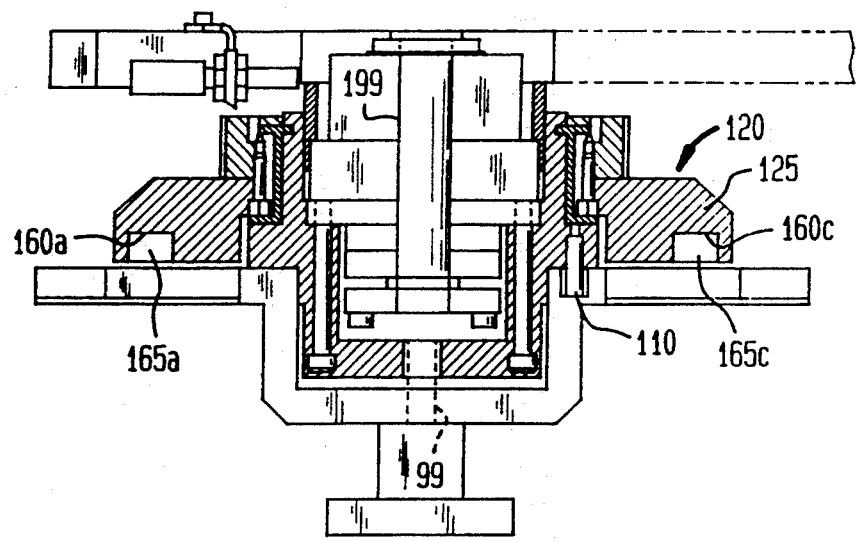
FIG. 19 is a cross-sectional view of the cam dial plate 125 mounted coaxial with the swage dial plate 110 for cooperative rotational movement thereof, and showing cam followers 165a and 165c positioned within their respective cam tracks 160a and 160c.

The process for extending each multi-axis gripper 155 for suture insertion will now be explained. As shown in FIGS. 17(a) and 17(b), each cam follower 165a (b, c, d) is mounted to a cam slide 164 at one end of the reciprocating carriage 151, and the multi-axis gripper 155 is connected to the cam slide 164 at the other end. Cam slide 164 is slidable within stationary guides 166, 167 and is adapted for reciprocal movement when the cam follower 165 is actuated. In the preferred embodiment shown in FIG. 18(a), cam follower 165 is a roller that fits within cam tracks of a rotatable cam dial assembly 120. Cam dial assembly 120 is shown in FIG. 18(a) as comprising a cam dial plate 125 having four cam tracks 160a, b, c, and 160d which correspond to a multi-axis gripper stations 145a, b, c, and 145d, respectively. Each cam follower 165 is positioned within each respective cam track at each station for movement therein. For instance, as shown in FIG. 19, cam follower 165a is positioned within cam track 160a and cam follower 165c is positioned within cam track 160c. Also in FIG. 19, cam dial 125 is positioned above swage dial 110 and mounted coaxial therewith. The cam dial 125 is rotatable about a central shaft 199 and controlled by a separate rotary indexing transmission (not shown) so that it may rotate separately from the swage dial plate 110. FIG. 18(a) shows cam follower 165a in a first retracted position within the cam track 160a. When in this position, reciprocating carriage and consequently multi-axis gripper 155 are in their retracted position as shown in FIG. 17(a) discussed above. To extend the multi-axis gripper 155 in place at its respective station, the cam dial plate 125 is rotated in the clockwise direction with respect to the swage dial plate 110, as indicated by the arrow in FIG. 18(a), for approximately 45–55 degrees, forcing cam follower 165a in its cam track 160a to move toward the periphery of the dial as shown in FIG. 18(b). Consequently, the cam slide 164, reciprocating carriage 151a, and the multi-axis gripper 155 move to the extended position as shown in FIG. 17(b) and discussed above. To move back to its retracted position, the cam dial plate 125 is rotated in the counter clockwise direction with respect to the swage dial plate 110 for approximately 45–55 degrees, forcing cam follower 165a in its respective cam track 160a to move to its retracted position (FIG. 18(a)). Consequently, the cam slide 164, reciprocating carriage 151a, and the multi-axis gripper 155 move back to the retracted position as shown in FIG. 17(a) and discussed above.

It should be understood that when cam dial plate 125 rotates with respect to swage dial 110, each multi-axis gripper 155 is either extended or retracted by its respective cam track. Thus, the system is designed so that all processes performed at each station occur simultaneously and for approximately the same duration of time when the multi-axis grippers are in their extended position, for e.g., for needle pick-up, for needle swaging, or, for needle pull-testing. The timing of the system is operated under a control system, the description of which can be found in the abovementioned copending patent application Ser. No. 08/181,607; filed Jan. 13, 1994 (attorney docket No. 8927).

When the multi-axis gripper 155 is retracted, the needle engaged thereby may then be indexed to a different station for further processing. To index the needle to another station, both swage dial plate 110 and cam dial plate 125 are rotated together for approximately 90 degrees to position the multi-axis gripper at the next station. For example, when the cam dial plate 125 and the swage dial plate 110 are simultaneously rotated 90 degrees counterclockwise in FIG. 19, the gripper 155 that had received the needle at station 100 is now indexed to station 200 for swaging a suture thereto. Similarly, after swaging, the cam dial plate 125 and the swage dial plate 110 are simultaneously rotated counterclockwise so that the armed needle at station 200 is indexed to the pull-testing station 300 for pull-testing thereof. The operations performed concurrently at each station about the swage dial increases throughput to provide an output of pull-tested armed surgical needles at a rate of approximately 60 per minute in the preferred embodiment.

Automatic Swaging Station

As previously mentioned, the automatic swaging station 200 of the needle threading and swaging system 10 is where the suture of indefinite length is drawn, cut, and inserted within the suture receiving end of a surgical needle for swaging thereof.

Figure 20:
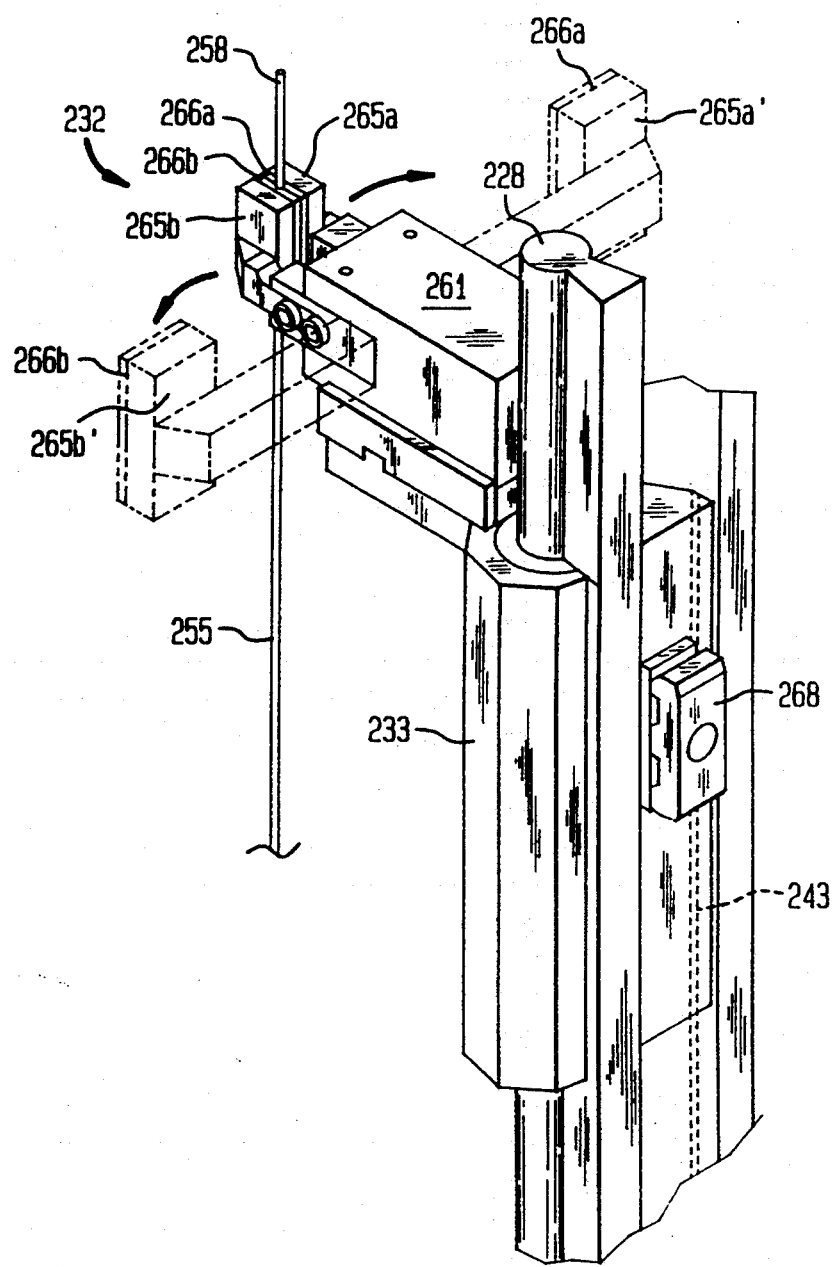
FIG. 20 is an enlarged view of a gripper assembly having gripper arms 265a, 265b shown in their closed (suture gripping) and open positions.
Figure 21:
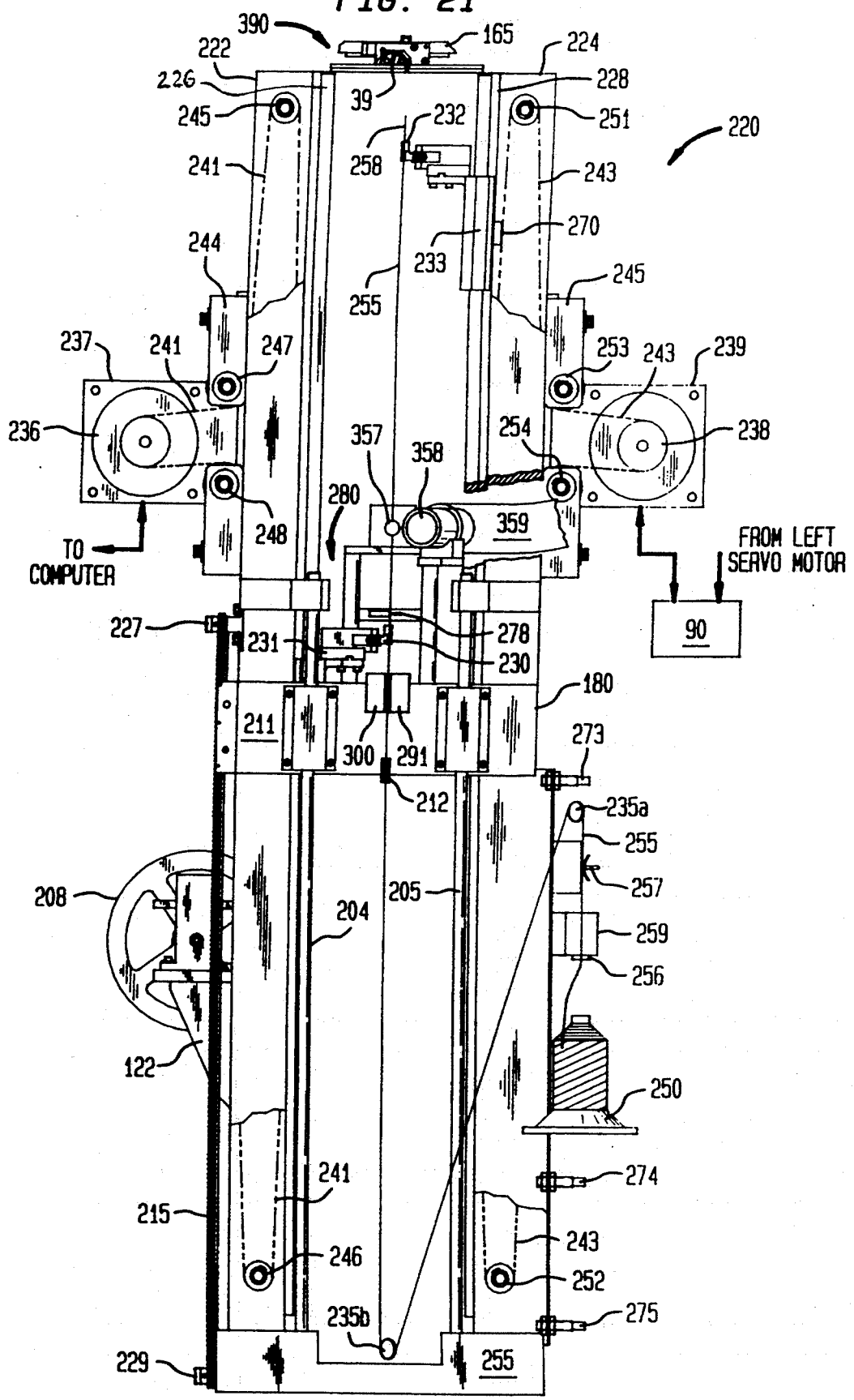
FIG. 21 is a detailed view of the automatic swaging station 200 showing servo tower 220 with cutter assembly 280 and heater assembly 290 mounted on tip and cut carrier 180, and the right gripper 232 registering the tipped end 258 of indefinite length suture strand for insertion within surgical needle 39 shown engaged by the multi-axis gripper 155.

At step 19 of FIG. 2(a) the indefinite length of suture material is loaded at one end of the payoff assembly. In the preferred embodiment, the payoff assembly is embodied as a drawing tower 20 shown in FIG. 21. The drawing tower 220 comprises left side rail 222 and right side rail 224 mounted on suitable mounting block 225 and defining a drawing bed for drawing an indefinite length of suture material along a drawing axis therebetween. Located parallel to the left and right side rails 222, 224 and suitably connected thereto are respective left guide rod 226 and right guide rod 228. The first gripper means or right gripper 232 reciprocates up and down along right guide rod 228 while the second gripper means or left gripper 230 reciprocates up and down the left guide rod 226. Each of the grippers 230, 232 grip the suture material that is fed from a spool through pulley 235b located at the bottom of the drawing tower 220, and carries the material to the upper end of the tower. The right gripper 232 is mounted on right gripper carrier 233 for vertical movement along right guide rod 228, and the left gripper 230 is mounted on left gripper carrier 231 for vertical movement along left guide rod 226 as shown in FIG. 21. FIG. 20 illustrates a gripper 232 (and 230) having a gripper arm drive 261 that is pneumatically operated to drive pair of retractable gripper arms 265a, 265b toward each other to a suture gripping position, or, away from each other to an open position. Each retractable gripper arm is provided with a non-metallic pad 266a, 266b for gripping the suture material 255 at a free end thereof when actuated to the gripping position. To release the grip of the suture, gripper arms 265a, 265b are retracted approximately 180 degrees apart in the direction indicated by the arrows of FIG. 20 to the open position. When in the open position the gripper arms 265a', 265b' do not interfere with the motion of the other vertically moving gripper as it reciprocates along the respective left or right rod, nor will it interfere with the cutter assembly 280 that cuts the strand to a predetermined length as will be explained below in view of FIG. 23. The retractable nature of the grippers and of the cutting assembly enables single drawing axis operation.

As mentioned above, each gripper carrier and gripper thereof is designed to advance vertically along the respective left and right rods. As shown in FIG. 21, the right gripper 232 and gripper carrier 233 is driven by right servo motor 238 which is mounted to the right side rail 224 by right motor mounting bracket 239. Similarly, the left gripper 230 and gripper carrier 231 is driven by left servo motor 236 which is mounted to the left side rail 222 by left motor mounting bracket 237. In the preferred embodiment, both left and right servo motors are interfaced with and controlled by a control system computer, indicated generally as numeral 90 in FIG. 21, and as explained in further detail in copending patent application Ser. No. 08/181,607, filed Jan. 13, 1994 (attorney docket No. 8927) assigned to the same assignee of the present invention. As shown in FIG. 21, right servo motor 238 drives timing belt 243 which consequently enables vertical positioning of right gripper carrier 233 along right rod 228, while the left servo motor 236 drives timing belt 241 which consequently enables vertical positioning of left gripper carrier 231 along left rod 226. As FIG. 20 illustrates, timing belt 243 is clamped to its respective gripper carrier 233 by a timing belt clamp 268 located on the back of the gripper carrier. A similar timing belt clamp (not shown) is provided on gripper carrier 231 for clamping timing belt 241 to enable vertical movement of gripper 230. FIG. 21 shows timing belt 241 engaging upper left pulley 245 and lower left pulley 246 as well as idler pulleys 247, 248 which are part of tensioner block 244 that adjusts the tension of the timing belt 241 and consequently of left gripper carrier 231. Likewise, FIG. 21 shows timing belt 243 engaging upper right pulley 251 and lower left pulley 252 as well as idler pulleys 253, 254 which are part of tensioner block 245 that adjusts the tension of the timing belt 243 and consequently of right gripper carrier 233.

FIG. 21 additionally illustrates the tip and cut carrier 180 positioned along shafts 204 and 205 which are located parallel to respective left and right rods 226, 228. Tip and cut carrier 180 provides the support for tipping assembly 290 that applies heat to a specific location of the suture material, and also provides support for the cutter assembly 280 that cuts the suture material. In the preferred embodiment, vertical movement of the tip and cut carrier 180 is accomplished by cranking handwheel 208 shown in FIG. 22(a). Other embodiments may implement a computer controlled servo motor to vertically register the tip and cut carrier 180 prior to cutting the material.

Figure 22B:
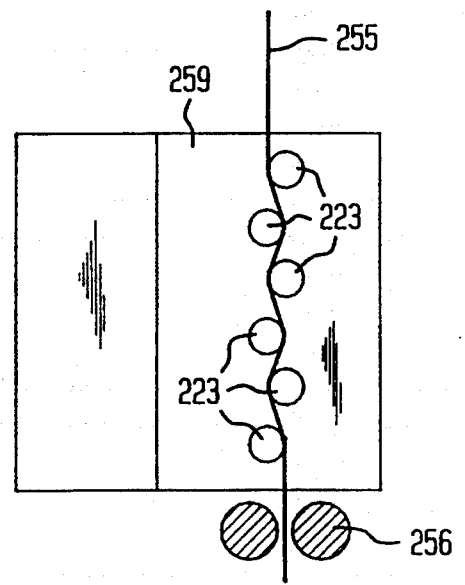
FIG. 22(b) is a detailed view of the tensioner assembly 259 for increasing or decreasing suture strand tension as desired.
Figure 22A:
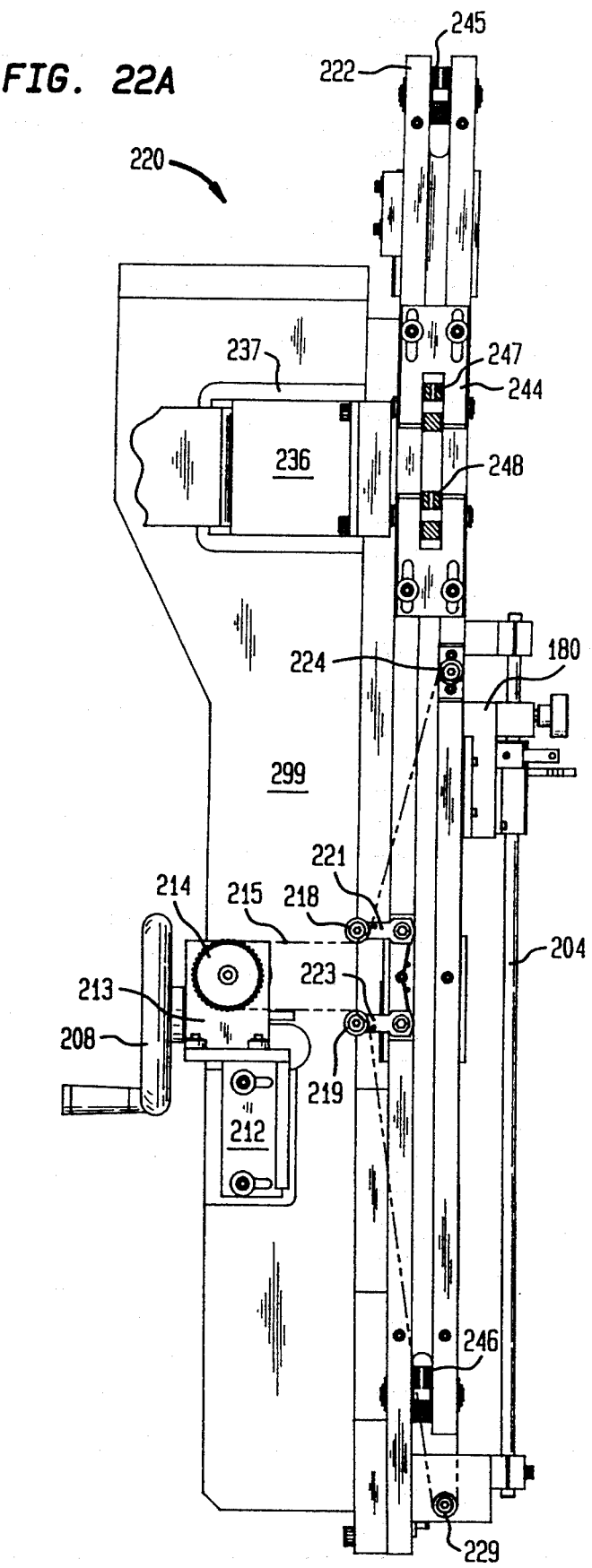
FIG. 22(a) is a detailed side view of the servo tower 220 showing the pulley assembly for moving tip and cut carrier assembly 180 of the instant invention.

As illustrated in FIG. 22(a), cranking handwheel 208 actuates a gearbox 213 that rotates chain drive sprocket 214. The gearbox 213 is mounted on a gearbox mounting bracket 122 which, in turn, is mounted to frame member 299. A cable chain 215 is engaged with chain drive sprocket 214 to actuate movement of the tip and cut carrier 180 as shown in FIG. 22(a). The cable chain 215 also engages chain idler sprockets 218 and 219 which are rotatably mounted to upper tensioner pulley bracket 221 and lower tensioner pulley bracket 223, respectively. The vertical positioning of tensioner pulley brackets 221, 223 may be adjusted to vary the slack in cable chain 215. Cable chain 215 also engages chain idler sprockets 227 and 229 which are suitably mounted on left side rail 222. As shown in FIG. 21, the back 211 of tip and cut carrier 180 is clamped to cable chain 215.

Both the stroke of the grippers 230, 232 and the positioning of the tip and cut carrier 180 along drawing tower 220 dictates the length of the material that will be cut. For instance, as shown in FIG. 21, proximity sensors 273, 274, and 275 are positioned vertically at different heights along the drawing tower 220 to enable predetermination of the length of suture material to be cut. Specifically, the locations of the proximity sensors 273, 274, and 275 sense the positioning of the tip and cut assembly 180 as controlled by handcrank 208 in order to notify the control system 90 to change the reciprocating travel of grippers 230, 232. Also as shown in FIG. 21, proximity sensor 270 is mounted at a position along the right side rail 224 to verify that right gripper 232 has reached a desired position at the upper end of the tower 220 and notify the control system 90 and servomotor 238 accordingly. Likewise, a proximity sensor (not shown) is mounted at the desired height along the left side rail 222 to verify that left gripper 230 has reached its desired position at the upper end of the drawing tower 220.

To feed the indefinite length suture material up the length of the drawing tower, the suture material 255 is first manually threaded through eyelet 256 and through optional knot detector 257 which senses any sudden change in the thickness of the suture material. Detection of a knot in suture material 255 will trigger the control system 90 to discard the cut strand of material at a subsequent operation. Additionally, the suture material may be threaded within a tensioning (or dancer) assembly 259 which comprises a plurality of vertically spaced apart cones 223 each of which may be positioned laterally to increase or decrease the tension of the suture strand 255 as shown generally in FIG. 22(b).

The suture material 255 is then advanced over pulleys 235a and 235b and further around pulley 212 which is mounted on the lower portion of tip and cut carrier 180 that is illustrated near the center of the tower as shown in FIG. 21. Note that the lower threading pulley 235b, guide pulley 212, left gripper 230 and right gripper 232 are vertically aligned so that the cutter assembly 280 will always cut horizontally across the strand of material as will be discussed in detail below.

Under the control of the control system computer 90, the right servo motor 238 is enabled to drive the lead (right) gripper vertically along right rod 228 to register the tip of the indefinite length suture strand 255 for positioning within the suture receiving opening 37 of a precisely oriented surgical needle shown engaged by the multi-axis gripper 155 at the swaging assembly 390 located at the top of the drawing tower 220 as shown in FIG. 21. To accomplish this, the lead gripper servomotor advances the lead gripper for a long stroke distance, which may range from 12 inches to 36 inches depending upon the length of said suture strand desired, but is 16.1 inches in the preferred embodiment. The long stroke moves gripper 232 from a home position just above the tip and cut carrier 180 and below the cutter assembly 280, to the position slightly below swaging assembly 390 as shown in FIG. 21.

Simultaneous with the positioning of the lead gripper 232 during the long stroke, the other servomotor, for e.g., servomotor 236, positions the bottom gripper, for e.g., left gripper 230, along left rod 226 at the home position preferably above the tip and cut carrier 180 and below the position of the cutter assembly 280 as shown in FIG. 21. It is understood that the lead gripper is gripping the material 255 at all times during the long stroke, while the bottom gripper is in its open position and not gripping. The process of advancing suture material 255 by alternating grippers at each cycle eliminates the recycle or return time for retaining the gripper to the original position. This makes faster machine speeds and hence, higher production rates possible.

To insert the tipped end 258 of the suture material within the suture receiving end 37 of surgical needle 39, the lead gripper 232 again advances the suture material 255 for a short stroke distance of about 1.9 inches, so that the tipped end 258 will advance precisely within the suture receiving opening 37 of needle 39 for a swaging operation to take place at the swaging assembly 390.

As the tipped end 258 of the suture material is advanced during the short stroke distance, a portion of the material 255 that has been heated by tipping assembly 290, (explained hereinbelow), advances vertically to a position just above the home position of the left gripper 230 and adjacent the cutter assembly 280. Then, as automatic swaging of the tipped end 258 to the surgical needle occurs, the left gripper 230 (lower gripper) is actuated to grip the material 255 at or below the tipped portion 278 i.e., the portion of the suture material heated by tipping assembly 290 as shown in FIG. 21, and the cutter assembly 280 is actuated to cut the tipped portion 278 of the suture material 255 so that the left gripper 230 is now gripping an indefinite length suture strand 255 having a tipped end 258. Simultaneous with the engagement of left or bottom gripper 230, the top or right gripper 232 is actuated to release its grip on the definite length suture material.

Heater Assembly

Figure 26:
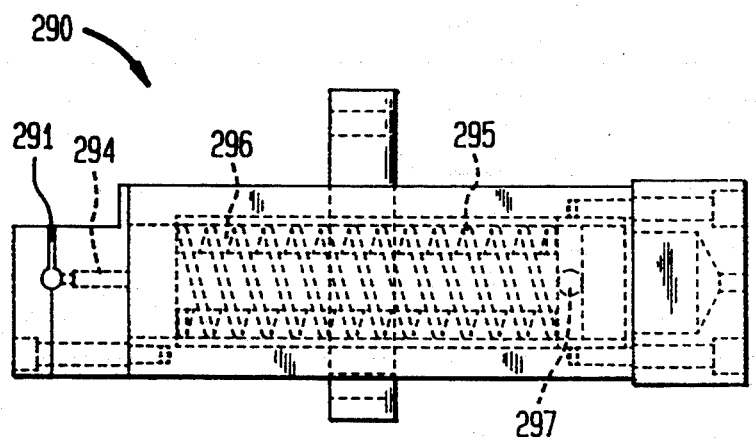
FIG. 26 is a detailed top view of the tipping assembly 290 for heating a portion of the suture material.

Immediately after advancing the long stroke distance and prior to advancing the short-stroke distance, the top gripper is temporarily halted so that a portion of the suture material 255 may be heated (tipped). Heating of the suture under tension and the subsequent cooling thereof will stiffen the material and aid in the positioning and subsequent swaging of the tip of the material within the confines of the surgical needle. The operation of the tipping assembly 290 mounted on tip and cut carrier 180 will now be explained as follows:

As shown in FIG. 26, the tipping assembly 290 is essentially an oven comprising a heat exchanger unit 295 that heats the air in the heater cavity 296. When a pulse of incoming air is provided to the heat exchanger input 297, the heated air is displaced and it provides a pulse of heated air to a vertical cylindrical cavity 291 as shown in FIG. 21. As shown in FIG. 26 the heated air is forced through horizontal orifice 294 for a predetermined duration so that the length of suture material 255 suspended in tension through vertical cavity 291 will be heated. The control system computer 90 controls the duration of the heat pulse so that the material is adequately heated and will have sufficient time to cool before the cutting operation. Preferably, the temperature of the heated pulse may vary depending upon the surface area of the strand suspended through the vertical cavity 291. Preferably, the tipping assembly 290 is positioned slightly below the bottom or left gripper 230. As mentioned above, this is required so that when the suture material 255 is advanced the short stroke distance, the tipped portion 278 of material 255 will advance a corresponding distance so that it may be cut by cutter assembly 280. This ensures that the bottom gripper, e.g., left gripper 230, will grip the material having a new tipped end 258 for the next suture draw/insert cycle.

It should be understood that various other "tipping" technologies will work depending upon the type of suture material that is being processed. For instance, when VICRYL ® and VICRYL ®-like suture materials are used, tensioning of the strand, in addition to hot air application to a strand will enable the surface thereof to be melt and recast to form a stiffened tip. The application of tension in addition to a heated, grooved, die for forming the tip diameter of VICRYL ® suture materials may also be used; however, the use of a die to form the tip diameter, requires closer control of the strand location to ensure that a tip gets into the die groove for every cycle. For wax-impregnated suture materials like silk, the application of tension only at predetermined locations, will form a stiffened portion of the suture strand at those locations. Another tipping method for use with braided suture materials, involves applying and penetrating the braid with a dilute resin material such as General Electric's VITEL ® having a high solvent content, and quick drying the applied portions with hot air while maintaining tension of the suture strand materials to form a stiffened tip thereof.

Cutter Assembly

Figure 23:
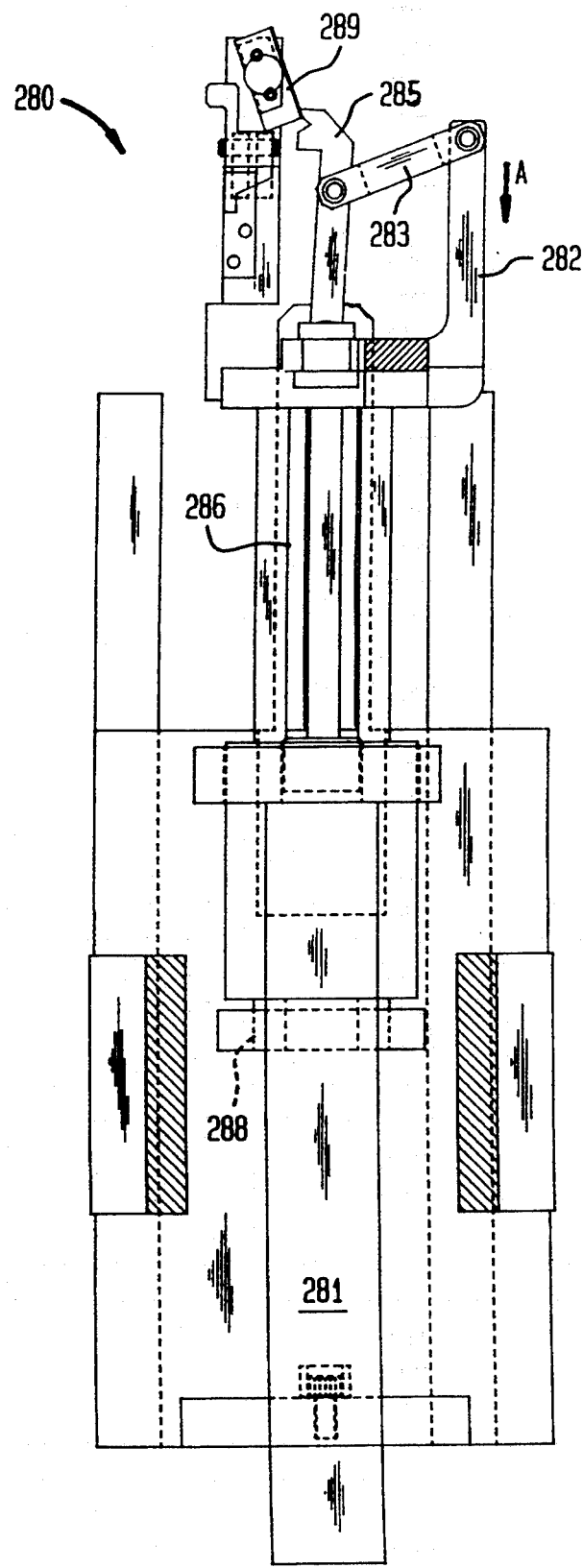
FIG. 23 is a detailed top view of the cutter assembly 200 for cutting material in the instant invention.
Figure 24:
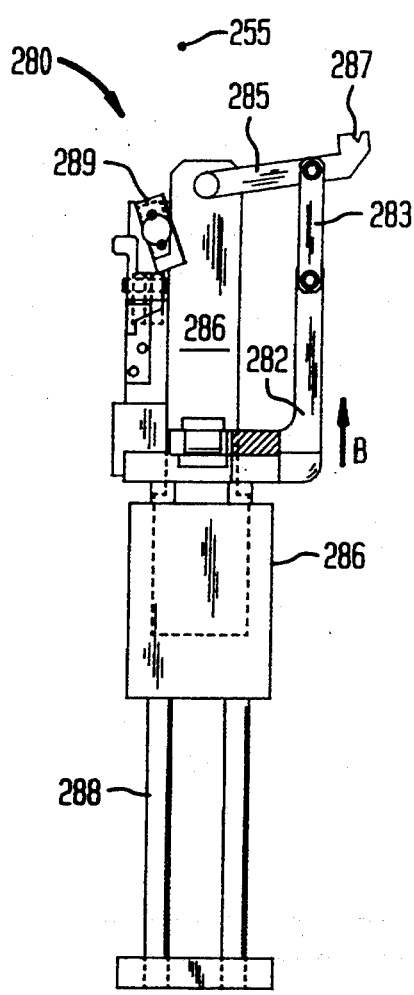
FIG. 24 is a detailed top view of the cutter assembly 280 shown in a fully retracted position.
Figure 25:
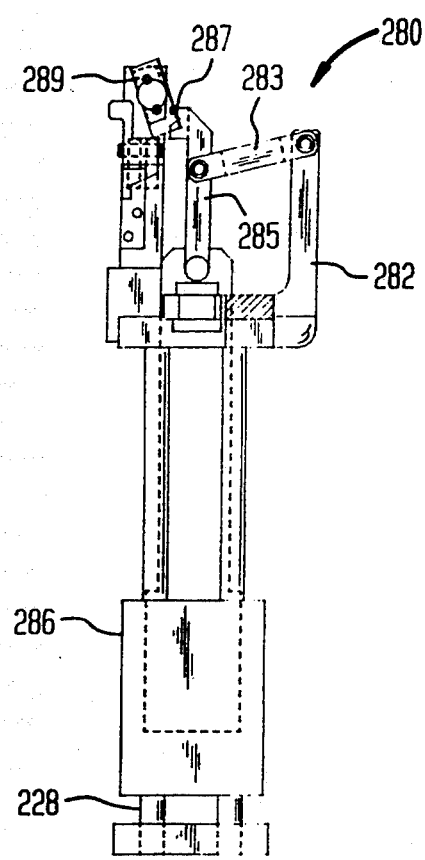
FIG. 25 is a detailed top view of the cutter assembly 280 shown in a fully extended (cutting) position.

FIGS. 23-25 illustrate in detail the cutter assembly 280 which is suitably mounted to the tip and cut assembly 180 as shown in FIG. 21. As shown in FIG. 23, the cutter assembly comprises overcenter linkage 282 having a link arm 283 pivotally connected at one end thereof. A pivotal locator arm 285 is fixedly connected to link arm 283 at a second end thereof and is illustrated in FIG. 24 as substantially transverse thereto. The other end of locator arm 285 is pivotally connected to a stationary guide mechanism 286. Note, that all pivotal linkages described herein are simple pin linkages, the actuation of which creates the dwell moment for cutting the suture strand and obviates the need for complicated cam, slots, and sliding mechanisms.

As shown in FIG. 24, the stationary guide 286 is located in a plane perpendicular to the drawing axis of the suspended strand of material 255, and is located a distance from the strand approximately equivalent to the length of locator arm 285. In addition, overcenter linkage 282, locator arm 285, and cutting blade 289 all lie in planes perpendicular to the drawing axis of the strand of material 255.

A retractable ball slide 288 is mounted on the stationary guide 286 and coupled to overcenter linkage 282 for moving the overcenter linkage and blade 289 along the stationary guide 286 in the direction indicated by arrow "A" in FIG. 23 from a cutting position to a retracted position shown in FIG. 24. As the ball slide 288 moves overcenter linkage 282 to a retracted position, the locator arm 285 is pivoted away from the strand 255 and the blade 289 is retracted. Thus, when the cutter assembly 280 is in the retracted position prior to cutting of the strand and immediately thereafter, the blade 289 and locator arm 285 do not interfere with the reciprocating motion of the grippers 232, 230 along the drawing tower 220, nor do they come in contact with the suspended strand 255. In the preferred embodiment, pneumatic air cylinder 281 enables reciprocating movement of the ball slide 288 along stationary guide 286 as shown in FIG. 23.

When cutting the strand of material 255, the retractable ball slide 288 reciprocates in the direction toward the strand 255 indicated by arrow "B" in FIG. 24 to bring the overcenter linkage 282, cutting blade 289 and locator arm 285 to the cutting position shown in FIG. 25. As the overcenter linkage 282 moves to the cutting position, the link arm 283 translates the movement of the ball slide 288 into pivotal movement of the locator arm 285. Locator arm 285 is provided with a V-shaped support notch 287 which functions to engage and position the strand of material 255 to be cut as the arm is pivoted into the cutting position. The V-shaped notch also functions to support the strand on two sides of the strand 55 while it is being horizontally cut on a third side. This enables clean, broom-free cuts especially of multi-filament suture material, which has a tendency to form a broom end when the strand is under tension and is cut by scissors, or, when the multi-filament strand is sliced and otherwise, not properly supported.

The cutting blade 289 of cutter assembly 280 is fixedly mounted to reciprocating ball slide 288 at a slight angle relative thereto and in a plane parallel with that of the locator arm 285. In the preferred embodiment, a single action by the pneumatic air cylinder 281 will enable movement of the reciprocating ball slide 288 along stationary guide 286. This consequently enables pivoting of locator arm 285 from its retracted position (FIG. 24), so that V-shaped notch 287 supports the strand 255 at two sides thereof while a third side of the strand bears upon the cutting edge of blade 289 as the blade moves towards the supported strand 255 traversing the drawing axis thereof. Thus, the strand 255 is cut in a dwell moment of the locator arm after the locator arm 285 has pivoted in the direction toward the blade arm 289 to the cutting position shown in FIG. 25. The blade 289 slices the strand of material while it is held stationary by locator arm 285 by virtue of the angled orientation of the blade with respect to the axis of reciprocation illustrated in FIGS. 24 and 25. In the preferred embodiment, the slice ratio is 1:1, with the blade 289 angled at approximately 45 degrees relative to the axis of reciprocation, so that the strand 255 is cut an amount equivalent to the distance the blade 289 traverses the drawing axis.

Swaging Assembly

The swaging operation taking place at the swaging station will now be described. FIGS. 27(a)-27(f) illustrate the multi-axis needle gripper 155 and swaging and suture alignment dies shown in various stages of the suture insertion and needle swaging sequence. This sequence, and the interaction of the dies in relation to each other, the needle, and the insertion of the suture, accomplish the insert and swage function with minimal parts and simple motions.

Figure 27A:
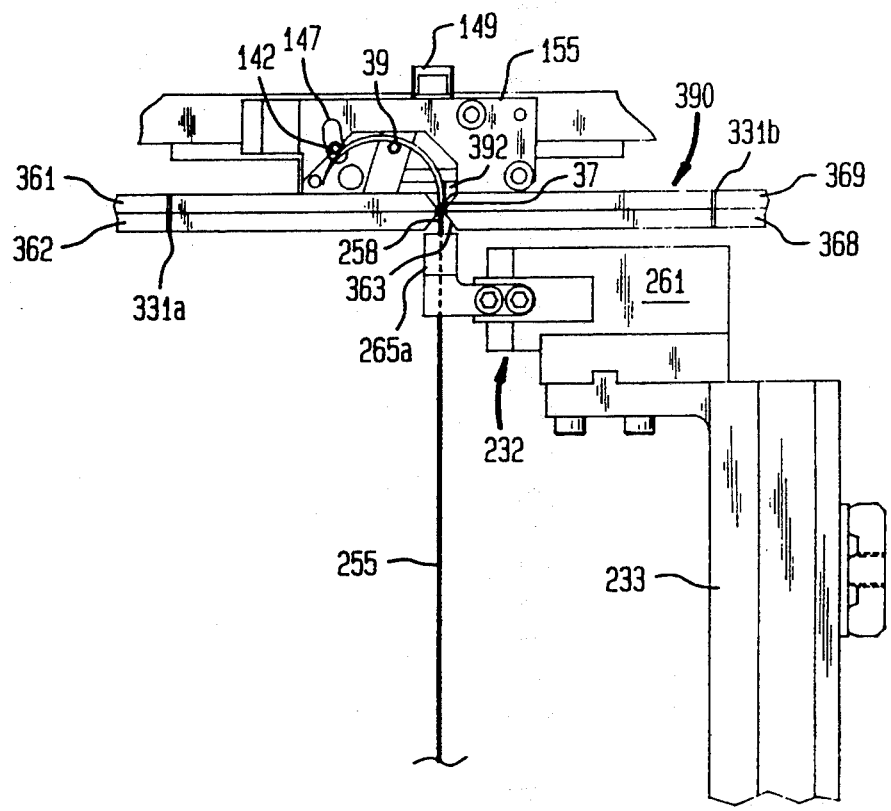
FIG. 27(a) is a detailed view of the gripper 232 shown inserting the suture tipped end 258 within the confines of the suture receiving opening of the surgical needle.
Figure 27B:
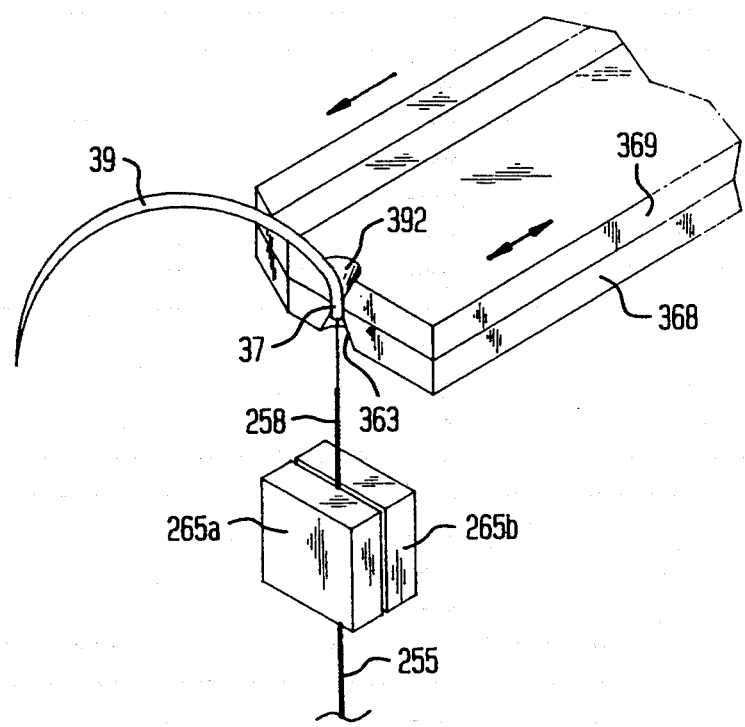
Figure 28A:
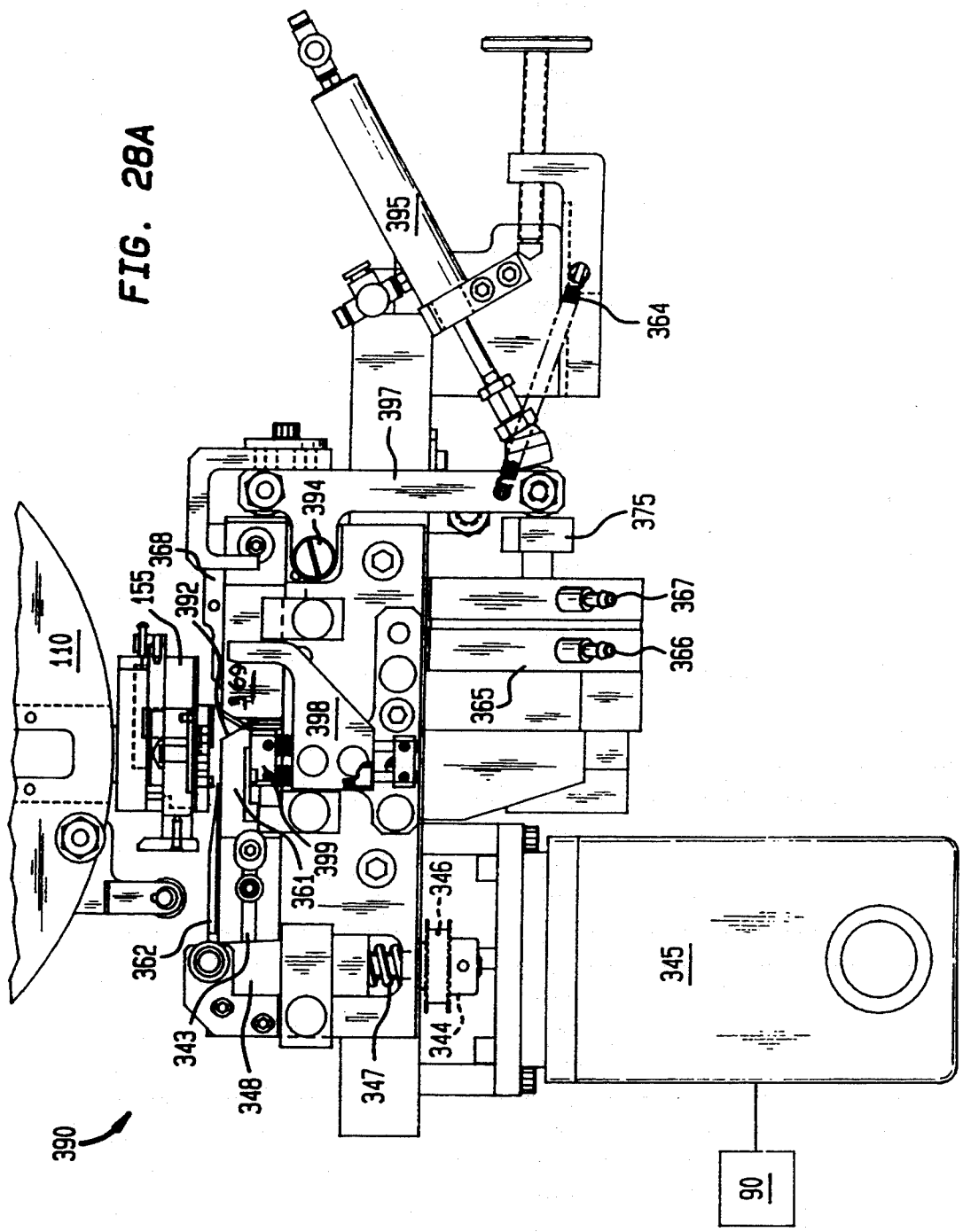
FIG. 28(a) is a top view of the swage assembly 390 of the instant invention.
Figure 29A:
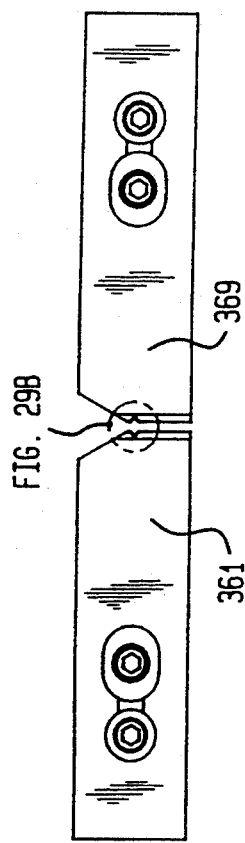
FIG. 29(a) is a detailed top view of the swage dies 361, 369 of the swaging assembly showing the recesses 321, 322 formed in the swage die opening 392 located therebetween.
Figure 29B:
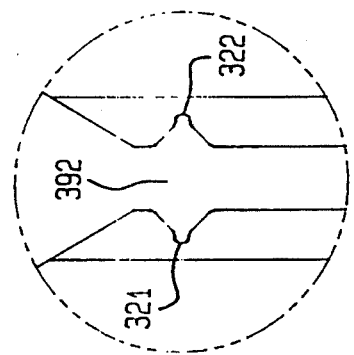
FIG. 29(b) is an enlarged view of the swage die opening shown encircled in FIG. 29(a).

After conveying the needle to swaging assembly 390 shown in FIGS. 27(a) and 28(a), the multi-axis gripper 155 is radially extended from the swage dial in the manner described above to position the suture receiving end 37 of needle 39 between the funnel shaped die opening formed at the ends of two swage dies 361, 369 as shown in FIG. 27(a) and the partial perspective view of FIG. 27(b). As will be explained, swage die 361 is fixed in position and swage die 369 is movable laterally toward the fixed swage die 361, as indicated by the arrow, to accomplish swaging of the suture receiving end of a needle placed therebetween. A funnel shaped die opening 392 having an exit diameter slightly larger than the diameter of the suture receiving end 37 of the needle is formed when the two swage dies 361,363 are positioned adjacent each other as shown in FIGS. 27(e) through 27(f). In the preferred embodiment shown in FIGS. 29(a) and 29(b), the ends of each of the swage dies 361, 369 are provided with recesses 321, 322 respectively, so that the metal deformation that occurs as a result of the swaging of the needle 39, does not result in metal flash or spurs at the suture receiving end 37 of the needle. Note that different sets of swage dies may be provided, depending upon the size (diameters) of the needles and sutures to be swaged.

To precisely position the suture receiving end 37 of needle 39 between the swage die opening 392 formed at the ends of two swaging dies 361, 369, the movable swage die 369 is temporarily moved apart. In the illustration of the swaging assembly 390 shown in FIG. 28(a), swage die 369 is moved apart from the fixed swage die 361 by actuating air cylinder 395 to provide a force upon cylinder rod 393 to enable swage die operating lever 397 to pivot about screw 394 and pull moveable swage die 368 a predetermined distance away from the fixed swage die 361. In the preferred embodiment, lever 397 is biased by spring 364 so that the movable swage die 369 will return toward the fixed swage die by the spring restoring force when the pressure provided by the air cylinder 395 is terminated.

Figure 27C:
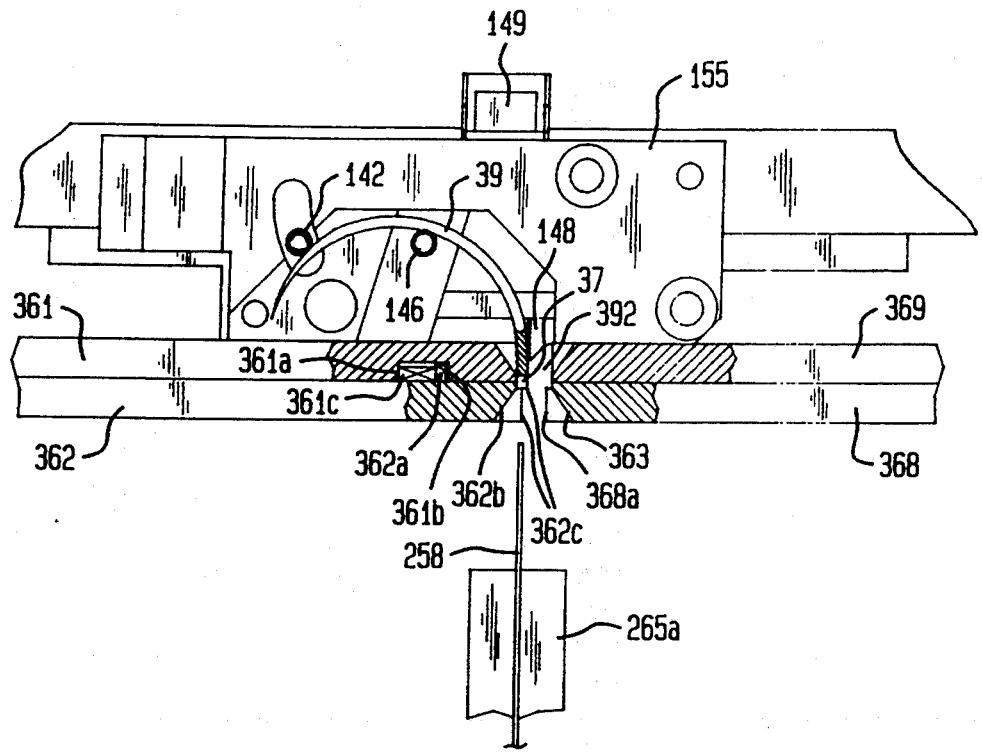

FIG. 27(c) shows die 361 in its fixed position, and moveable die 369 in its spaced apart position prior to receiving the surgical needle 39 presented by multi-axis gripper 155. Suture alignment die 362, containing suture guide funnel half 362b, is positioned under swage die 361, and free to slide laterally within limits. Alignment die 362 has a tang 362a that protrudes into cavity 361a formed within swage die 420. Compression spring 361c bears against the back wall of cavity 361a and tang 362a such that funnel die 362 slides forward until it is constrained by cavity wall 361b. In this position, it is forward of the center axis defined by the suture receiving end of the needle, and serves as a shelf 362c that helps assure suture receiving end 37 of needle 39 is in position for swaging. In this stage of the cycle, the parts are not positioned for suture insertion, and suture clamp 265a gripping suture 255 and stiffened end 258, are in dwell. Suture alignment die 368, containing funnel half 363, is fastened to swage die 369 by suitable fastening means, described in detail below, and travels with it to the open position shown.

Figure 27D:
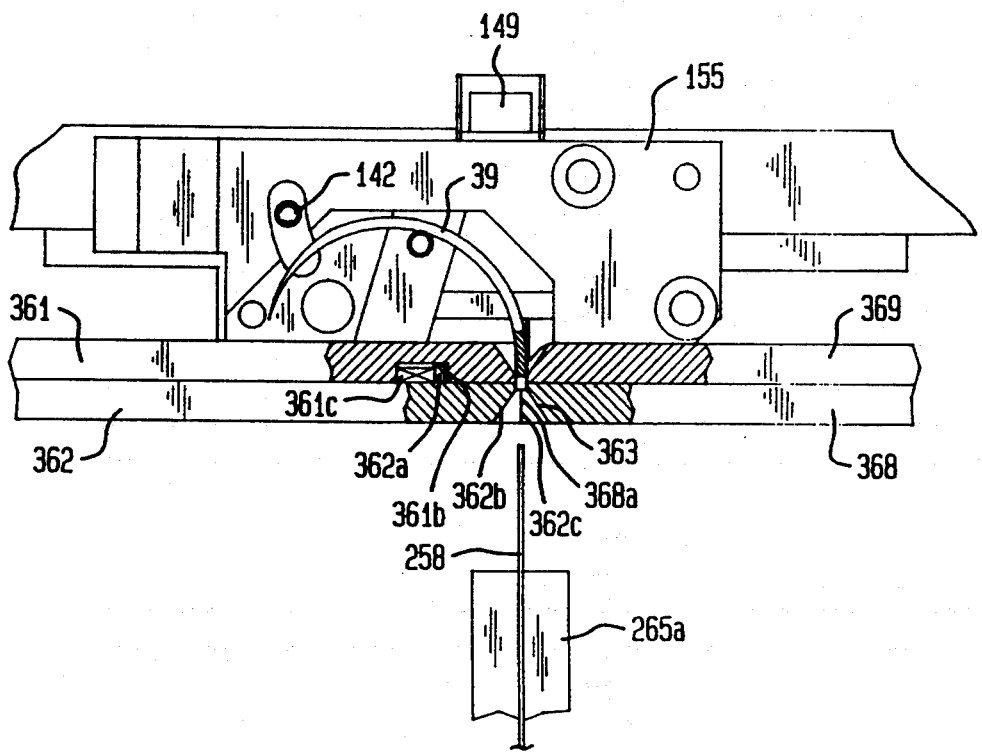

While the swage dies are apart, the multi-axis gripper 155 is extended to position the suture receiving end 37 of needle 39 within the opening 392 as shown in FIG. 27(c) and FIG. 28(a). After positioning the suture receiving opening 37 of needle 39 at the swage die opening 392, the swage die 369, and suture alignment die 368, are moved toward needle 39 with the resilient spring force present in spring 364 (FIG. 28(a)) that is sufficient to enable the die 369 to grip and locate the suture receiving end 37 precisely against fixed swage die 361 without deforming the cavity of the suture receiving opening 37 formed therein. Concurrently, needle retaining pin 142 in multi-axis gripper 155 is raised by downward external force on plunger 149, as described above, thereby releasing the needle so that its position is determined by the grip of swaging dies 361 and 369. The motion of dies 368 and 369 cause the face 368a of suture alignment die 368 to come in contact with the corresponding face 362c of suture alignment die 362. The resilient force causing this motion is forceful enough to compress spring 361c, and move funnel die 362 to the left, such that tang 362a is no longer in contact with cavity wall 361b. Dimensioning of dies 369 and 368 is such that this motion results in the formation of two funnel halves 362b and 363 defining a smooth conical shape that is coaxial with the suture receiving end 37 of needle 39. FIG. 27(d) shows the suture receiving end 37 being gripped by the swage dies 361, 369 prior to suture insertion. Note that the exit diameter of the conically shaped funnel guide formed of funnel halves 362b and 363 is preferably equal to or greater than the diameter of the suture tipped end 258 and smaller than the diameter of the suture receiving end 37 of the needle 39, as shown in FIG. 27(e), so that the tipped end 258 of the suture strand may be easily inserted therein.

FIG. 27(e) shows suture gripper 265a moved vertically to the insertion position, which causes stiffened suture end 258 to enter funnel 362b and 363, and be guided into the suture receiving cavity 37 of needle 39 axially aligned therewith. Once the strand is inserted into the suture receiving end 37 of the needle (step 27) as discussed above, the automatic swaging of the suture receiving cavity occurs. In the preferred embodiment of the swaging assembly 390 shown in FIG. 28(a), a pneumatic air cylinder 365 provides air pressure to actuate cam 375 that bears on lever 397 to thrust movable swage die 369 toward the fixed swage die to accomplish the swaging of the suture receiving end of the needle placed therebetween. Air pressure is supplied to the swage cylinder 365 via ports 366, 367 under the control of the control system computer 90.

FIG. 27(f) shows the completed swage stroke. The swage die 369 has been driven to a fixed stop by the swage cylinder, which exerted sufficient force to deform the suture receiving end 37 of needle 39. As deformation takes place, suture alignment die 368 further displaces funnel die 362, causing additional compression of spring 361c. In the preferred embodiment, the moveable swage die 369 comes to an automatic stop by a swage stop mechanism herein described.

Figure 28B:
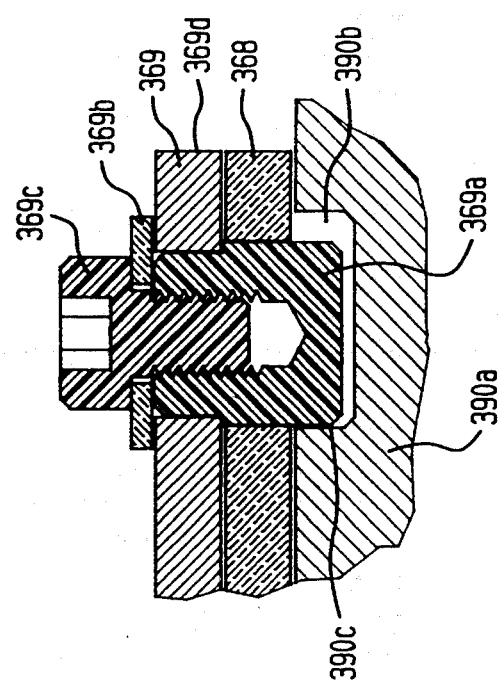
FIG. 28(b) is a detailed view of the swage stop mechanism for the swage assembly 390.

As shown in FIG. 28(b), movable swage die 369 and suture alignment die 368 are mechanically held coincident to each other by shouldered post 369a, the smaller diameter of which is a light press fit into the mating hold in die 369. Cap screw 369c, with washer 369b retain the post in die 369. The larger diameter of post 369a, below die 369, extends through a light press fit hole in funnel die 368, so that the right hand swage and funnel dies are linked to move together laterally during the swaging cycle. The lower portion of shouldered post 369a extends through funnel die 368, into groove 390b, which is cross milled into swage assembly frame 390a. When the swage stroke is performed, the swage cylinder drives this die assembly to the left until it is positively stopped by the lower portion of post 369a striking wall 390c of groove 390b. This stalls air cylinder 365, so that the stroke of the moveable right hand die assembly shown is always the same for repeating cycles of the machine.

In an alternative embodiment, both swage dies 361, 369 may be movable towards each other to accomplish swaging. Furthermore, an adjustable swage stop mechanism for changing the swage stroke distance of one of the movable dies may be provided to further control the swaging pressure applied to the suture receiving opening and obviate the need for a fine-tune positioning adjustment for a fixed swage die.

As shown in the top view of FIG. 28(a), a needle fence assembly 398 is provided to ensure that the needle 39 does not tip or become misaligned when the end 37 of the relaxed needle is positioned between the swage dies. The needle fence assembly 398 comprises a needle fence plate 399 whose distance from the tapered swage die opening 392 is adjustable depending upon the size of the surgical needle to be swaged.

In the preferred embodiment, the degree of swage compression imparted on the needle, and resulting strength of grip by the needle on the suture, is adjusted by precise positioning of the fixed die 361. As shown in FIG. 28(a), servomotor 345 drives pulley 344 via timing belt 461, which rotates the swage adjust screw 347. The pitch of the swage adjust screw 347 is selected to move sliding wedge 348 a small distance. The swage die 361 has a complementary ramp angle 343 at the opposite end which bears on the wedge 348 to retract or advance the position of the swage die 361 a precise distance proportional to the movement of the sliding wedge. Thus, the rotation of the swage adjust screw 347 and motion of the sliding wedge 348, results in transverse movement of the swage die 361 to thereby finely adjust its fixed position. For example, when a larger suture is to be swaged to a needle, the position of the fixed die 361 may be moved further away from the suture drawing axis so that less swaging pressure is applied to the needle when the movable swage die 369 is thrust towards the fixed die to a stop. In the preferred embodiment shown in FIG. 28(a), the control system computer 90 will send the appropriate signals to automatically direct the servomotor 345 to adjust the position of the swage adjust screw 347, and hence, the position of the fixed die 361, in accordance with the pull-out test values of the needle-suture bond as measured by automatic pull-test system as explained in further detail below. Specifically, appropriate control signals may be generated to direct the servomotor 345 to adjust the rotational position of the swage adjust screw 347 in accordance with stored statistical results of the pull-testing occurring at the pull-test station. Automatic pull-testing of the armed needle is desirable to ensure that the upstream swaging dies are optimally positioned to avoid over-swaging the needle-suture bond and hence, preventing the likelihood of clip-off, and, to avoid under-swaging the needle-suture bond to prevent the chance of pull-out.

Immediately after the short stroke of the right or top gripper 232, the left gripper 230 secures the suture strand, and the suture material 255 is cut by the cutter assembly 280 in the manner described above and as indicated in step 30 in FIG. 2(b). As shown in FIG. 22, the cutter assembly 280 is positioned slightly above the left gripper 230 so that the indefinite length suture strand 255 will be gripped when the swaged strand is cut. Thus, the left gripper 230 is now gripping the suture material 255 with a tipped end 258 and it now becomes the lead gripper.

In the preferred embodiment shown in FIG. 22, a vacuum air flow is energized to pull the strand of material 255 toward the nylon screen 357 to facilitate the cutting of the material thereof. After cutting of the indefinite length suture material 255, the tail end of the length of suture material that had been swaged to the surgical needle is sucked into a large vacuum pipe 358, that is connected to a vacuum assembly (not shown) by vacuum hose 359 as shown in FIG. 22. The vacuum created in vacuum pipe 358 exerts a mild tension in the strand of material to keep the tail end from entanglement or coming into contact with the machinery. However, it is mild enough to allow the strand to be pulled out of the pipe 275 as the armed needle is indexed for further downstream processes.

After swaging of the needle, the movable die 369 is again retracted by air cylinder 365 and the pin 142 of the multi-axis gripper 155 is actuated to engage the armed needle in the manner described above. Subsequently, the multi-axis gripper 155 is retracted (step 30) to its position along the swage dial 150 for subsequent indexing to the pull-test station 300 for further processing (step 31).

The cycle continues at the swaging station with the new lead gripper vertically drawing the material 255 along the height of the drawing tower 220 to position the next strand to be cut for insertion within the surgical needle. The process of advancing suture material 255 by alternating grippers at each cycle eliminates the recycle or return time for retaining the gripper to the original position.

Automatic Pull-test Station

Figure 30:
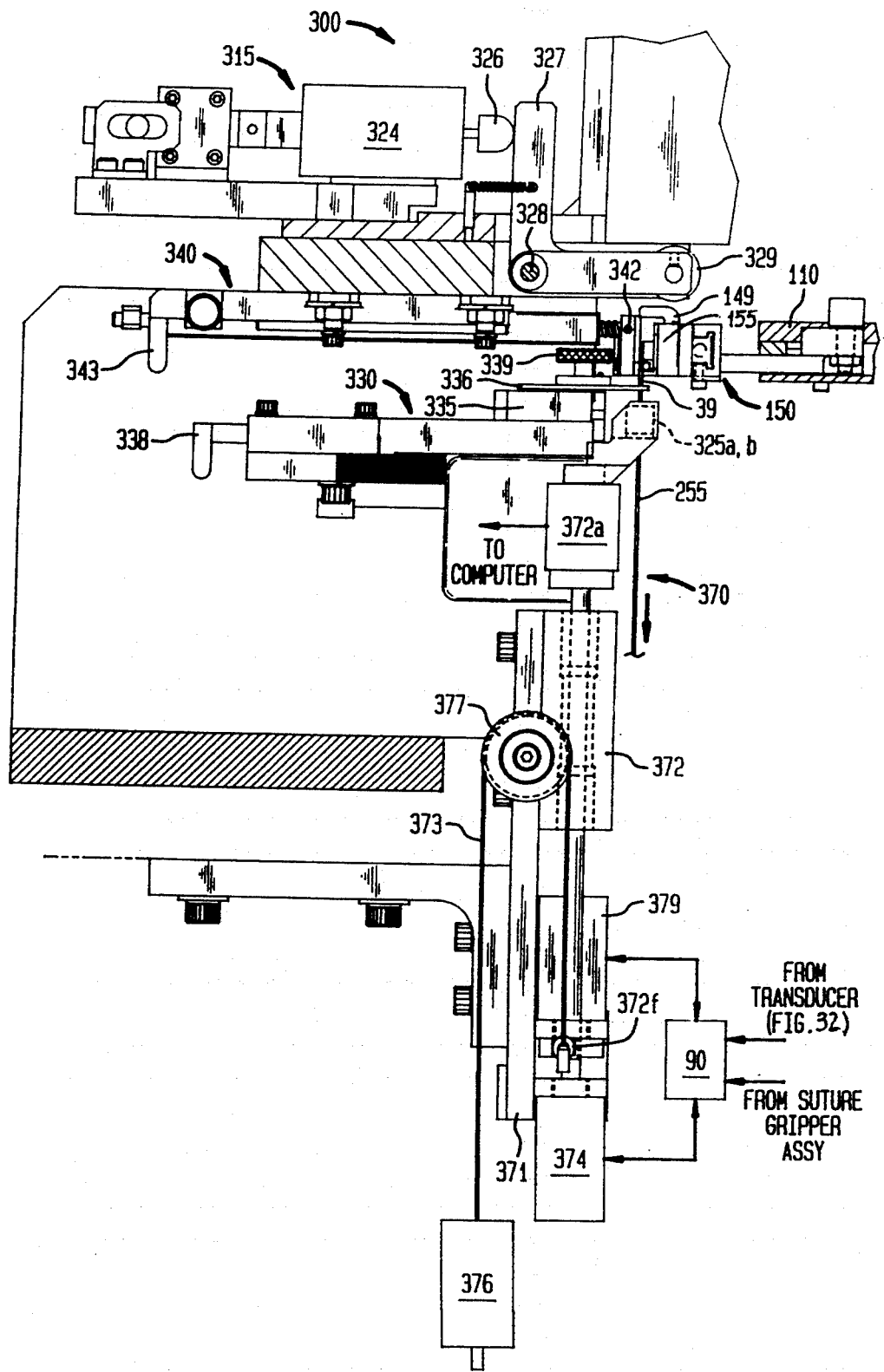
FIG. 30 is an assembly drawing of the automatic pull-test station 300 of the instant invention.
Figure 31A:
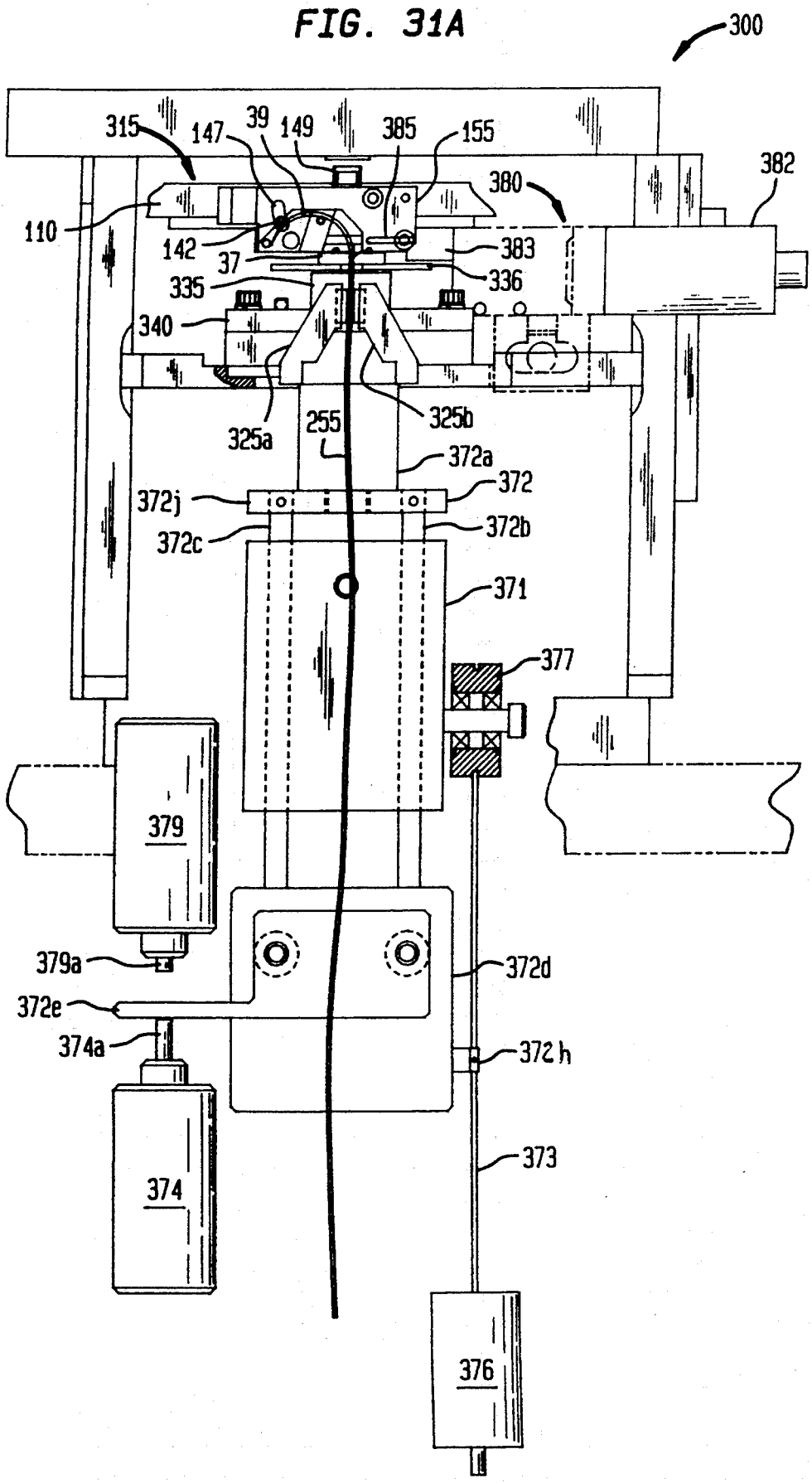
FIG. 31(a) is a front view of the automatic pull-test station 300 of the instant invention with the needle fence assembly 340 partially removed.
Figure 31B:
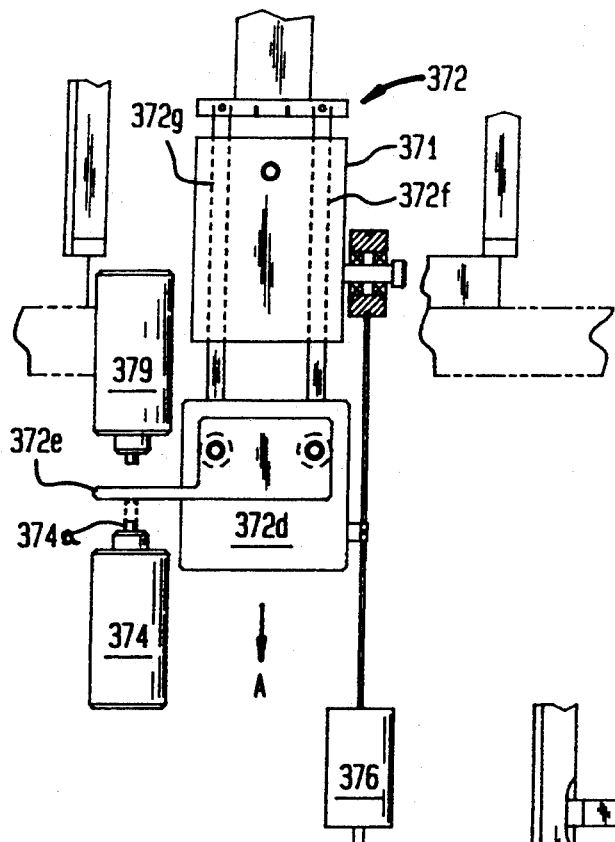
FIG. 31(b) is a detailed front view of the slide assembly means while performing a minimum pull-test.
Figure 31C:
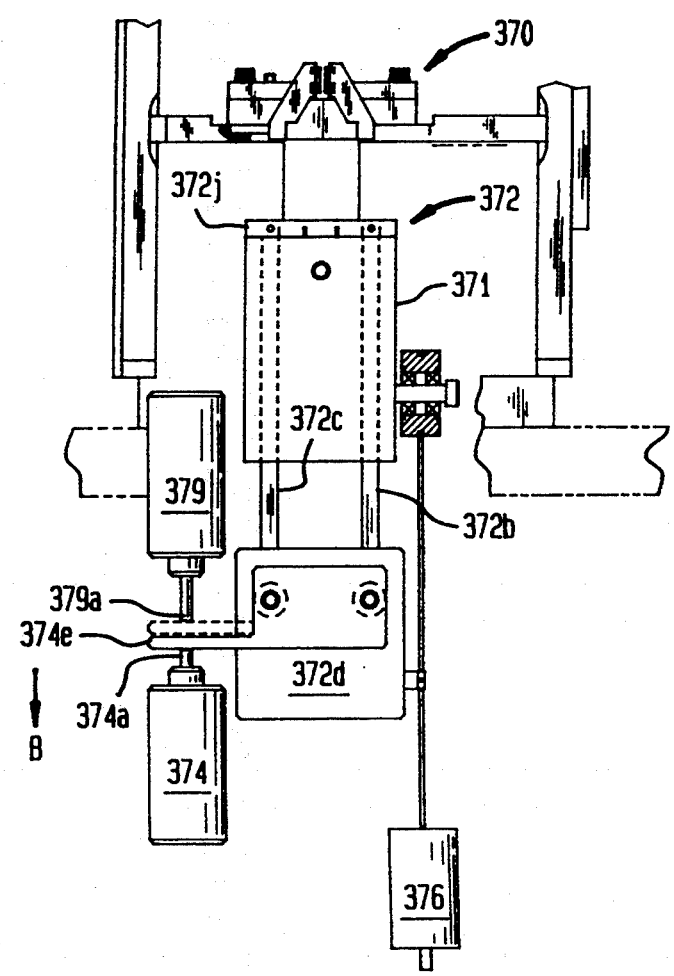
FIG. 31(c) is a detailed front view of the slide assembly means while performing a destructive pull-test.

The automatic pull-test assembly 300 for accomplishing automatic pull-testing of an armed surgical needle is shown generally in FIGS. 30 through 31(c). The automatic pull-test assembly 300 generally comprises a load cell mounting assembly 330 for mounting a load cell 335 which functions to receive the armed needle 39 from the multi-axis gripper 155 which is indexed thereto as shown in FIGS. 30 and 31(a). A needle release assembly 315 is provided for relaxing the armed needle from the grip of the multi-axis gripper 155. Pull-test fence assembly 340 is provided to prevent the armed needle 39 from tipping over or becoming misaligned when the armed needle is relaxed. Suture gripping assembly 370 containing retractable gripper arms 325a, b for gripping the suture 255 during the pull-tests, and which are connected to the weighted slide block assembly 372 for performing the pull-test is provided as shown in FIG. 30. A detailed description of each of these assemblies and their interaction will be explained in detail hereinbelow.

As shown in FIGS. 30 and 31(a), an armed surgical needle 39 is retained by a multi-axis gripper 155 and, in the manner described above, is indexed to the automatic pull test station 300 by the rotary swage dial 150 partially illustrated in the FIG. 30. To position the armed needle 39 in the load cell 335, the multi-axis gripper is extended from the swage dial 150 so that the end portion of needle 39 is positioned above a corresponding receiving blade 336 of the load cell 335 as shown in FIG. 31(a).

Figure 32:
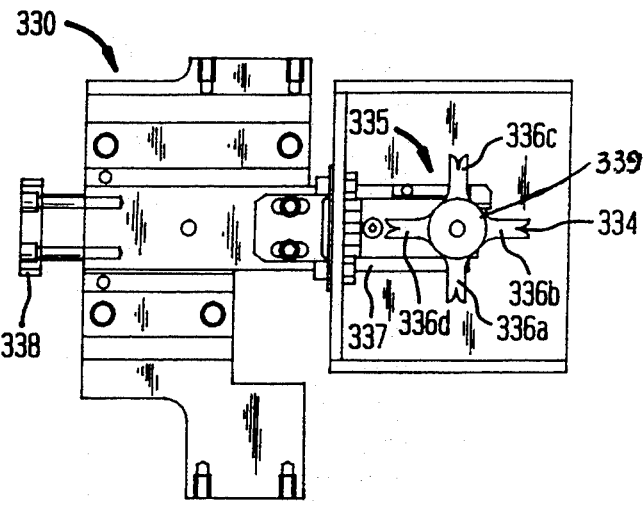
FIG. 32 is a top view of the load cell assembly 330 of the automatic pull-test assembly.

FIG. 32 illustrates a top view of the load cell mounting assembly 330 with load cell 335 mounted thereon. In the preferred embodiment, load cell 335 has mounted thereon four (4) thin needle supporting blades 336a, b, c, d for supporting the suture receiving end portion 37 of various size surgical needles with the suture material 255 depending therefrom. For instance, load cell needle supporting blade 336a labelled "1/0" accommodates a larger sutures having a diameter of approximately 0.017±0.001 inches; load cell needle supporting blade 336b labelled "2/0" accommodates sutures having a diameter of approximately 0.014±0.001 inches; load cell needle supporting blade 336c labelled "3/0" accommodates sutures having a diameter of approximately 0.011±0.001 inches; and load cell needle supporting blade 336d labelled "4/0" accommodates a smaller suture with a diameter of approximately 0.009±0.001 inches in the preferred embodiment. Depending upon the batch of surgical needles currently being pull tested, the appropriate needle supporting blade 336a, b, c, d will be positioned to receive the needle from the multi-axis gripper. Knob 339 located centrally on top of the load cell 335 may be manually operated to rotate the load cell and position the correct sized suture receiving blade prior to carrying out automatic pull-testing. Additionally, the load cell 335 may be laterally positioned by moving slide handle 338 and consequently load cell platter 337 towards or away from the suture needle indicated by the arrow in FIG. 32.

Figure 33:
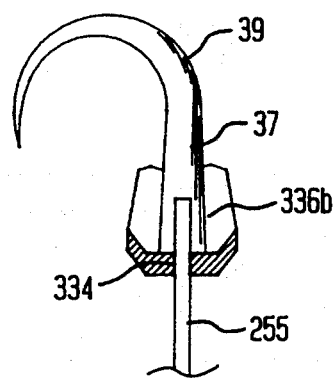
FIG. 33 is an enlarged view of an armed needle 39 supported by the suture receiving blade 336b of the load cell 335 with the suture threaded between the suture receiving opening 334.

The multi-axis gripper 155 is initially positioned so that the end portion of armed needle 39 is supported by the appropriate needle supporting blade 336 (e.g. blade 336b). FIG. 33 is a front cross sectional view illustrating the suture receiving end portion 37 of needle 39 resting upon the needle supporting blade 336b with the suture strand 255 threaded between the suture receiving guide 334.

Non-destructive pull testing of the armed surgical needle 39 is accomplished as follows:

After positioning the multi-axis gripper as heretofore described, gripper arms 325a, b of suture gripping assembly 370 are extended from a retracted position to grip the suture strand 255 slightly below the needle supporting blade 336 of load cell 335 as shown in FIG. 30. A gripper actuator 372a is provided for opening and closing gripper arms 325a, b, as shown in FIG. 30, and is controlled by a control system program resident in control system computer 90 as explained in further detail in copending patent application Ser. No. 08/181,607; filed Jan. 13, 1994 (attorney docket No. 8927) assigned to the same assignee of the present invention. FIGS. 30 and 31(a) illustrate the slide block assembly 372 that is composed of slide rods 372b, c that are connected to a lower slide block 372d. Slide block 372d includes a slide finger 372e upon which air cylinder piston rods 374a and 379a, of respective air cylinders 374, 379, apply respective upward and downward forces depending upon the type of pull-test that is to be performed. As shown in FIG. 31(a), piston rod 374a is shown in an extended position providing an upward force that supports slide finger 372e and consequently maintains slide block 372d of slide assembly 372 at a fixed vertical position.

Slide block 372d is counterweighted to a net downward weight of 2 to 5 ounces by appropriately sized counterweight 376 that acts through cable 373, around pulley 377, and through attachment point 372h. This counterweight 376 acts to pull upward on slide block 372d at the attachment point 372h.

To accomplish the non-destructive pull test, piston rod 374a of air cylinder 374, mounted on the mechanism frame 371 and controlled by system computer 90, is retracted from its extended position (FIG. 31(a)) supporting the slide finger 372e as shown in dashed line in FIG. 31(b), by reversing its air supply (not shown), to the position shown in the Figure. The piston rod 374a is retracted to remove the upward force on slide finger 372e, as shown in the FIG. 31(b), to thereby impose the counterbalanced net weight of 2 to 5 ounces of slide block 372d on the swage attachment means of suture 255 in needle 39, in the direction of arrow "A". Accuracy of this system is enhanced because slide block 372d, suspended on slide rods 372b, c, are mounted in low friction ball bushings, 372f and 372g, that are pressed into slide mount 371, thereby imposing minimal mechanical drag on the system.

Note in FIG. 30, that the slide block mount 371 is positioned parallel to the axis of the suture 255 depending from the needle 39, and is located a distance away from the suture 255 corresponding to the length of the gripper arms 325a, b.

Simultaneous with or momentarily before the slide assembly 372 is released, the needle release assembly 315 is actuated to enable multi-axis gripper 155 to disengage its grip on the armed needle 39. Releasing the armed needle from the grip of the gripper 155 is necessary to ensure that it is firmly positioned on the load cell needle supporting blade 336. Moreover, to provide an accurate pull-test, the needle must be released so that there is no existing upward force that would cause false results.

As shown in FIG. 30, needle release assembly 315 comprises needle release solenoid 324 that is actuated to extend pusher 326 into pivotal lever arm 327. Pivotal lever arm 327 pivots about pin 328 to depress plunger 149 of the multi-axis gripper 155 at one end 329 thereof. As shown in FIG. 31(a), depressing plunger 149 enables pin 142 to retract within pin guide 147 to release the armed needle 39 engaged thereby. Further details of the operation of the multi-axis gripper 155 can be found in the above-mentioned copending patent application Ser. No. 08/181,599; filed Jan. 13, 1994 (attorney docket 8937).

To prevent the armed needle 39 from becoming misaligned or from tipping over after the multi-axis gripper 155 releases its grip on the needle, a needle fence assembly 340 is provided. As shown in FIG. 30, the needle fence assembly 340 includes vertical fence plate 342 which can be adjusted to lie flush against the gripper 155 to retain the armed needle in an upright position. Adjusting the lateral positioning of the vertical fence plate 342 is accomplished by moving slide handle 343 for an appropriate distance as shown in FIG. 30. In the preferred embodiment, the configuration of the face of the vertical needle fence plate 342 (not shown) may be changed to accommodate the configurations of different size needles.

The controlled release of the minimum pull-test is of short duration, preferably ranging in milliseconds. If the test is successful, i.e., the suture meets the minimum pull-test requirements, the needle is re-gripped by the multi-axis gripper 155 by deactuating the needle release solenoid 324 (FIG. 30) which releases the force on plunger 149. The suture grippers 325a, b are then retracted to their open position to release their grip on the suture 255 as controlled by the control system. Subsequently, the multi-axis gripper 155 is retracted and the rotary swage dial is rotated to convey the armed needle downstream for further processing.

Figure 34:
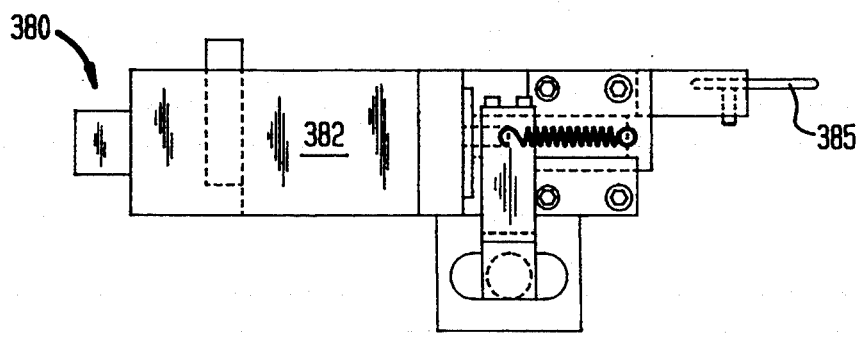
FIG. 34 is a detailed view of the needle stripper assembly 380 for removing the needle 39 after a destructive pull-test or after minimum pull-test failure.

If the suture fails the minimum pull-test, i.e., if the suture 255 is dislodged from the surgical needle 39 as a result of the controlled release, the control system computer 90 is flagged so that the disarmed needle 39 will be ejected at the pull-test station. The dislodged suture strand 255 will be drawn into a vacuum assembly (not shown) and the needle 39 will be ejected by a needle stripper assembly 380 shown generally in FIG. 31(a) and in detail in FIG. 34. As shown in FIG. 34, needle stripper solenoid 382 will be actuated by a control signal output from the control system computer 90 to extend needle stripper blade 385 mounted on a slide block 383. The needle stripper blade 385 is shown in FIG. 30 located next to the needle 39. Thus, when the needle is in its relaxed state on the multi-axis gripper 155 and the minimum pull-test fails, the needle stripper blade 385 is extended to remove the needle from the gripper. The needle will fall and be collected by appropriate collection means (not shown) located at the pull-test station.

To prepare for the next armed needle to be pull-tested, the slide assembly 372 and retracted gripper arms 325a, b are pushed back up the slide mount 371 to their unloaded position by an appropriate upward force supplied by the air cylinder 374 and piston rod 374a as controlled by the control system computer 90. At this time, another flag may be sent for storage to the control system computer that indicates that the pull-test performed on the particular needle 39 was successful and that the armed needle may be conveyed downstream for packaging thereof.

In the preferred embodiment of the minimum and destructive pull-test systems shown in FIGS. 30-33, the load cell 335 and the needle support blades 336a, b, c, d thereof comprise a piezoelectric transducer that measures the force applied by the suture gripping assembly to the needle-suture assembly 39. The transducer load cell 335 may be interfaced with the control system computer 90 by conventional means as shown in FIGS. 30 and 32, and, in the preferred embodiment, is a 1000 gram transducer manufactured by Techniques Co. (Model No. GS-1K). The forces applied to the suture 39 and measured by the load cell transducer 335 during the destructive pull-testing may be stored for statistical purposes or for real-time monitoring during a swage die setup routine that may take place when a new batch of surgical needles are to be swaged. For instance, if the destructive pull-tests fail and the forces measured by the transducer are determined to be at the low end of a predetermined range, then the control system computer 90 will acknowledge this and send appropriate signals to the upstream swaging assembly (not shown) causing a fixed swaging die to be advanced an incremental amount toward the moveable swage die, resulting in subsequent swages being stronger. Likewise, if the destructive pull-test passes, i.e., the forces measured by the transducer are determined to be above the minimum and below an upper limit, then no die adjustment need be made.

As previously mentioned, the automatic pull-test assembly 300 is used to perform a minimum pull-test upon every armed surgical needle indexed thereto prior to automatic packaging thereof. A destructive pull-testing of the armed surgical needle is performed at every nth needle indexed thereto. The purpose of performing a destructive pull-test is to set the swage dies located at the upstream swaging station for correct maximum swage pull-out value. This is by necessity a destructive test, and the test frequency, which is programmable, is set high enough to maintain control of the operation, but low enough to avoid excessive product waste. In the preferred embodiment, this frequency is set at every 50th needle, but could be every 75th or 100th needle.

Another purpose of the destructive pull test is to aid in installing a new swage die set during a changeover procedure, which is a procedure that is used to prepare the needle sorting and swaging apparatuses (swage dies) for processing a new batch of needles when they are of a different size from a previously processed batch. Contrary to the non-destructive pull-test described above, the pull-test apparatus is programmed for 100% destructive test of a swaged needle, while the swaging assembly is operating and feeding the armed needles to the pull-test station. The die adjustment system at the upstream swaging assembly will receive a signal from the transducer load cell 335, at each machine cycle, and quickly perform a correct adjustment of the swage dies.

Destructive test pull-out values are recorded in the system computer 90 and are used to compute statistical process control information which is fed back to the machine operator through display screens.

Destructive pull testing of the armed surgical needle 39 is accomplished similarly as described herein above with respect to the minimum pull test. However, the fundamental difference is that a fixed mechanical stroke that is great enough to pull the suture out of the needle replaces the minimum 2 to 5 ounce force of the minimum pull test.

As shown in FIG. 31(c), piston rod 379a of second air cylinder 379 located opposite air cylinder 374, is programmed to provide a fixed stroke against slide finger 372e from a non-actuating position shown in FIG. 31(a) to the position shown in FIG. 31(c). This results in the vertical displacement of slide finger 372e from a position shown by the dashed line to a position shown by the solid line. This further results in a downward force upon slide block 372d, which, through slide rods 372b and c, moves slide assembly 372, including grippers 325a, b and suture 255, in the direction of the arrow "B" as shown in FIG. 31(c). Air pressure to cylinder 379 is set high enough to always pull suture 255 out of needle 39. This stroke is limited by the top portion 372j of slide assembly 372 striking the top of stationary block 371.

The force necessary to accomplish the destructive pull-test is measured by the piezoelectric load cell transducer 335 as discussed above. If it is determined by the process control algorithm (not shown) that the destructive pull-test forces as measured by the transducer load cell are lower than a predetermined range of pull-test values, the control system computer 90 will send out appropriate control signals to increase the swaging die stroke applied when swaging the suture to the needle at the upstream swaging station. If it is determined that the destructive pull-test forces as measured by the transducer load cell are higher than the predetermined range, the control system computer 90 will send out appropriate control signals to the upstream swaging assembly to move a fixed swage die a small incremental distance away from the suture, thereby decreasing the swaging pressures applied when swaging the suture to the needle.

Since the destructive pull-test necessarily results in the suture 255 becoming dislodged from the needle 39, the needle 39 is again removed from the grip of the multi-axis gripper 155 by the needle stripper blade 385 as described above. Subsequently, the gripper arms 325a, b are retracted to their open positions and air cylinder 374 provides the upward force to restore the gripping assembly 370 and slide block assembly 372 back to their normal position in preparation for the next pull-test.

Die Setup Procedure

The die setup procedure utilizes the swage bond values obtained from a sample of needle suture assemblies pull-tested at pull-test station 300, to adjust the positioning upstream swage dies. This procedure is usually run off-line at the beginning of a batch run or needle changeover procedure, or, it can be run as part of a system re-initialization or error correction routine.

Essentially, during the die setup procedure, the swage assembly produces a sample of 25-30 and preferably 28 needle-suture assemblies for conveyance to the upstream pull-test station. In the manner explained above, all of the sample needle-suture assemblies are destructively pull-tested and the needle-suture destruct values, as measured by the transducer, are stored, analyzed, and compared to a predetermined value that corresponds to either a minimum pull-test force or to an acceptable predetermined maximum destruct value, or combinations thereof. After each successive pull-test, the position of the fixed swage die of the upstream swaging station will vary in accordance with the destruct values obtained and the algorithm (not shown) that is implemented to perform the comparisons. It is understood that minimum and maximum pull-test values will vary in accordance with the type of surgical needle and the attached suture being processed.

Discharge Station

As described hereinabove, the multi-axis gripper 155 is retracted from its extended position at the automatic pull-test station 300 and the rotary swage dial 150 is rotated to index the armed, pull-tested needle to the discharge station 400 for transference to the suture winding and packaging dial 500. Specifically, at station 400, armed needles 39 are inserted within a reduced size organizer package.

As shown in FIG. 1, the suture winding and packaging dial 500 has eight surrounding stations where various processes for packaging of armed surgical needles take place. For instance, at a first station labelled 510 in FIG. 1. an empty package for containing the armed needles may be loaded onto the main dial 500. At a second station labelled 505 in FIG. 1, the presence or absence of the empty package may be detected.

Figure 35:
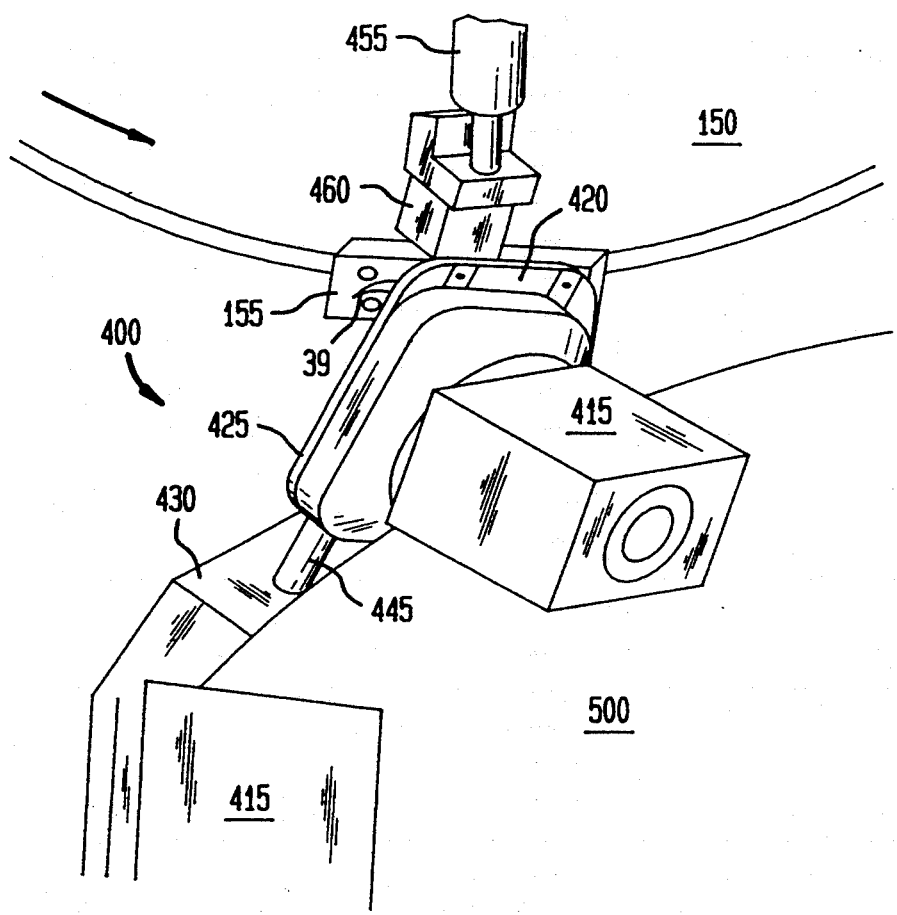
FIG. 35 is a perspective view of the discharge station 400 where suture winding and packaging dial 500 indexes empty package 425 for receiving an armed needle from the multi-axis gripper 155.

In the preferred embodiment shown in FIG. 35, an empty package 425 is loaded on to and gripped by a package nest assembly 415 of the suture winding and packaging dial 500. The package nest assembly 415 comprises a package nest carriage 420 which may be registered in increments so that the empty package 425 may receive eight (8) armed needles. While the preferred embodiment described hereinbelow describes the invention with respect to a reduced size organizer package which receives eight (8) needles, it should be understood that the invention could be used with equal efficiency with a single needle package.

Figure 36:
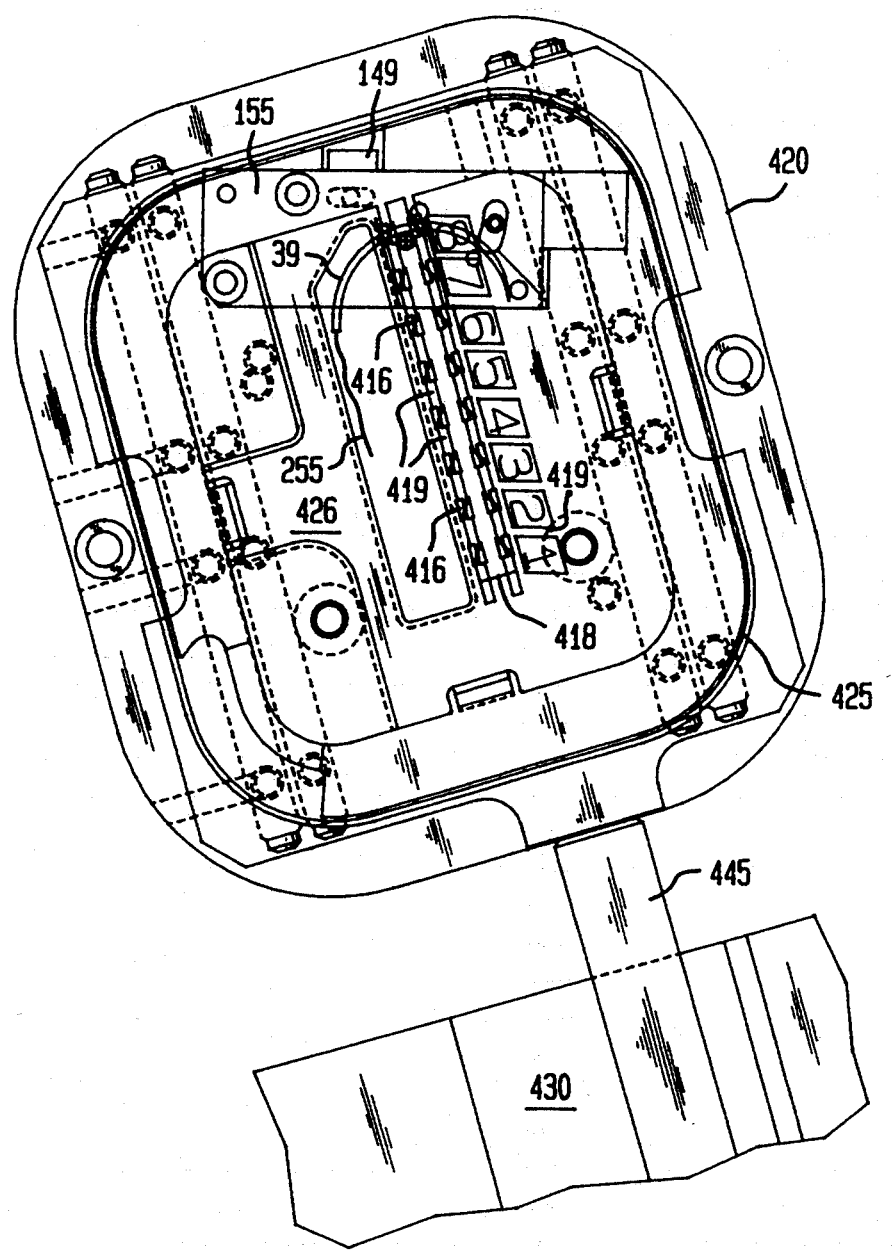
FIG. 36 illustrates the face of Reduced Size Organizer (RSO) package 425 with the face of the multi-axis gripper 155 superimposed thereon after depositing the needle 39 within the first paired set of needle receiving notches 418 of the package 425.

The face of the empty package 425 illustrated in FIG. 36 shows a plurality of grooves for accommodating the sequential placement of eight armed surgical needles. To load the first armed needle into the empty package 425, the carriage is brought to station 400 in its home position shown in FIG. 35. Simultaneous therewith, the rotary swage dial 150 indexes the multi-axis gripper to station 400. Then, the multi-axis gripper 155 is extended toward the empty package 425 to deposit the needle 39 within a first pair 418 of the eight paired sets of needle receiving notches 416 that are formed between protruding fences 419 in the face 426 of the package. In the preferred embodiment, each paired set of notches 418 are consecutively numbered and lie approximately 0.25 inches apart, as shown in FIG. 36. In the preferred embodiment, the first needle loaded is in the eighth position as shown in FIG. 36. As illustrated in FIGS. 35 and 36, the package nest 415 assembly and consequently empty package 425 is slightly tilted with respect to the orientation of the multi-axis gripper 155 so that the curved needle will be accurately deposited within the notches formed in the package. Under control of the control system computer, solenoid 455 then actuates push rod 460 to depress the plunger on the multi-axis gripper 155 so that it may release its grip of the armed needle 39 in the manner described above.

As shown in FIGS. 35 and 36, there is located at the discharge station 400 a package elevator assembly 430 that registers the empty needle package 425 to receive eight individual armed needles, one at a time. The shaft 445 of elevator assembly 430 raises the package nest carriage 420 vertically in 0.25 inch increments to sequentially receive eight needles from the multi-axis gripper 155 as described above. In the preferred embodiment, the rotation of the swage dial 150 supplying armed needles from the pull-test station at a rate of approximately 60/min. is synchronized with the vertical incrementing of the package nest carriage to maximize production rates. For example, after inserting the first armed needle into the empty package 425 into the paired notches numbered "8" as described above, the elevator shaft 445 raises the package nest carriage 420 vertically for 0.25 inches so that the next needle 39 may be deposited in the pair of notches 418 numbered "7." Simultaneous with the registering of the package nest carriage 420, the rotary swage dial 150 indexes the next multi-axis gripper 155 carrying the second armed needle, so that it may insert the next needle in the second position (notch "7") of the empty package 425. This process takes place eight (8) times to fill a reduced size organizer package of eight (8) armed surgical needles. After the eighth needle has been inserted in the package, the elevator assembly 430 retracts the elevator shaft 445 by conventional means such as a pneumatic air cylinder or stepper motor (not shown). Thus, the package 425 carrying the eight armed needles is in its home position on the package nest 415 and the package is ready for further processing at the remaining stations along the suture winding and packaging dial 500.

In a preferred alternate embodiment, the package 425 is in its elevated position and the first needle is inserted into notch labelled number "1". The elevator assembly 430 then is vertically decremented so that successive needle-suture assemblies are successively inserted into notches "2"–"8". When the eighth needle suture assembly is inserted, the package nest carriage 420 and filled package tray are already in their home position.

It should be mentioned that the suture strand 255 depending from the needle is dangling as the needle is inserted into the package 425. Subsequently, at the suture winding station labelled 515 in FIG. 1, all eight dangling sutures are vacuum gathered and wound around the edge of the package as described in detail in copending patent application Ser. No. 08/181,826; filed Jan. 13, 1994 (attorney docket No. 8925) assigned to the same assignee of the present invention.

While the invention has been particularly shown and described with respect to the preferred embodiments thereof, it will be understood by those skilled in the art that the foregoing and other changes in form and details may be made therein without departing from the spirit and scope of the invention, which should be limited only by the scope of the appended claims.

What is claimed:

1. A needle threading and swaging apparatus for attaching a suture to a surgical needle having a suture receiving opening formed therein, said apparatus comprising:
   (a) a first means located at a first location for sorting a plurality of needles and orienting each needle for automatic handling at a first predetermined location;
   (b) a second means located at a second predetermined location for automatically cutting an indefinite length of suturematerial to a definite length and automatically inserting said suture into said suture receiving opening formed in said needle;
   (c) a third means for swaging said needle to close said suture receiving opening about a free end of said suture to secure said suture thereto and form therefrom a needle and suture assembly; and
   (d) indexing means for receiving each individual needle in a predetermined orientation at said first predetermined location and conveying said needle for sequential processing from said first to said second predetermined locations, said indexing means including multi-axis gripper means for retaining said needle in said predetermined orientation, and said multi-axis gripper means being movable between a first retracted position and a second extended position with respect to said indexing means, whereby unsorted needles and an indefinite length of suture material are automatically formed into a plurality of oriented needle and suture assemblies.

2. The needle threading and swaging apparatus according to claim 1 wherein said indexing means further includes a rotary dial means with said multi-axis gripper means positioned radially thereon, said rotary dial means rotatable about a central axis for indexing said multi-axis gripper means sequentially from said first, to said second, to said third, and to said fourth predetermined locations.

3. The needle threading and swaging apparatus according to claim 1 wherein said multi-axis gripper means includes a plurality of pin means for engaging said surgical needle, one of said plurality of pin means being retractable between a first engaging position for engaging said surgical needle in a precisely oriented position, and a second non-engaging position for relaxing said surgical needle.

4. The needle threading and swaging apparatus according to claim 3, wherein said first means for sorting comprises:
(a) infeed means for randomly depositing a predetermined amount of needles upon a first conveyor means;
(b) first means for obtaining an image of said needles deposited upon said first conveyor means, said means including digitizing means for converting said image into digital signals;
(c) computer control means for processing said digital signals to obtain positional and orientation data for a selected randomly positioned needle upon said first conveyor means; and
(d) transfer means for removing said randomly positioned needle from said first conveyor means and positioning it upon a second conveyor means for conveyance thereof,
wherein said transfer means grasps each of said selected needles in accordance with its respective positional and orientation data.

5. The needle threading and swaging apparatus according to claim 4 wherein said infeed means further includes means for singulating each of said predetermined number of needles prior to said deposition upon said first conveyor means, each of said singulated needles being deposited upon said first conveyor means in a spaced apart relation.

6. The needle threading and swaging apparatus according to claim 4 wherein said computer control means further includes a means for processing said positional and orientation data to obtain therefrom instructions for enabling said transfer means to grasp said selected randomly deposited needle in accordance with its respective positional and orientation data.

7. The needle threading and swaging apparatus according to claim 4 wherein said means for obtaining an image of said randomly deposited needles includes one or more video cameras.

8. The needle threading and swaging apparatus according to claim 5 wherein said singulating means further includes at least one reciprocating door means that alternates between a first and second position to split said predetermined amount of needles into first and second groups of needles,
wherein said first group is deposited upon said first conveyor means when said reciprocating door means is in said first position, and said second group is deposited upon said first conveyor means when said reciprocating door means is in said second position.

9. The needle threading and swaging apparatus according to claim 4 wherein said transfer means includes a robot arm means for grasping each of said needles based upon said positional and orientation data received from said computer control means.

10. The needle threading and swaging apparatus according to claim 4 wherein said second conveyor means includes a plurality of carrier means each for receiving a respective needle from said transferring means, each respective carrier means having a means for engaging a respective needle transferred thereto.

11. The needle threading and swaging apparatus according to claim 10 wherein each of said engaging means includes a first fixed jaw and a second movable jaw for engaging a needle positioned therebetween by said transfer means.

12. The needle threading and swaging apparatus according to claim 11 wherein each of said carrier means further includes spring means for biasing said second movable jaw into engagement with said first fixed jaw to retain said needle positioned therebetween.

13. The needle threading and swaging apparatus according to claim 11 wherein said carrier means further includes means for retracting said second movable jaw from engagement with said fixed jaw for removing said needle positioned therebetween.

14. The needle threading and swaging apparatus according to claim 13 wherein said means for retracting said second movable jaw from engagement with said fixed jaw is a push rod for pushing said second movable jaw in opposition to said bias of said spring means.

15. The needle threading and swaging apparatus according to claim 4 further including a second means for obtaining a second video image of said randomly deposited needles, said second video image being processed by said computer control means for obtaining positional and orientation data of a selected randomly deposited needle, and a second transfer means for removing a randomly positioned needle from said first conveyor means and positioning it upon said second conveyor means for conveyance thereof,
wherein said second transfer means grasps a needle based upon its respective positional and orientation data and transfers said needle to said second conveyor means when said computer control means determines that said first transfer means is unable to transfer said randomly deposited needle.

16. The needle threading and swaging apparatus according to claim 10 further including a first orienting blade means for orienting each of said needles positioned on their respective carrier means in a uniform direction.

17. The needle threading and swaging apparatus according to claim 16 further including a second orienting blade means for further orienting said needle within said first and second engagement jaws of said carrier means.

18. The needle threading and swaging apparatus according to claim 17 further including a third orienting blade means for further orienting said needle to within 0.001 inch of said predetermined orientation upon said carrier means.

19. The needle threading and swaging apparatus according to claim 4 wherein said second conveyor means positions said carrier means in a confrontingly opposed relation with said multi-axis gripper means to enable said plurality of pin means of said multi-axis gripper means to receive said oriented needle from said carrier means,
wherein one of said plurality of pin means is in said second non-engaging position when receiving said needle.

20. The needle threading and swaging apparatus according to claim 19 wherein said one of said plurality of pin means of said multi-axis gripper means is retracted to said first engaging position after receiving said surgical needle from said carrier means to thereby engage said surgical needle in said oriented position.

21. The needle threading and swaging apparatus according to claim 20 wherein said indexing means conveys said needle to said second location with said multi-axis gripping means engaging said needle in said oriented position.

22. The needle threading and swaging apparatus according to claim 3, wherein said second means located at said second predetermined location comprises:
(a) a drawing frame, said frame having at least one longitudinal member and defining a drawing axis parallel thereto;
(b) means for feeding a flexible indefinite length suture strand to said drawing axis for drawing and cutting;
(c) first and second gripping means for gripping said indefinite length suture strand and drawing it along said drawing axis, said first gripping means mounted for reciprocal movement on said at least one longitudinal member;
(d) means for cutting said indefinite length suture strand; and
(e) said second gripping means reciprocal to a start position along said drawing axis and below said cutting means, while said first drawing means is drawing said indefinite length suture strand to an insertion zone located a predetermined distance beyond said cutting means,
whereby said indefinite length suture strand is inserted within said suture receiving opening of said needle and cut to a predetermined length by said cutting means after said second gripping means has gripped said indefinite length suture strand at said start position.

23. The needle threading and swaging apparatus according to claim 22 wherein said at least one longitudinal member further defines reciprocal guide means for said first and second gripping means.

24. The needle threading and swaging apparatus according to claim 23 further comprising first and second drive motors for enabling reciprocal movement of respective first and second gripping means.

25. The needle threading and swaging apparatus according to claim 24 further comprising a computer control means for said first and second drive motors to draw said indefinite length suture strand to said predetermined distance beyond said cutting means.

26. An apparatus as claimed in claim 25 further comprising a moveable carrier mounted for selective movement along said drawing axis, said movable carrier having said cutting means mounted thereon.

27. The needle threading and swaging apparatus according to claim 26 wherein said computer control means further comprises at least one sensor means for determining the position of said moveable carrier and said cutting means.

28. The needle threading and swaging apparatus according to claim 22 wherein said feeding means further comprises means for tensioning said indefinite length suture during at least the drawing and cutting thereof.

29. The needle threading and swaging apparatus according to claim 22 wherein each of said first and second gripping means further include retractable gripping elements having a first engaged position and a second retracted position, wherein one of said first and second gripping means traverses the drawing axis on a draw stroke with gripping elements engaged, and the other of said first and second gripping means reciprocates along the same axis with the gripping elements retracted to avoid mechanical interference therewith.

30. The needle threading and swaging apparatus according to claim 22 further including a first vacuum means for temporarily restraining the cut end of said suture strand after cutting thereof.

31. The needle threading and swaging apparatus according to claim 30 further including a second vacuum means for proximate positioning of said indefinite length suture strand prior to cutting.

32. The needle threading and swaging apparatus according to claim 22 wherein said start position defines a treatment zone, said needle threading and swaging apparatus further comprising means for heat treating a portion of said indefinite length strand of suture material while under tension at said treatment zone to form a tipped portion of said indefinite length strand.

33. The needle threading and swaging apparatus according to claim 32 wherein said heat treating means is mounted on said movable carrier.

34. The needle threading and swaging apparatus according to claim 32 wherein said indefinite length strand is being supported at a free end adjacent said insertion zone by said first gripping means while said heat treating means is heating a portion of said strand at said treatment zone, said second gripping means engaging said strand at said start position after heat treating said strand at said treatment zone.

35. The needle threading and swaging apparatus according to claim 34 wherein said cutting means cuts said stiffened strand in said treatment zone to create a suture strand of definite length supported by said first gripping means and a suture strand of indefinite length supported by said second gripping means, with stiffened free ends above each gripping means.

36. The needle threading and swaging apparatus according to claim 22 wherein said third means for swaging includes first and second swaging die means, said first swaging die means having an end thereof defining a portion of a swage die opening, and said second swaging die means having an end thereof defining another portion of said swage die opening, wherein said second swaging die means is positioned next to said first swaging die means to form a swage die opening for receiving said needle.

37. The needle threading and swaging apparatus according to claim 36, wherein said first swaging die means is fixed in position and said second swaging die means is laterally movable toward and away from said first fixed swage die means.

38. The needle threading and swaging apparatus according to claim 36, wherein said swage die opening is axially aligned with said drawing axis, said multi-axis gripper means in said retracted position prior to positioning said surgical needle within said swage die opening, and is extended to position said suture receiving opening of said needle in said swage die opening.

39. The needle threading and swaging apparatus according to claim 38 wherein said third means for swaging further includes a funnel guide means positioned at said insertion zone between a free end of said definite length suture strand and said suture receiving opening of said needle, said funnel die means including a tapered opening axially aligned with said swage die opening for directing said free end of said suture strand into said suture receiving opening of said needle positioned therein.

40. The needle threading and swaging apparatus according to claim 39 wherein said funnel guide means further includes a registration means for aligning it with at least one of said first and second swaging dies.

41. The needle threading and swaging apparatus according to claim 40 wherein said funnel guide means includes a first fixed suture alignment die having an end thereof defining a portion of said tapered opening, and a second movable suture alignment die having an end thereof defining another portion of said tapered opening, wherein said second movable suture alignment die is positioned next to said first fixed suture alignment die to form said tapered opening.

42. The needle threading and swaging apparatus according to claim 39 wherein said tapered opening has a suture exit diameter that is larger than the diameter of said suture strand and smaller than the diameter of said suture receiving opening defined in the needle.

43. The needle threading and swaging apparatus according to claim 42 wherein said first gripping means is advanced along said suture drawing axis to direct said free end of said suture strand through said funnel guide means and into said suture receiving opening of said needle positioned in said swage die opening.

44. The suture threading and swaging apparatus according to claim 38 wherein said swaging means includes means for moving said second swage die means laterally away from said first swage die means prior to positioning said needle within said swage die opening.

45. The needle and suture threading and swaging apparatus according to claim 44, wherein said moving means further moves said second swage die means toward said first swage die means to grip said needle placed therebetween.

46. The needle and suture threading and swaging apparatus according to claim 45 wherein said moving means includes spring biasing means to provide a force sufficient to move said second swage die toward said first swage die without deforming said suture receiving opening of said needle positioned at said swage die opening.

47. The needle and suture threading and swaging apparatus according to claim 46, wherein said moving means includes an air cylinder means for supplying adequate force to thrust said movable swage die means toward said first swage die means to accomplish swaging of said needle gripped therebetween.

48. The needle and suture threading and swaging apparatus according to claim 47, wherein said second swage die means is thrust towards said first die means for a swaging stroke of a predetermined distance to accomplish said swaging.

49. The needle and suture threading and swaging apparatus according to claim 48, wherein said moving means includes stop means for terminating the motion of said second swage die means during said swaging stroke.

50. The needle threading and swaging apparatus according to claim 49 wherein said one of said plurality of pin means is retracted to said second non-engaging position for relaxing said surgical needle in said swage die opening prior to swaging thereof.

51. The needle threading and swaging apparatus according to claim 50, wherein said swaging means further includes fence means for maintaining the position of said needle within said swage die opening during the swaging thereof.

52. The needle threading and swaging apparatus according to claim 46 wherein said swaging means further includes means for adjusting the position of said first swaging die means to change the amount of swage deformation occurring to said suture receiving opening during swaging thereof.

53. The needle threading and swaging apparatus according to claim 52 wherein said first fixed swaging die means includes a wedge follower located at one end thereof, said means for changing the position of said first fixed swaging die means including a wedge assembly positioned to move transverse to said wedge follower to laterally move said wedge follower and said first fixed swaging die means in accordance with transverse movement of said wedge assembly.

54. The needle threading and swaging apparatus according to claim 53 wherein said transverse movement of said wedge assembly is controllable by a servomotor means for rotating a swage adjust screw of a predetermined pitch, said rotation of said swage adjust screw being translated into linear motion of said wedge assembly.

55. The needle threading and swaging apparatus according to claim 54 wherein said computer control means determines and controls the optimum positioning of said first swaging die means to avoid over-swaging and underswaging said needle.

56. The needle threading and swaging apparatus according to claim 22 wherein said cutting means is a retractable cutter comprising:
(a) a cutting blade mounted for at least reciprocal movement transverse to said first axis defined by said indefinite length strand from a first retracted position to a second cutting position;
(b) support block means for accurately positioning said indefinite length strand of suture material for cutting thereof, and for supporting said strand as the cutting blade traverses said first axis as it reciprocates from said retracted position to said cutting position,
whereby said cutting blade is angled with respect to its reciprocating motion to effect a slice ratio of at least 1:1 as said blade cuts said supported suture strand at said cutting position to obtain a clean, broom-free cut.

57. The needle threading and swaging apparatus according to claim 56 wherein said cutting means further comprises:
(a) a stationary guide means, said guide means positioned adjacent said indefinite length suture strand to be cut; and (b) an actuator means mounted on said stationary guide for providing at least reciprocal movement along a second axis transverse to said first axis; wherein said cutting blade is responsive to said reciprocating actuator to move from said first retracted position to said second cutting position.

58. The needle threading and swaging apparatus according to claim 57 further including a locating arm with said support block means located at one end thereof and having another end pivotally mounted to said stationary guide for moving said support block means from a first retracted position to a second strand supporting position in response to movement of said actuator.

59. The needle threading and swaging apparatus according to claim 58, wherein said support block means is a V-shaped notch for supporting said suture strand on two sides during the cutting thereof.

60. The needle threading and swaging apparatus according to claim 59, wherein said pivotal locating arm further comprises an over center link which isolates motion from said actuator means after said support block means has engaged said strand.

61. The needle threading and swaging apparatus according to claim 60, wherein said over center link translates reciprocal movement of said actuator means into pivotal movement for said locating arm.

62. The needle threading and swaging apparatus according to claim 61, wherein said stationary guide is spaced from said indefinite length strand by the effective length of said pivotal locating arm.

63. The needle threading and swaging apparatus according to claim 57, wherein said first axis and said second axis are transverse to each other.

64. The needle threading and swaging apparatus according to claim 57 further including a stationary blade holder mounted on said actuator for supporting said cutting blade during reciprocal motion thereof.

65. The needle threading and swaging apparatus according to claim 61, wherein said over center linkage further comprises first and second links, with said first link fixedly mounted on said actuator and said second link connecting said first link and said pivotal locating arm.

66. The needle threading and swaging apparatus according to claim 57, wherein said cutting blade is angled with respect to said second axis to horizontally cut said strand with a slicing movement when said blade crosses said first axis.

67. The needle threading and swaging apparatus according to claim 66, wherein said cutting blade and said support block means are both retracted behind said stationary guide when in their respective retracted positions.

68. The needle threading and swaging apparatus according to claim 50 wherein said one of said plurality of pin means of said multi-axis gripper means is actuated to said engaging position after swaging of said needle, to thereby engage said needle and suture assembly.

69. The needle threading and swaging apparatus according to claim 3 further including a fourth means located at a third predetermined location for automatically testing the swage bond of said needle and suture assembly, said fourth means including a support means for supporting said needle and suture assembly, said support means having at least one suture receiving guide therein.

70. The needle threading and swaging apparatus according to claim 69 wherein said indexing means conveys said needle and suture assembly to said third location with said multi-axis gripping means engaging said needle in said oriented position.

71. The needle threading and swaging apparatus according to claim 70 wherein said multi-axis gripper means is in said retracted position prior to positioning said needle and suture assembly upon said support means, and is extended to position said needle and suture assembly upon said blade means while enabling said suture strand to be threaded within said suture receiving guide.

72. The needle threading and swaging apparatus according to claim 69 wherein said fourth means for automatically testing the strength of said swage bond of said needle and suture assembly further includes gripping means for positively gripping said suture strand at a first position below said support means, said gripping means including a slide block means for applying a positive downward force of predetermined value to said gripped suture strand to thereby test the strength of said swage bond.

73. The needle threading and swaging apparatus according to claim 72 wherein said fourth means for automatically testing the swage bond of said needle and suture assembly includes means for maintaining said gripping means and said slide block means at said first position prior to applying said positive downward force to said gripped suture.

74. The needle threading and swaging apparatus according to claim 73 wherein said slide block means for applying said positive downward force is a mass of predetermined weight,
wherein said multi-axis gripper means is actuated to release its engagement of said needle and suture assembly at the time of or before said gripping means is released from its first position to enable said slide block means to apply said positive downward force of predetermined value to said suture strand to thereby test the strength of said swage bond.

75. The needle threading and swaging apparatus according to claim 74 wherein said gripping means and said slide block means are slidably mounted along a fixed mounting means, said fixed mounting means positioned substantially parallel with a vertical axis defined by said suture strand.

76. The needle threading and swaging apparatus according to claim 75 wherein said maintaining means includes a first air cylinder means for applying pressure against a first side of said slide block means to maintain said gripping means and said slide block means thereof at said first position.

77. The needle threading and swaging apparatus according to claim 76 wherein said pressure applied to said first side of said slide block means is ceased to enable said slide block means to slide along said mounting means to a second position that is lower than said first position to effect said positive downward force to said gripped suture.

78. The needle threading and swaging apparatus according to claim 72 wherein said fourth means for testing the strength of said swage bond of said needle and suture assembly further includes means for controlling the application of said downward force applied to said suture strand.

79. The needle threading and swaging apparatus according to claim 78 wherein said means for controlling the application of said downward force is a counterweight means, positioned to oppose a gravitational force generated by said slide block means.

80. The needle threading and swaging apparatus according to claim 79 wherein said fourth means for automatically testing the strength of said swage bond further includes one or more of said supporting means for supporting armed surgical needles having different barrel sizes.

81. The needle threading and swaging apparatus according to claim 72 wherein said gripping means includes a pair of retractable gripper arms.

82. The needle threading and swaging apparatus according to claim 74 wherein said fourth means for automatically testing the strength of said swage bond of said needle and suture assembly further includes means for measuring the value of said positive downward force applied to said suture strand by said slide block means.

83. The needle threading and swaging apparatus according to claim 82 wherein said measuring means includes a piezoelectric transducer for measuring the deflection of said support means when said positive downward force is applied to said gripped suture strand.

84. The needle threading and swaging apparatus according to claim 83 further including a computer control means connected with said transducer means for outputting a test fail signal if said suture becomes dislodged from said needle after application of said downward force.

85. The needle threading and swaging apparatus according to claim 84 wherein said computer control means enables the automatic adjustment of said third means for swaging in accordance with measured values obtained from said measuring means.

86. The needle threading and swaging apparatus according to claim 85 wherein said fourth means for automatically testing said swage bond further includes means for removing said needle from said multi-axis gripper means upon receipt of said test fail signal from said control means.

87. The needle threading and swaging apparatus according to claim 81 wherein said multi-axis gripper means is retracted from an extended position after pull-testing said needle and suture assembly.

88. The needle threading and swaging apparatus according to claim 3 further including a fifth means located at a fourth predetermined location for automatically receiving said needle and suture assembly and for packaging the same as a reduced size organizer.

89. The needle threading and swaging apparatus according to claim 88, wherein said indexing means conveys said needle and suture assembly to said fourth predetermined location for transferring said needle and suture assembly to said fifth means for receiving said needle suture assembly.

90. The needle threading and swaging apparatus according to claim 89 wherein said fifth means for receiving said needle and suture assembly includes retractable carriage means for gripping an empty package to be loaded with said needle and suture assemblies.

91. The needle threading and swaging apparatus according to claim 90 wherein said retractable carriage means carries said empty package in an oriented position, said fifth means for receiving said needle and suture assembly including means for incrementally registering said oriented package in a plurality of positions.

92. The needle threading and swaging apparatus according to claim 91 wherein said means for registering said oriented package includes an elevator assembly having a pneumatically operated shaft for registering said retractable carriage means to said plurality of positions.

93. The needle threading and swaging apparatus according to claim 92 wherein said indexing means conveys said multi-axis gripper means in a confrontingly opposed relation with said empty package, said multi-axis gripper means depositing an individual oriented needle and suture assembly into a needle receiving engagement means formed in said empty package at each registered position.

94. The needle threading and swaging 30 apparatus according to claim 2 wherein said indexing means further includes cam dial means includes one or more cam tracks located about a periphery of said rotary dial means, each of said cam tracks defining a retracted portion thereof and an extended portion thereof.

95. The needle threading and swaging apparatus according to claim 94 wherein said multi-axis gripper means includes a cam follower means positioned within a respective cam track of said cam dial means for extending said multi-axis gripper means when said cam follower is positioned within said extended portion of said cam track and for retracting said multi-axis gripper means when said cam follower is positioned within said retracted portion of said cam track.

96. The needle threading and swaging apparatus according to claim 95 wherein said rotary dial means is rotated in a first direction relative to said cam dial means to move said cam follower of said multi-axis gripper means from said retracted portion to said extended portion, thereby moving said multi-axis gripper means from said first retracted position to said second extended position.

97. The needle threading and swaging apparatus according to claim 96 wherein said rotary dial means is rotated in a second direction relative to said cam dial means to move said cam follower of said multiaxis gripper means from said extended portion back to said first retracted portion, thereby moving said multiaxis gripper means from said second extended position back to said first retracted position.

* * * * *

UNITED STATES PATENT AND TRADEMARK OFFICE
CERTIFICATE OF CORRECTION

PATENT NO. : 5,438,746
DATED : August 8, 1995
INVENTOR(S) : David Demarest, Robert B. Duncan, John F. Blanch It is certified that error appears in the above-indentified patent and that said Letters Patent is hereby corrected as shown below:

Column 48 - Line 28 - "30" should be deleted

Signed and Sealed this

Thirty-first Day of December, 1996

Attest:

BRUCE LEHMAN

*Attesting Officer*     *Commissioner of Patents and Trademarks*